(12) United States Patent
Baym et al.

(10) Patent No.: US 9,390,457 B2
(45) Date of Patent: Jul. 12, 2016

(54) DEVICES AND METHODS FOR COMPETENCY TRAINING AND USE AUTHORIZATION FOR DISPENSING AN AGENT

(71) Applicant: Elwha LLC, Bellevue, WA (US)

(72) Inventors: Michael H. Baym, Cambridge, MA (US); Jesse R. Cheatham, III, Seattle, WA (US); Philip A. Eckhoff, Bellevue, WA (US); Roderick A. Hyde, Redmond, WA (US); Jordin T. Kare, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 285 days.

(21) Appl. No.: 13/874,032

(22) Filed: Apr. 30, 2013

(65) Prior Publication Data

US 2014/0322683 A1    Oct. 30, 2014

(51) Int. Cl.
*G06Q 50/22* (2012.01)
*G09B 5/00* (2006.01)
*G09B 19/24* (2006.01)
*G09B 25/02* (2006.01)

(52) U.S. Cl.
CPC ....... *G06Q 50/22* (2013.01); *G09B 5/00* (2013.01); *G09B 19/24* (2013.01); *G09B 25/025* (2013.01)

(58) Field of Classification Search
CPC .......... A61J 7/04; A61J 7/0092; G09B 23/28; G09B 5/00; G09B 19/24; G09B 25/025; G06Q 50/22
See application file for complete search history.

(56) References Cited

U.S. PATENT DOCUMENTS

| | | |
|---|---|---|
| 4,384,288 A | 5/1983 | Walton |
| 4,984,158 A | 1/1991 | Hillsman |
| 5,363,842 A | 11/1994 | Mishelevich et al. |
| 5,431,154 A | 7/1995 | Seigel et al. |
| 5,571,152 A | 11/1996 | Chen et al. |
| 6,358,058 B1 | 3/2002 | Strupat et al. |
| 6,386,882 B1 * | 5/2002 | Linberg ............... G06F 19/324 434/262 |
| 6,994,934 B2 | 2/2006 | Stanish et al. |

(Continued)

OTHER PUBLICATIONS

Arora, Anubhav et al., "Needle-free delivery of macromolecules across the skin by nanoliter-volume pulsed microjets", PNAS, Mar. 13, 2007, pp. 4255-4260, vol. 104, No. 11.

Brearley, Chris et al., "Pharmacokinetics of recombinant human growth hormone administered by cool.click™ 2, a new needle-free device, compared with subcutaneous administration using a conventional syringe and needle", BMC Clinical Pharmacology, Oct. 8, 2007, pp. 1-7, vol. 7, No. 10, Brearley et al.

(Continued)

*Primary Examiner* — Timothy A Musselman

(57) ABSTRACT

Devices and methods for competency training and use authorization for dispensing an agent are described, which include: an agent-dispensing device including a reservoir configured to store agents, a controllable agent-dispensing mechanism in communication with the reservoir, a locking mechanism coupled to the controllable agent-dispensing mechanism, a microprocessor including circuitry, use sensors to monitor at least one operational step for use of the agent-dispensing device, training circuitry configured to train the user and to assign a value for each of the monitored at least one operational step for use of the agent-dispensing device, verification circuitry configured to determine if the assigned value for each of the monitored at least one operational step for use of the agent-dispensing device meets or exceeds a pre-defined performance threshold, and activation circuitry responsive to the verification circuitry and configured to deactivate the locking mechanism to allow dispensing of agents if the assigned value meets or exceeds the pre-defined performance threshold.

25 Claims, 27 Drawing Sheets

(56) References Cited

U.S. PATENT DOCUMENTS

| | | | |
|---|---|---|---|
| 6,997,911 | B2 | 2/2006 | Klitmose |
| 7,072,738 | B2 | 7/2006 | Bonney et al. |
| 7,189,471 | B2 | 3/2007 | Jankowksi et al. |
| 7,194,801 | B2 | 3/2007 | Jenson et al. |
| 7,215,976 | B2 | 5/2007 | Brideglall |
| 7,238,628 | B2 | 7/2007 | Demaray et al. |
| 7,322,355 | B2 | 1/2008 | Jones et al. |
| 7,825,776 | B2 | 11/2010 | Smith et al. |
| 2001/0022279 | A1 | 9/2001 | Denyer et al. |
| 2004/0074921 | A1 | 4/2004 | Lips et al. |
| 2004/0241627 | A1 | 12/2004 | Delfing |
| 2006/0130828 | A1 | 6/2006 | Sexton et al. |
| 2006/0130829 | A1 | 6/2006 | Sexton et al. |
| 2007/0074722 | A1 | 4/2007 | Giroux et al. |
| 2007/0184812 | A1 | 8/2007 | Bitton |
| 2007/0186923 | A1 | 8/2007 | Poutiatine et al. |
| 2008/0114299 | A1 | 5/2008 | Damgaard-Sorensen et al. |
| 2008/0125724 | A1 | 5/2008 | Monroe |
| 2008/0147044 | A1 | 6/2008 | Palmer et al. |
| 2009/0074262 | A1 | 3/2009 | Kudavelly |
| 2009/0243813 | A1 | 10/2009 | Smith et al. |
| 2009/0276090 | A1 | 11/2009 | Rajiv |
| 2009/0299827 | A1 | 12/2009 | Puri et al. |
| 2010/0203487 | A1 | 8/2010 | Cyr et al. |
| 2010/0298956 | A1 | 11/2010 | Van Eeden et al. |
| 2011/0166700 | A1 | 7/2011 | Dunn |
| 2012/0035986 | A1 | 2/2012 | Jimenez |
| 2013/0002795 | A1 | 1/2013 | Shavelsky et al. |
| 2013/0266919 | A1* | 10/2013 | Baker ............... G09B 23/285 434/262 |
| 2014/0120505 | A1* | 5/2014 | Rios et al. ............... 434/219 |
| 2014/0272834 | A1 | 9/2014 | Washburn et al. |

OTHER PUBLICATIONS

Chawla, Vipul et al., "An Overview of Passive RFID", IEEE Applications & Practice, Sep. 2007, pp. 11-17, IEEE.

Finkenzeller, Klaus, "Fundamental Operating Principles", RFID Handbook: Fundamentals and Applications in Contactless Smart Cards and Identification, 2003, pp. 29-59, Ch. 3, John Wiley & Sons, Ltd.

"Highlights of Prescribing Information", Roxane Laboratories, Inc., revised Jan. 2012, pp. 1-10, http:/www.accessdata.fda.gov/drugsatfda_docs/label/2010/022195s002lbl.pdf, RLI.

Kasha, Purna C. et al., "Subcutaneous concentrations following topical iontophoretic delivery of diclofenac", Drug Discoveries & Therapeutics, pp. 256-262, vol. 6, No. 5.

Kim, Yeu-Chun et al., "Enabling skin vaccination using new delivery technologies", Curr Top Microbiol Immunol., NIH Public Access Author Manuscript, 2012, vol. 351, pp. 77-112.

Oxycodone, Drugs.com, printed on Apr. 4, 2013, pp. 1-24, http://www.drugs.com/pro/oxycodone.html?printable=1.

Phillips, P. Jonathon et al., "Preliminary Face Recognition Grand Challenge Results", Proceedings of the 7th International Conference on Automatic Face and Gesture Recognition, 2006, pp. 1-7, IEEE.

Szeliski, Richard, "Image Alignment and Stitching: A Tutorial", Foundations and Trends® in Computer Graphics and Vision, 2006, pp. 1-104, vol. 2, No. 1, R. Szeliski.

Zitová, Barbara et al., "Image registration methods: a survey", Image and Vision Computing, 2003, pp. 977-1000, vol. 21, Elsevier B.V.

PCT International Search Report; International App. No. PCT/US2014/035808; Sep. 17, 2014; pp. 1-3.

* cited by examiner

Fig. 18

1800
Providing a web-based interactive tool to the user through a computing device, the web-based interactive tool including stored text, images, audio, and/or video, and
    a training module to provide training to the user in proper use of the agent-dispensing device,
    a verification module to verify a competency of the user in the proper use of the agent-dispensing device, and
    an activation module responsive to the verification module and operable to provide an activation signal to deactivate a locking mechanism of the agent-dispensing device 1810
Training the user in the proper use of the agent-dispensing device using the training module of the web-based interactive tool 1820
Verifying a competency of the user in the proper use of the agent-dispensing device using the verification module of the web-based interactive tool 1830
Activating the agent-dispensing device with the activation module of the web-based interactive tool by providing the activation signal to deactivate the locking mechanism to allow dispensing of one or more agents from the agent-dispensing device after verifying the competency of the user in the proper use of the agent-dispensing device

Fig. 20

1800
Providing a web-based interactive tool to the user through a computing device, the web-based interactive tool including stored text, images, audio, and/or video, and
    an authorization module including circuitry configured to authenticate the user as an authorized user of the web-based interactive tool,
    a training module to provide training to the user in proper use of the agent-dispensing device,
    a verification module to verify a competency of the user in the proper use of the agent-dispensing device, and
    an activation module responsive to the verification module and operable to sent an activation signal to deactivate a locking mechanism of the agent-dispensing device

2000
Providing the web-based interactive tool to the user through a desktop computer, a laptop computer, a tablet computing device, a personal electronic device, or a dedicated computing device accessible to the user

2010
Providing the web-based interactive tool to the user through the computing device via the Internet

2020
Providing the web-based interactive tool to the user through the computing device in communication with a remote server

1810

1820

1830

DEVICES AND METHODS FOR COMPETENCY TRAINING AND USE AUTHORIZATION FOR DISPENSING AN AGENT

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None

RELATED APPLICATIONS

U.S. patent application Ser. No. 13/873,991, entitled SYSTEMS AND METHODS FOR COMPETENCY TRAINING AND USE AUTHORIZATION FOR DISPENSING AN AGENT, naming MICHAEL H. BAYM, JESSE R. CHEATHAM, III, PHILIP A. ECKHOFF, RODERICK A. HYDE, JORDIN T. KARE, AND LOWELL L. WOOD, JR. as inventors, filed 30, Apr. 2013, is related to the present application.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In an aspect, a system for competency training and use authorization for dispensing an agent includes, but is not limited to: an agent-dispensing device configured to dispense one or more agents to a user, the agent-dispensing device including a controllable agent-dispensing mechanism; the agent-dispensing device including a receiver configured to receive a signal and to activate or deactivate a locking mechanism coupled to the controllable agent-dispensing mechanism; a computing device having a display and a user interface; and a web-based interactive tool including stored text, images, audio, or video accessible to the user on the computing device, the web-based interactive tool including a training module to provide training to the user in proper use of the agent-dispensing device; a verification module to verify a competency of the user in the proper use of the agent-dispensing device; and an activation module responsive to the verification module and operable to provide an activation signal to the receiver to deactivate the locking mechanism to allow dispensing of the one or more agents from the agent-dispensing device after verifying the competency of the user. In addition to the foregoing, other system aspects are described in the claims, drawings, and text forming a part of the present disclosure.

In an aspect, a method of verifying user competency of an agent-dispensing device includes, but is not limited to: providing a web-based interactive tool to a user through a computing device, the web-based interactive tool including stored text, images, audio, and/or video, and a training module to provide training to the user in proper use of the agent-dispensing device, a verification module to verify a competency of the user in the proper use of the agent-dispensing device, and an activation module responsive to the verification module and operable to provide an activation signal to deactivate a locking mechanism of the agent-dispensing device; training the user in the proper use of the agent-dispensing device using the training module of the web-based interactive tool; verifying a competency of the user in the proper use of the agent-dispensing device using the verification module of the web-based interactive tool; and activating the agent-dispensing device with the activation module of the web-based interactive tool by providing the activation signal to deactivate the locking mechanism to allow dispensing of one or more agent from the agent-dispensing device after verifying the competency of the user in the proper use of the agent-dispensing device. In addition to the foregoing, other method aspects are described in the claims, drawings, and text forming a part of the present disclosure.

In an aspect, a computer implemented method for authorizing use of an agent-dispensing device following competency training includes, but is not limited to: connecting a user to a web-based interactive tool through a bi-directional communication network link; receiving authorization information associated with the user through the bi-directional communication network link; authenticating the user as an authorized candidate for competency training; selecting a training module from the web-based interactive tool corresponding to the competency training which the user is authorized to access; executing a set of at least one skill-based simulated training software corresponding to the training module selected from the web-based interactive tool; generating a set of training results for the user upon completion of the training module; certifying the user is competent to use the agent-dispensing device if the set of training results for the user meets or exceeds a pre-defined performance threshold; and issuing over the bi-directional communication network link an authorization key to the user to allow the user to deactivate a locking mechanism associated with a controllable agent-dispensing mechanism of the agent-dispensing device. In addition to the foregoing, other method aspects are described in the claims, drawings, and text forming a part of the present disclosure.

In an aspect, an agent-dispensing device includes, but is not limited to: a housing including at least one reservoir configured to store one or more agents; a controllable agent-dispensing mechanism in communication with the at least one reservoir; a locking mechanism coupled to the controllable agent-dispensing mechanism; a microprocessor including instructions for operating the agent-dispensing device in a dispensing mode or a training mode; one or more use sensors configured to monitor at least one operational step for use of the agent-dispensing device in the training mode; training circuitry configured to train the user in the at least one operational step for use of the agent-dispensing device and to assign a value for each of the monitored at least one operational step for use of the agent-dispensing device in the training mode; verification circuitry configured to determine if the assigned value for each of the monitored at least one operational step for use of the agent-dispensing device in the training mode meets or exceeds a pre-defined performance threshold; and activation circuitry responsive to the verification circuitry and configured to deactivate the locking mechanism to allow dispensing of the one or more agents if the assigned value for each of the monitored at least one operational step for use of the agent-dispensing device in the training mode meets or exceeds the pre-defined performance threshold. In addition to the foregoing, other device aspects are described in the claims, drawings, and text forming a part of the present disclosure.

In an aspect, a method of verifying user competency implemented with circuitry in an agent-dispensing device includes, but is not limited to: authenticating a user as an authorized user of the agent-dispensing device, wherein the agent-dispensing device includes at least one of authorization circuitry, training circuitry, one or more use sensors, verification circuitry, or activation circuitry; training the user in at least one operational step for use of the agent-dispensing device with one or more training instructions included in the training circuitry; monitoring the user's performance of the at least one operational step for use of the agent-dispensing device with the one or more use sensors; assigning a value to each of the monitored at least one operation step for use of the agent-dispensing device performed by the user; verifying with the verification circuitry if the assigned value for each of the monitored at least one operational step for use of the agent-dispensing device meets or exceeds a pre-defined performance threshold; activating the agent-dispensing device with activation circuitry responsive to the verification circuitry to allow dispensing of one or more agents from the agent-dispensing device if the assigned value for each of the monitored at least one operational step for use of the agent-dispensing device meets or exceeds the pre-defined performance threshold. In addition to the foregoing, other method aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 18 is a flowchart of a method of verifying user competency of an agent-dispensing device.

FIG. 20 is a flowchart showing further aspects of a method such as depicted in FIG. 18.

DETAILED DESCRIPTION

Figure 1:
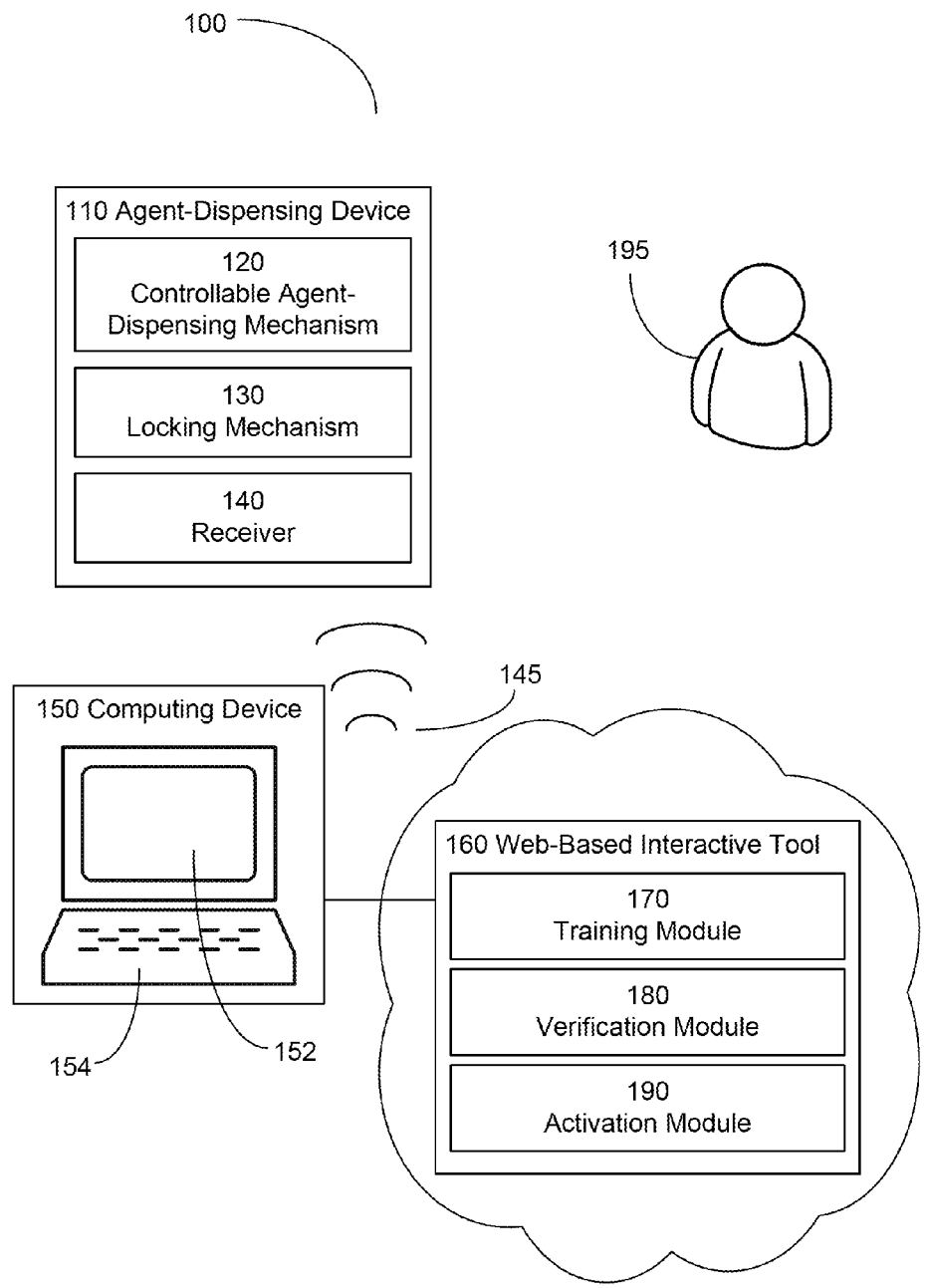
FIG. 1 is a schematic of an embodiment of a system for competency training and use authorization for dispensing an agent.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

With reference to FIG. 1, shown is a schematic view of a system 100 for competency training and use authorization for dispensing an agent. System 100 includes agent-dispensing device 110 and computing device 150 and web-based interactive tool 160 accessible to user 195 through computing device 150. Agent-dispensing device 110 is configured to dispense one or more agents to user 195 and includes controllable agent-dispensing mechanism 120 and receiver 140 configured to receive a signal 145 and to activate or deactivate locking mechanism 130 coupled to controllable agent-dispensing mechanism 120. Computing device 150 further includes display 152 and user interface 154. Web-based interactive tool 160 includes training module 170 to provide training to user 195 in proper use of agent-dispensing device 110, verification module 180 to verify a competency of user 195 in the proper use of agent-dispensing device 110, and activation module 190 responsive to verification module 180 and operable to provide an activation signal 145 to receiver 140 to deactivate locking mechanism 130 to allow dispensing of one or more agents from agent-dispensing device 110 after verifying the competency of user 195.

System 100 includes components and features for training a user in the proper use of an agent-dispensing device and any agent contained or dispensed from said agent-dispensing device. System 100 also includes components and features for verifying the competency of the user in the proper use of an agent-dispensing device and/or any agent contained or dispensed from said agent-dispensing device prior to deactivating a locking mechanism associated with the controllable agent-dispensing mechanism of the device. In this way, only a competent user(s) is allowed access to the contents of the agent-dispensing device.

In one embodiment, user 195 is trained using web-based interactive tool 160 to self-administer one or more agents from agent-dispensing device 110. For example, user 195 may be trained, training verified, and locking mechanism 130 of agent-dispensing device 110 deactivated using web-based interactive tool 160 to allow self-administration of a highly regulated prescription pain medication, e.g., oxycodone. For example, user 195 may live in a remote location, receive an agent-dispensing device in the mail, e.g., by certified mail, with instructions for accessing web-based interactive tool 160 through the Internet using a computing device.

In one embodiment, user 195 is trained using web-based interactive tool 160 to administer one or more agents from agent-dispensing device 110 to one or more other individuals. For example, user 195 may be a caregiver, e.g., an aid worker, in a remote location who is trained, training verified, and locking mechanism 130 of agent-dispensing device 110 deactivated using web-based interactive tool 160 accessed via the Internet to administer one or more agents, e.g., a vaccine, to one or more individuals in the remote location, e.g., a developing country. For example, user 195 may be a user attending to a sick family member, e.g., a child or a parent, in a remote location, e.g., at a distance from a medical facility, who is trained, training verified, and the locking mechanism of an agent-dispensing device deactivated using the web-based interactive tool, to administer an opioid pain reliever, e.g., morphine, to the sick family member. In one embodiment, the user can include individuals who are otherwise not medically trained but are authorized to administer an agent to either themselves or other individuals after proper training and verification using the web-based interactive tool.

System 100 includes agent-dispensing device 110. Agent-dispensing device 110 is configured to controllably dispense one or more agent for preventing and/or treating a disease or medical condition. In one embodiment, the one or more agents include one or more therapeutic agents. In one embodiment, the one or more agents include one or more preventative agents. Non-limiting examples of diseases and/or conditions include but are not limited to cardiovascular disorders, renal disorders, metabolic disorders, neurodegenerative disorders, psychological disorders, neuromuscular and pain disorders, gastrointestinal disorders, gynecological and urological disorders, cancer, inflammation, autoimmune disorders, dermatological disorders, microbial infections and the like.

Agent-dispensing device 110 is configured to controllably dispense one or more agents upon activation of the agent-dispensing device in response to verification that the user is qualified to use the agent-dispensing device, the one or more agents, or any associated agent-containing cartridges. In one embodiment, agent-dispensing device 110 includes one or more reservoirs including one or more agents for treating and/or preventing one or more disease and/or condition. In one embodiment, agent-dispensing device 110 includes one or more receptacle or docking site configured to accept one or more agent-containing cartridges. The agent-containing cartridges can be filled with one or more agents for treating and/or preventing one or more disease and/or condition.

Agent-dispensing device 110 can include one or more of an injection device, an inhalation device, a solid form dispensing device, a liquid form dispensing device, a gas form dispensing device, or a transdermal dispensing device. In one embodiment, agent-dispensing device 110 is configured for intranasal administration of a therapeutic or preventative agent. In one embodiment, agent-dispensing device 110 is configured for vaginal or rectal administration of a therapeutic or preventative agent. In general, agent-dispensing device 110 can be configured to administer one or more agents to one or more of an ear, a nostril, a mouth, a throat, a lung, skin, ureter, vagina, or rectum. In one embodiment, agent-dispensing device 110 can be a smart pill intended for oral ingestion or rectal insertion. In one embodiment, agent-dispensing device 110 is implantable. In one embodiment, agent-dispensing device 110 is sized for placement into either the vascular or lymphatic system. In one embodiment, agent-dispensing device 110 is a self-contained, handheld device containing all of the components needed for activation and controllable release of one or more therapeutic or preventative agents. In one embodiment, agent-dispensing device 110 may include a mobile, e.g., hand-held or implantable component in wired or wireless communication with a less-mobile control component. For example, the mobile component may include a controllable agent-dispensing mechanism, a locking mechanism, a receiver and its own power source while the less-mobile control component may include control circuitry, a transmission unit, a power source, and any of a number of other components. For example, the mobile component may be a syringe-like dispensing device in wireless communication with a table-top control unit. The table-top control unit may further include the computing device on which the web-based interactive tool is accessed to facilitate training and verification prior to activation of the system for authorized agent dispensing. In one embodiment, agent-dispensing device 110 may include an implantable portion in wireless communication with a hand-held portion, e.g., a personal electronic device, the latter of which may serve as the computing device capable of accessing the web-based interactive tool to provide training and verification for the user and activation of the implanted portion of the system.

Agent-dispensing device 110 includes controllable agent-dispensing mechanism 120. Controllable agent-dispensing mechanism 120 can include any of a number of means for dispensing a therapeutic or preventative agent for treating and/or preventing a disease and/or condition. Non-limiting examples of controllable agent-dispensing mechanisms include one or more of an inhalation dispensing mechanism, an injection dispensing mechanism, an intranasal dispensing mechanism, a rectal dispensing mechanism, an intravaginal dispensing mechanism, a transdermal dispensing mechanism, a solid form dispensing mechanism, a liquid form dispensing mechanism, or a gas form dispensing mechanism.

In one embodiment, controllable agent-dispensing mechanism 120 includes an inhalation dispensing mechanism. Non-limiting examples of inhalation dispensing mechanisms include dry powder inhalation, nebulization, or metered-dose inhalation. For example, agent-dispensing device 110 may include controllable agent-dispensing mechanism 120 that is a metered-dose inhalation dispensing mechanism for use in administering an inhaled agent, e.g., a corticosteroid and/or beta-adrenoceptor agonist, for treating asthma or chronic obstructive pulmonary disease. Non-limiting examples of inhaler devices including processors and circuitry are described in U.S. Patent Application 2006/0130828; U.S. Patent Application 2007/0074722; which are incorporated herein by reference.

In one embodiment, controllable agent-dispensing mechanism 120 includes an injection dispensing mechanism. The injection dispensing mechanism can include needle or needleless injection dispensing mechanisms. In one embodiment, controllable agent-dispensing mechanism 120 can include one or more retractable injection needles. For example, one or more needles may be retracted into agent-dispensing device 110 until an activation signal is sent to deactivate a locking mechanism to allow extension of the one or more needles. In one embodiment, controllable agent-dispensing mechanism 120 may control passage of an injectable agent through the one or more needles. For example, the controllable agent-dispensing mechanism may include a plunger for forcing an injectable agent through the one or more needles, the plunger only functional when an activation signal has been sent to the receiver to deactivate a locking mechanism associated with the plunger. For example, the controllable agent-dispensing mechanism may include a needleless injection system, e.g., a jet-injection system, for use in administering a vaccine. A non-limiting example of a jet injection system is described in Kim & Prausnitz, *Curr. Top. Microbiol. Immunol.* (2012) 351:77-112, which is incorporated herein by reference. Other non-limiting examples of injectors include single needle injector, multi-needle injector, or micro-needles. The needles can be part of an injector device, e.g., a syringe-like device, or part of a patch, e.g., a transdermal patch with micro-needles. Other non-limiting examples of injection mechanisms configured for dispensing a therapeutic and/or preventative agent include microject injection mechanisms (see, e.g., Arora et al., *Proc. Natl. Acad. Sci.* (2007) 104:4255-4260, which is incorporated herein by reference) and needle free injection mechanisms (see, e.g., Brearley et al., *BMC Clinical Pharmacology* (2007) 7:10; 1472-6904/7/10, which is incorporated herein by reference). A non-limiting example of an injector with a processor is described in U.S. Pat. No. 6,997,911, which is incorporated herein by reference.

In one embodiment, controllable agent-dispensing mechanism 120 includes an intranasal dispensing mechanism. The intranasal dispensing mechanism can include snorting a liquid or dry powder, liquid drops using a syringe or a dropper, squeeze bottle delivery, sprayed or atomized delivery, or nebulized delivery. In one embodiment, controllable agent-dispensing mechanism 120 may include a controllable opening in a portion of agent-dispensing device 110 that is inserted into a nasal passage, the controllable opening only open when an activation signal has been sent to the receiver to deactivate a locking mechanism.

In one embodiment, controllable agent-dispensing mechanism 120 includes a transdermal dispensing mechanism. Examples of transdermal dispensing mechanisms include, but are not limited to, passive and active dispensing mechanisms. An example of a passive dispensing mechanism includes release from one or more reservoirs associated with agent-delivery device of one or more agents capable of being passively absorbed through the skin. Non-limiting examples include any of a number of agents formulated for use in a transdermal patch, e.g., estrogen, testosterone, analgesics, or nicotine. Non-limiting examples of an active dispensing mechanism includes ionophoresis, electroporation, or microprojections to actively transport one or more agents through the skin. For example, agent-dispensing device 110 may be a transdermal patch with an active controllable agent-dispensing mechanism 120, e.g., an iontophoretic patch, which controllably releases an agent, e.g., an analgesic agent for mitigating pain, across the dermal layer. A non-limiting example of an iontophoretic transdermal patch is described in Kasha et al., *Drug Discov. Ther.* (2012) 6:256-262, which is incorporated herein by reference.

In one embodiment, agent-dispensing device 110 includes an oral drug dispenser. For example, agent-dispensing device 110 may hold one or more orally administered agents, e.g., a pill or oral solution, that are controllably released from agent-dispensing device 110 after training, verification, and activation.

In one embodiment, controllable agent-dispensing mechanism 120 includes a solid form or liquid form dispensing mechanism for dispensing one or more agents that are orally administered. In one embodiment, controllable agent-dispensing mechanism 120 includes a pill dispensing mechanism. Non-limiting examples of solid form or liquid form dispensing mechanisms include gates, doors, valves, pores, conveyor belts, etc. For example, agent-dispensing device 110 may include one or more orally administered agents, e.g., pills or oral solution, which are controllably released using a controllable agent-dispensing mechanisms, e.g., one or more electrically responsive valves. In one embodiment, the controllable agent-dispensing mechanism 120 includes one or more lids to a pill box. For example, a single lid may cover a box including segments arranged per day or time of day, the controllable agent-dispensing mechanism revealing all of the doses of medication in a single activation signal. For example, each segment of a pill box may have a separate lid that is revealed temporally or sequentially in response to one or more activation signals. Non-limiting examples of pill dispensers with controllers and/or circuitry include U.S. Patent Application 2011/0166700 and U.S. Patent Application 2013/0002795, which are incorporated herein by reference.

Agent-dispensing device 110 further includes a locking mechanism 130 coupled to controllable agent-dispensing mechanism 120 and capable of being activated or deactivated in response to providing activation signal 145 to receiver 140. Locking mechanism 130 can include any of a number of means for preventing actuation of controllable agent-dispensing mechanism 120 or release of one or more agents from agent-dispensing device 110. Non-limiting examples of locking mechanisms include camshaft-driven locking mechanism, spring loaded bar, bar/slide, retractable pin, latch, or hook which may be electrically, optically, or magnetically actuated in response to an activation signal. Non-limiting examples of dispensing devices with locking mechanism are described in U.S. Patent Application 2007/0074722 and U.S. Patent Application 2009/0276090, which are incorporated herein by reference.

Agent-dispensing device 110 further includes receiver 140. Receiver 140 is operably connected to at least one antenna and is configured to receive input signals, e.g., an activation signal sent to deactivate locking mechanism 130 to allow dispensing of the one or more agents from agent-dispensing device 110 after verifying the competency of the user. Receiver 140 can include an audio receiver, a radio receiver, an optical receiver, a magnetic receiver, an electronic receiver, or the like.

Returning to FIG. 1, system 100 includes computing device 150 including display 152 and user interface 154. Computing device 150 is able to access web-based interactive tool 160 through the Internet or other networking means to train and verify a competency of a user and to activate agent-dispensing device 110. Computing device 150 can take various forms or be part of an object, and can include, but not limited to, a computer, a laptop computer, a personal electronic device, a dedicated computing device, a limited resource computing device, a wireless communication device, a mobile wireless communication device, an electronic pen, a handheld electronic writing device, a tablet, a digital camera, a scanner, an ultrasound device, an x-ray machine, a non-invasive imaging device, a cell phone, a PDA, an electronic tablet device, a medical apparatus (implantable or otherwise), a printer, or any other like device that takes information as an input and gives it back to the end-users. Computing device 150 can include a digital single processor, ASIC, microprocessor, or other type of processor operating on a system such as a personal computer, server, a router, of other device capable of processing data including network interconnection device. In one embodiment, computing device 150 and agent-dispensing device 110 are incorporated into a single device, e.g., a smart phone with agent-dispensing capabilities.

Upon completion of training and verification of competency, an activation signal 145 is provided to receiver 140 to deactivate locking mechanism 130 to allow dispensing of one or more agents from agent-dispensing device 110. Activation signal 145 can include wired or wireless signals. For example, activation signal 145 may be carried on an electrical wire. For example, agent-dispensing device 110 can be connected to computing device 150 through an electrical connection, e.g., a wired connection, and an electrical signal sent to deactivate locking mechanism 130 on agent-dispensing device to allow dispensing of one or more agents following verification of competency of the user. For example, activation signal 145 may be carried on wireless radio waves. Activation signal 145 can include signals carried as electromagnetic waves, e.g., radio waves, microwave, infrared, or optical. For example, computing device can include a built-in wireless transmitter or accept a wireless adaptor for translating information, e.g., an activation signal, into a radio signal that is wirelessly transmitted and received by receiver 140 of agent-dispensing device 110. In one embodiment, activation signal 145 can include magnetic signals. In one embodiment, activation signal 145 can include electrical signals. In one embodiment, activation signal 145 can include an acoustic signal. Non-limiting examples of dispensing devices with communication links to a computing device are described in U.S. Patent Application 2009/0074262 and U.S. Patent Application 2008/0114299, which are incorporated herein by reference.

In one embodiment, activation signal 145 is indirectly provided to receiver 140 of agent-dispensing device 110. For example, activation signal 145 may be provided to receiver 140 in response to entering an activation code provided to the user following training and verification. For example, activation signal 145 may be provided to receiver 145 in response to scanning or capturing an image of a code, e.g., a bar code or QR code, displayed on a display of the computing device following training and verification.

Computing device 150 is configured to run web-based interactive tool 160 to train and verify the competency of user 195 and to deactivate locking mechanism 130 of agent-dispensing device 110 once competency has been verified. Web-based interactive tool 160 includes one or more of text, images, audio and/or video designed to train and verify a competency of a user in the proper use of an agent-dispensing device. In one embodiment, web-based interactive tool 160 can include a series of webpages or screen shots including text, images, audio and/or video training, verification, and authorization components for authorizing use of agent-dispensing device 110 by a user. In one embodiment, each of the webpages or screen shots can be written in plain text interspersed with formatting instructions, e.g., Hypertext Markup Language (HTLM, XHTLM). For example, web-based interactive tool 160 may contain text displayed on display 152 of computing device 150 that describes the proper use and care of agent-dispensing device 110 and/or any associated agent intended for use with agent-dispensing device 110. For example, web-based interactive tool 160 may include a video stream of an actor demonstrating proper use and care of agent-dispensing device 110 and configured for viewing on display 152 of computing device 150.

In one embodiment, web-based interactive tool 160 is downloaded from the Internet directly onto computing device 150. In one embodiment, web-based interactive tool 160 is accessible on computing device 150 via cloud computing. In one embodiment, web-based interactive tool 160 is downloaded to non-transitory machine readable media, e.g., a compact disk or flash-drive, and the non-transitory machine readable media used by computing device 150 as the source of web-based interactive tool 160. In one embodiment, web-based interactive tool 160 is completely contained in a dedicated computing device operably connected to the agent-dispensing device, e.g., incorporated into the agent-dispensing device. In one embodiment, web-based interactive tool 160 is downloaded onto computing device 150 from a disk, USB drive, or other medium capable of storing and transferring a software application.

In one embodiment, web-based interactive tool 160 is run from a remote server in a location remote from the user. In one embodiment, the remote server can include a series of one or more servers in one or more locations remote from the user. In one embodiment, the remote server is a mainframe computer in a location remote from the user. The remote server can be part of a computer network, web service, cloud-based infrastructure, or the like. In one embodiment, web-based interactive tool 160 is accessed through the World Wide Web. In one embodiment, web-based interactive tool 160 can be accessed through a web browser, e.g., Google, Chrome, Firefox, Internet Explorer, or Safari. In one embodiment, web-based interactive tool 160 is accessed through a wide area network (WAN). In one embodiment, web-based interactive tool 160 is accessed through a local area network (LAN). In one embodiment, web-based interactive tool 160 is accessed through a virtual private network (VPN) for private communication with, e.g., a pharmacy, a pharmaceutical company, or medical facility that manages the web-based interactive tool and its content. In one embodiment, web-based interactive tool 160 is accessed using an Internet address, e.g., a Uniform Resource Locator (URL).

In one embodiment, web-based interactive tool 160 is accessed from a remote server associated with a government agency or organization, e.g., the Food and Drug Administration (FDA), Centers for Disease Control (CDC), or a local/state/national public health department. In one embodiment, the remote server is associated with the World Health Organization (WHO). In one embodiment, the remote server can be located at an international site, e.g., in a country distinct from the country in which the agent-dispensing device is used. For example, the remote server could be located in an industrialized/developed country, e.g., the United States or Europe and allowing access to web-based interactive tool 160 to a user in a developing country, e.g., a West African country, via the Internet, satellite phone, or other communications link. For example, the system including web-based interactive tool 160 could be used to remotely train, verify, and authorize an individual in use of an agent-dispensing device for dispensing a vaccine or other agent in a developing country.

In some embodiments, the web-based interactive tool 160 is hosted internally on an organization's server. For example, the web-based interactive tool may be accessed from a server associated with or hosted by a government agency, e.g., the FDA, the CDC, or other public health organization, a pharmaceutical company, a pharmacy, a hospital, or clinic. In some embodiments, the web-based interactive tool is hosted externally on a public or private cloud server accessible by a user through the Internet.

In one embodiment, web-based interactive tool 160 is accessed via one or more of public, community, private, or hybrid cloud computing. Non-limiting examples of service providers for public cloud applications, storage, and other resources through the Internet include Amazon AWS, Microsoft, or Google. In one embodiment, web-based interactive tool 160 is accessed through a community cloud infrastructure shared between several organizations from a specific community with common concerns (e.g., security, compliance, jurisdiction, etc.), whether managed internally or by a third-party and hosted internally or externally. In one embodiment, web-based interactive tool 160 is accessed through a private cloud infrastructure operated solely for a single organization, whether managed internally or by a third-party and hosted internally or externally. In one embodiment, web-based interactive tool 160 is accessed through a hybrid cloud composed of two or more clouds (private, community or public) that remain unique entities but are bound together.

Figure 2:
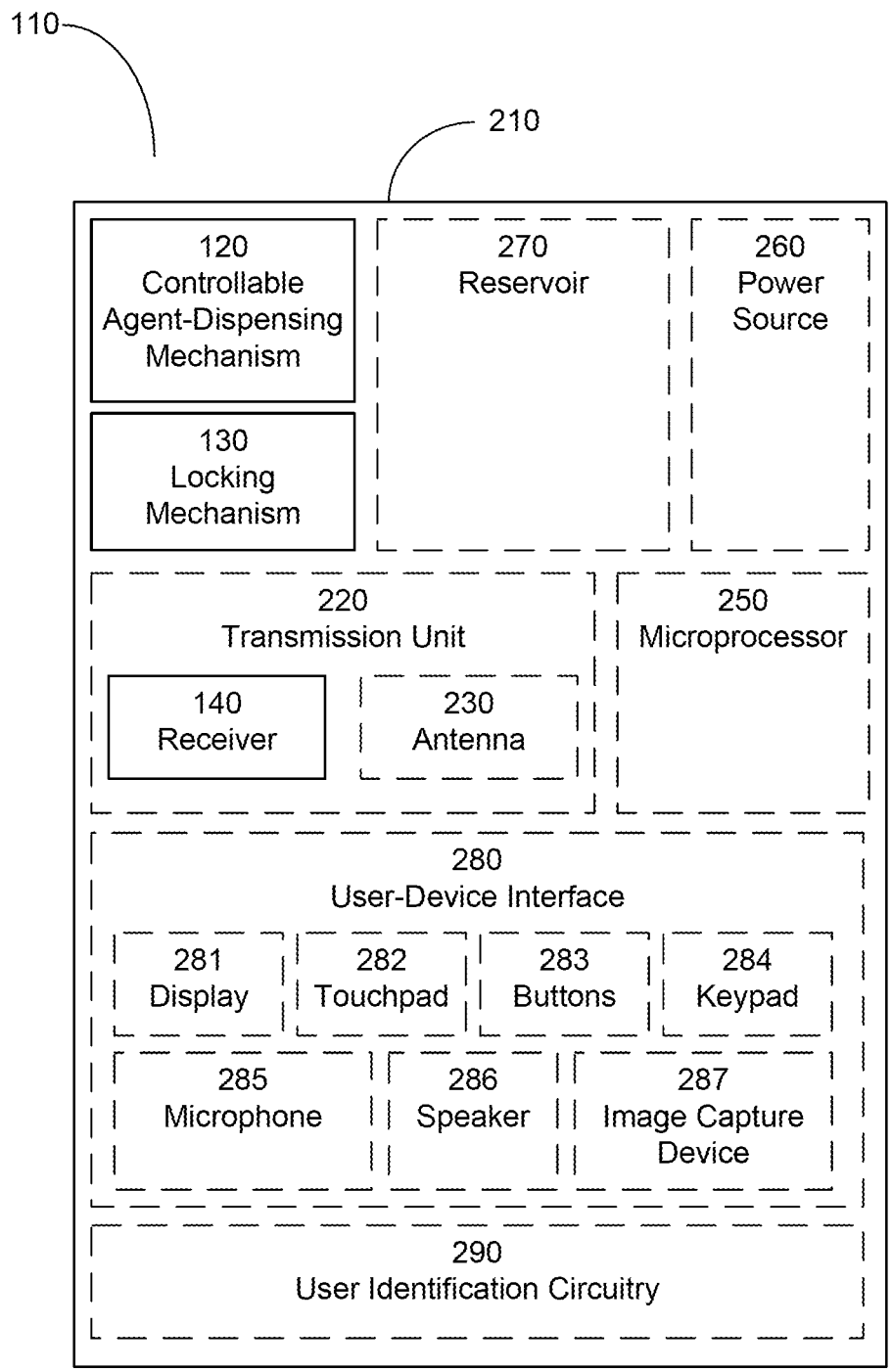
FIG. 2 is a schematic illustrating an embodiment of an agent-dispensing device.

FIG. 2 illustrates further aspects of agent-dispensing device 110. Agent-dispensing device 110 includes controllable agent-dispensing mechanism 120, locking mechanism 130, and receiver 140 in housing 210. Housing 210 can take any of a number of forms, non-limiting examples of which include a cylinder, a box, a disc, or the like. In one embodiment, housing 210 is handheld. For example, housing 210 including controllable agent-dispensing mechanism 120, locking mechanism 130, and receiver 140 may be sized for use with one or more hands. In one embodiment, housing 210 may be portable but sized for sitting on a surface. For example, housing 210 including controllable agent-dispensing mechanism 120, locking mechanism 130, and receiver 140 may be a box-like structure sized for sitting on a surface and configured to dispense one or more agents, e.g., pills, once competency of the user has been verified. Other non-limiting examples of housing types include, but are not limited to, an injector, an inhaler, a pill containing housing, a liquid containing housing, or a transdermal patch.

In one embodiment, receiver 140 is part of transmission unit 220. Transmission unit includes antenna 230 and is capable of both receiving and sending signals. For example, receiver 140 of transmission unit 220 may be configured to receive an activation signal 145 to deactivate locking mechanism 130 to allow dispensing of one or more agents through controllable agent-dispensing mechanism 120. In one embodiment, a transmitter portion of transmission unit 220 may be configured to transmit one or more signals having information regarding the status of agent-dispensing device 110, e.g., activated or inactivated, in an appropriate location, being used by an authorized user, and the like.

A "transmission unit," as used herein, can be one or more of a variety of units that are configured to send and/or receive signals, such as signals carried as electromagnetic waves. A transmission unit generally includes at least one antenna and associated circuitry. A transmission unit can include a transmitter and a receiver. A transmission unit can include volatile or non-volatile memory. A transmission unit can include a processor and/or be operably connected to a processor. A transmission unit can be operably connected to an energy source, such as a battery. A transmission unit can include an energy harvesting unit, such as a unit configured to obtain energy from electromagnetic waves. A transmission unit can include a transponder utilizing electromagnetic waves, for example as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference. A transmission unit can include an oscillator and encoder configured to generate a programmable pulse position-modulated signal in the radio frequency range (see, e.g., U.S. Pat. No. 4,384,288, which is incorporated herein by reference). A transmission unit can include a radio frequency identification device (RFID), which can be a passive RFID device, a semi-passive RFID device, or an active RFID device, depending on the embodiment (see, e.g., Chawla & Ha, "An Overview of Passive RFID," *IEEE Applications and Practice*, 11-17 (September 2007), which is incorporated herein by reference). A transmission unit including an RFID device can be configured to transmit signals in the UHF standard range. A transmission unit can include a battery-assisted passive RFID device, such as sold by Alien Technology®, Morgan Hill, Calif. A transmission unit can include an optical transmission unit. A transmission unit can include a hybrid backscatter system configured to function in an RFID, IEEE 802.11x standard and Bluetooth system (see, e.g., U.S. Pat. No. 7,215,976, which is incorporated herein by reference). A transmission unit can include a near field communication (NFC) device. A transmission unit can include a Wireless Identification and Sensing Platform (WISP) device. A transmission unit can be operably coupled to a data storage unit, for example as described in U.S. Pat. No. 7,825,776 and US Patent Application No. 2009/0243813, which are each incorporated herein by reference.

In one embodiment, agent-dispensing device 110 includes microprocessor 250. Microprocessor 250 includes circuitry configured to control one or more functions of agent-dispensing device 110 including but not limited to controlling communication between various components of agent-dispensing device 110, controlling communication with an external device or entity, e.g., computing device 150, a training device, a remote server, the Internet; and controlling response to an activation signal upon verification of a user's competency.

In one embodiment, microprocessor 250 is operably connected to power source 260 and at least one of controllable agent-dispensing mechanism 120, locking mechanism 130, and receiver 140. In one embodiment, microprocessor 250 includes central processing unit (CPU) of agent-dispensing device 110. In one embodiment, microprocessor 250 includes logic, memory and control circuitry configured to control one or more functions of one or more components of agent-dispensing device 110, e.g., controlling one or more functions of controllable agent-dispensing mechanism 120, locking mechanism 130, and/or receiver 140. In one embodiment, microprocessor 250 may be part of a microcontroller including a microprocessor, memory, clock, and I/O control. In one embodiment, microprocessor 250 includes embedded software configured to control one or more functions of agent-dispensing device 110. Non-limiting examples of dispensers with controllers are described in U.S. Patent Application 2004/0074921; U.S. Patent Application 2011/0166700; and U.S. Patent Application 2013/0002795, which are incorporated herein by reference.

Agent-dispensing device 110 optionally includes power source 260. Power source 260 may be used to power one or more components of agent-dispensing device 110, e.g., microprocessor 250, controllable agent-dispensing mechanism 120, locking mechanism 130, and receiver 140. In one embodiment, power source 260 includes nickel-cadmium, nickel-zinc, nickel-metal hydride, and/or lithium ion batteries. In one embodiment, power source 260 includes a camera or watch sized alkaline, lithium, or silver-oxide battery or other appropriately sized and powered battery. In one embodiment, the power source 260 is renewable, e.g., from solar sources, temperature differences, or vibration. In one embodiment, power source 260 includes a thin-film fuel cell such as a solid oxide type (SOFC), a solid polymer type (SPFC), a proton exchange membrane type (PEMFC), and/or substantially any combination thereof. Methods to fabricate such thin-film fuel cells are known and have been described (see, e.g., U.S. Pat. No. 7,189,471, incorporated herein by reference). In one embodiment, power source 260 includes one or more storage films that are configured for energy storage and energy conversion. Methods to fabricate such storage films are known and have been described (see, e.g., U.S. Pat. No. 7,238,628, incorporated herein by reference). In one embodiment, power source 260 is a bio-based battery (see, e.g., U.S. Pat. No. 6,994,934, incorporated herein by reference). In one embodiment, power source 260 includes thin-film batteries. Methods to fabricate thin-film batteries, including thin film microbatteries, are known and have been described (see, e.g., U.S. Pat. No. 7,194,801, which is incorporated herein by reference). In one embodiment, one or more electromagnetic receivers (not shown) are used to electromagnetically couple power to energize one or more components of agent-dispensing device 110 from an external power source. Methods to construct electromagnetic receivers have been described (see, e.g., U.S. Pat. No. 5,571,152), incorporated herein by reference.

Agent-dispensing device 110 optionally includes reservoir 270. In one embodiment, reservoir 270 is an integral part of agent-dispensing device 110 and is configured to store and dispense one or more agents. The one or more agents can include one or more agents for preventing and/or treating a disease and/or condition. The one or more agents stored in reservoir 270 can be in any of a number of physical forms, non-limiting examples of which include gas, solid, liquid, or gel form. In one embodiment, the one or more agents include solid form agents, e.g., one or more of a pill, tablet, small particles, powder, or dissolvable film.

In one embodiment, reservoir 270 can include a single storage space from which one or more agents are controllably released. For example, reservoir 270 can include a hollow space within agent-dispensing device 110 configured to store and dispense one or more tablets. For example, reservoir 270 can include a fluid reservoir configured to store and dispense multiple doses of an injectable agent, e.g., insulin. In one embodiment, reservoir 270 can include a separate storage space for each agent to be stored and dispensed. For example, reservoir 270 can include two storage spaces, a first storage space containing agent X and a second storage space containing agent Y. In one embodiment, reservoir 270 can include a plurality of storage spaces from which each dose of one or more agents is dispensed. For example, reservoir 270 may include a series of storage spaces, each storage space covered by a removable seal. In one embodiment, reservoir 270 can be configured to be refilled, e.g., having a resealable cover that can be removed by a user or other individual, e.g., a pharmacist, to refill reservoir 270 with one or more agents. Refilling reservoir 270 with one or more agents that are different from one or more agents previously stored and dispensed from the agent-dispensing device may trigger an update to what is provided to the user in the web-based interactive tool, e.g., an update to the training and verification module to reflect the new one or more agents intended for use with the agent-dispensing device.

Reservoir 270 of agent-dispensing device 110 is configured for storing and dispensing one or more agents for preventing and/or treating a disease or condition. In one embodiment, the one or more agents include one or more therapeutic agents for preventing and/or treating a disease or condition. In one embodiment, the one or more agents include one or more preventative agents for preventing and/or treating a disease or condition. Non-limiting examples of therapeutic and/or preventative agents include adrenoceptor agonists and antagonists (alpha blockers and beta blockers), cholinoceptor agonists and antagonists, antihypertensive agent, vasodilators, calcium channel blockers, sodium channel blockers, antihistamines, serotonin agonists and antagonists, ACE inhibitors, diuretics, angiotensin receptor blockers, vasoactive peptides, prostaglandins, thromboxanes, leukotriene inhibitors, nitric oxide, corticosteroids, benzodiazepines, barbiturates, antiseizure drugs, general and local anesthetics, muscle relaxants, analgesics, antipsychotics, antidepressants, anti-inflammatory agents, statins, hormones and hormone antagonists, antibacterial agents, antiviral agents, antifungal agents, and antiparasitic agents.

In one embodiment, the one or more agents include one or more vaccines. Non-limiting examples of vaccines include vaccines against small pox, hepatitis A, hepatitis B, polio, mumps, measles, rubella, diphtheria, pertussis, tetanus, haemophilus influenzae type B, chickenpox, rotavirus, influenza, meningococcal disease, pneumonia, typhoid, anthrax, yellow fever, and the like. It is anticipated that other vaccines currently in development for human immunodeficiency virus (HIV) and cancer, for example, will be of use in the systems and methods described herein.

In one embodiment, the one or more agents include one or more antidotes used to counteract the effects of a poison. Non-limiting examples of antidotes (and associated poison) include adenosine (theophylline) atropine (nerve agents, mushrooms), calcium chloride (black widow spider), chelators (heavy metals), amyl nitrite (cyanide), deferoxamine (iron), naloxone hydrochloride (opioids), and antivenom (snake and insect bites).

In one embodiment, the one or more agents include one or more controlled substances. Agents that are considered controlled substances under the Controlled Substances Act (CSA) of the Comprehensive Drug Abuse Prevention and Control Act of 1970 and codified under Title 21 Code of Federal Regulations are divided into five schedules. Schedule I Controlled Substances have no current medical use in the United States, a lack of accepted safety for use under medical supervision, and a high potential for abuse. Non-limiting examples of Schedule I Controlled Substances include heroin, lysergic acid diethylamide (LSD), marijuana, peyote, methaqualone, and 3,4-methylenedioxymethamphetamine. Schedule II Controlled Substances have a high potential for abuse, non-limiting examples of which include hydromorphone, methadone, meperidine, oxycodone, fentanyl, morphine, opium, codeine, amphetamine, methamphetamine, methylphenidate, amobarbital, glutethimide, and pentobarbital. Schedule III Controlled Substances have a potential for abuse less than substances in Schedules I and II and may lead to low or moderate physical dependence or high psychological dependence, non-limiting examples of which include low dose hydrocodone, codeine containing products, buprenorphine, benzphetamine, phendimetrazine, ketamine, and anabolic steroids. Schedule IV Controlled Substances have a low potential for abuse relative to substances in Schedule III, non-limiting examples of which include alprazolam, carisoprodol, clonazepam, clorazepate, diazepam, lorazepam, midazolam, temazepam, and triazolam. Schedule V Controlled Substances have a low potential for abuse relative to substances listed in Schedule IV and consist primarily of preparations containing limited quantities of certain narcotics, non-limiting examples of which include ezogabine and cough preparations containing not more than 200 milligrams of codeine per 100 milliliters or per 100 grams. An updated and complete list of the schedules for controlled substances is published annually in Title 21 Code of Federal Regulations (C.F.R.) §§1308.11 through 1308.15.

Agent-dispensing device optionally includes user-device interface 280. User-device interface 280 is configured to allow the user to interact with agent-dispensing device 110. In one embodiment, user-device interface 280 can be used to provide information from the device to the user. For example, user-device interface 280 can be used to display updates on the status of agent-dispensing device 110, e.g., remaining power level, dosages remaining, dispensing versus training mode, dosing schedule, cartridge currently inserted into the device, and the like. In one embodiment, user-device interface 280 can be used to provide information from the user to the device. For example, user-device interface 280 can be used to input information into agent-dispensing device such as, for example, an authorization code for use of the agent-dispensing device by an authorized user or an activation code for deactivating the locking mechanism of the agent-dispensing device. For example, user-device interface 280 can be used to input additional information including, but not limited to, user and/or patient information, a time, a date, a location, a type of agent being used, an age, a height, a weight, an activation code, and/or an authorization code.

User-device interface 280 can optionally include one or more of display 281, touchpad 282, buttons 283, keypad 284, microphone 285, speaker 286, and/or image capture device 287. For example, display 281 and/or speaker 286 can be used to transmit information, e.g., a device status update, to the user from agent-dispensing device 110. For example, display 281 can be used in combination with touchpad 282, buttons 283, and/or keypad 284 to input information into agent-dispensing device 110. In one embodiment, the user-device interface 280 can include touchpad 282 for driving and/or pointing a cursor on display 281 of agent-dispensing device 110. Similarly, microphone 285 and/or image capture device 287 can be used to input information into agent-dispensing device 110.

In one embodiment, display 281 is a type of segment display for displaying digits or alphanumeric characters, non-limiting examples of which include seven-segment displays, fourteen-segment displays, or sixteen-segment displays. In one embodiment, the segments are composed of light emitting diodes (LEDs). In one embodiment, the segments are composed of liquid crystals. For example, display 281 may include a seven-segment display incorporated LEDs for displaying numbers and/or text. For example, display 281 may display on/off indicator, time of day, doses remaining, power usage and the like. In one embodiment, display 281 is a 2-dimensional display. Non-limiting examples of technologies and/or display types include LED display, electroluminescent display, electronic paper, plasma display, liquid crystal display, organic LED display, surface-conduction electron-emitter display, carbon nanotubes, quantum dot display, field emission display, or a ferro-liquid display. A non-limiting example of an agent dispenser system with a display is described in U.S. Patent Application 2013/0002795, which is incorporated herein by reference.

In one embodiment, the user-device interface 280 can include buttons 283. In one embodiment, buttons 283 can include an "on/off" button. In one embodiment, buttons 283 can include a "mode" button for changing input modes shown on display 281. In one embodiment, buttons 283 include "up" or "down" arrows for scrolling through a menu of items displayed on display 281. In one embodiment, buttons 283 can include an "enter" button to enter in a highlighted choice from a menu of options. In one embodiment, buttons 283 can include one or more buttons associated with a keypad 284, for example spring-based buttons or virtual keys including alphanumeric keys for entering text and/or numbers into agent-dispensing device 110.

In one embodiment, user-interface device 280 can include a touchscreen associated with display 281. In one embodiment, user-interface device 280 includes a single touch or multi-touch touchscreen technology incorporated into display 281.

In one embodiment, user-interface device 280 can include an audio input device, for example microphone 285. For example, a user may input information into agent-dispensing device 110 using voice commands. Other user-interface devices include, but are not limited to a mouse, pen devices, knobs, switches, camera, fingerprint scanner, voice recognition, and the like.

Agent-dispensing device 110 can optionally include user identification circuitry 290. User identification circuitry 290 is configured to receive user identification input from user-device interface 280, compare the received user identification input with a set of stored authorized user identification inputs, and verify the user as an authorized user. Verifying the user as an authorized user can occur at any point in the process of using the agent-dispensing device. An indication that the user is not an authorized user can lead a halt to any or all functions of the agent-dispensing device, e.g., power source 260 may be shut off, receiver 140 may be shut off, or locking mechanism 130 may no long be responsive to the activation signal, preventing dispensing of any or all agents from the device. In one embodiment, user identification input can include an authorization code, e.g., a login and password, specific for the user and recognizable as an authorized user identification input. For example, the user may receive a login and/or password for authorized entry into the agent-dispensing device from a physician, pharmacist, manufacturer, or other relevant entity, the login and/or password entered into the agent-dispensing device using one or more of the user-device interfaces, e.g., display and keypad. In one embodiment, user identification input can include a biometric parameter, e.g., a fingerprint scan or facial recognition, captured by one or more user-device interface, e.g., an image capture device. In one embodiment, user identification input can include other biometric parameters including, but not limited to, voice recognition, DNA analysis, or retinal scan. User identification circuitry 290 is configured to receive user input, compare with reference input, and verify that the user is an authorized user before allowing any agent to be dispensed from the agent-dispensing device. Non-limiting examples of dispensing devices with key code or biometric identification are described in U.S. Pat. No. 7,072,738; U.S. Patent Application 2006/0130828; U.S. Patent Application 2006/0130829; U.S. Patent Application 2007/0186923; U.S. Patent Application 2008/0125724; U.S. Patent Application 2009/0276090, which are incorporated herein by reference.

Figure 3:
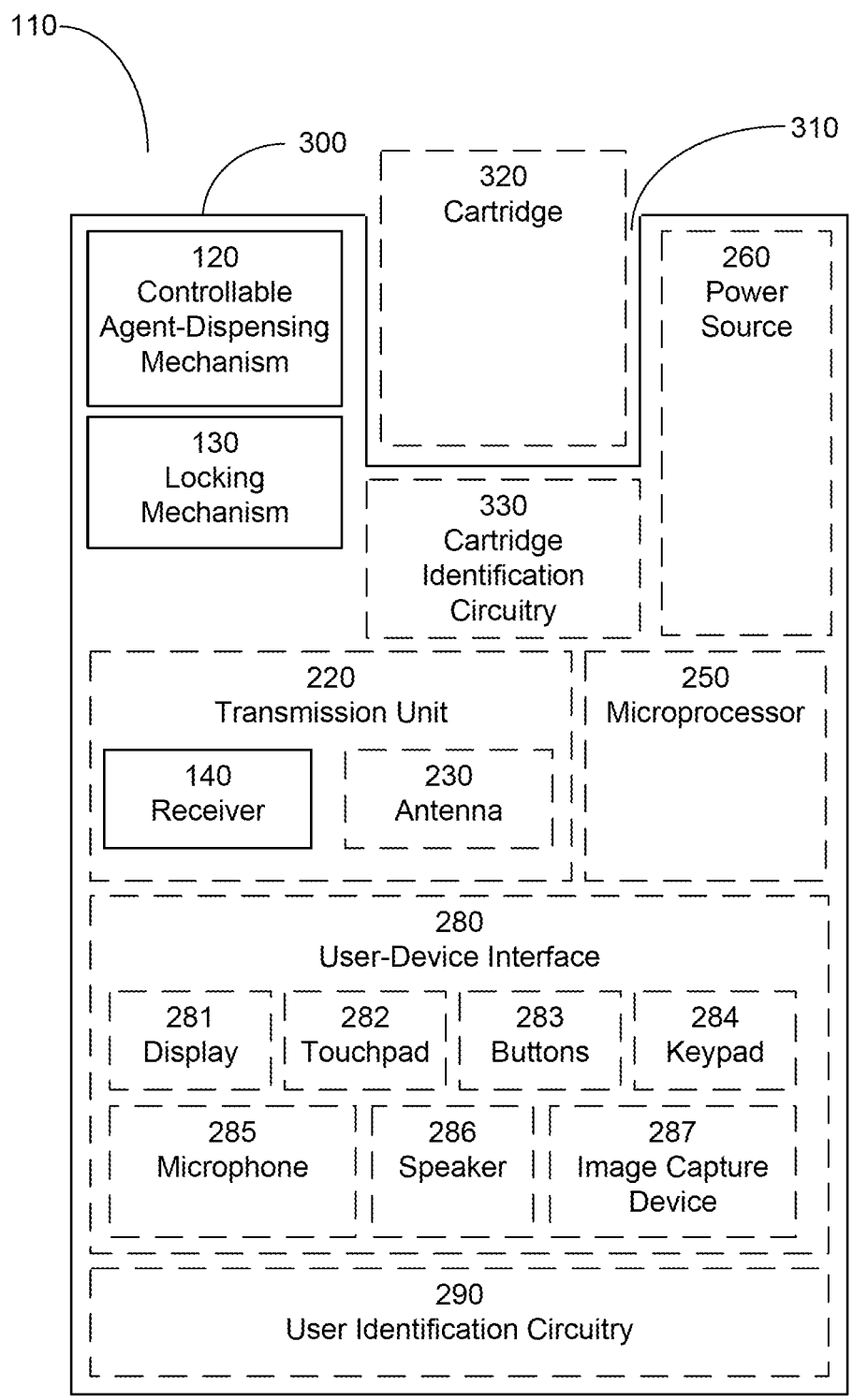
FIG. 3 is a schematic illustrating further aspects of an embodiment of an agent-dispensing device such as shown in FIG. 2.

FIG. 3 illustrates further embodiments of agent-dispensing device 110 including a replaceable reservoir. Agent-dispensing device 110 optionally includes housing 300. Housing 300 is configured in such a way as to accept a replaceable reservoir, e.g., cartridge 320. In one embodiment, housing 300 further includes docking site 310 sized for accepting at least one cartridge 320 configured for storing and dispensing one or more agents. In one embodiment, docking site 310 can include one or more receptacles or openings defined by one or more walls or surfaces of housing 300 into which at least one cartridge 320 is able to be inserted. For example, docking site 310 may include a cylindrical space configured to accommodate insertion of a cylindrical cartridge 320. For example, docking site 310 may include a rectangular space configured to accommodate insertion of a rectangular cartridge 320. In one embodiment, docking site 310 can include a male/female connector, e.g., a male portion of housing 300 configured to insert or snap into a female portion of cartridge 320. In one embodiment, the male/female connection is made at one or more outlets in the cartridge through which one or more agents contained in the cartridge will eventually be dispensed. The one or more outlets may include a seal that is broken upon forming the male/female connection. In one embodiment, docking site 310 includes a groove into which an appropriately shaped portion of cartridge 320 is able to slide and lock into place. In one embodiment, docking site 310 can include at least one magnetic surface configured to magnetically interact with at least one magnetized surface of cartridge 320. In one embodiment, a portion of docking site 310, e.g., a sharp beveled tube forming an enclosed fluid channel, may puncture an outlet into cartridge 320 upon inserting cartridge 320 into docking site 310. For example, cartridge 320 can be a vial including a septum, the septum of the vial punctured by needle-like structure associated with docking site 310.

Agent-dispensing device 110 can accommodate one or more cartridges 320. Any given cartridge 320 includes one or more agents for preventing and/or treating a disease or condition. In one embodiment, the one or more agents contained in cartridge 320 are released directly to the user from one or more controllable outlets associated with the cartridge. In one embodiment, the one or more agents contained in cartridge 320 are released indirectly to the user through agent-dispensing device 110. For example, the one or more agents may be released into agent-dispensing device 110 from cartridge 320 and subsequently controllable agent-dispensing mechanism 120 is activated to release the one or more agents from agent-dispensing device 110. In this way, the cartridge itself does not need a controllable dispensing mechanism. For example, insertion of cartridge 320 into docking site 310 may penetrate a septum associated with cartridge 320. However, it is intended that no agent is released until the agent-dispensing device is activated, e.g., after locking mechanism 130 of controllable agent-dispensing mechanism 120 is deactivated following training and verification of competency of the user. Cartridge 320 is primed to release material, e.g., a therapeutic or preventative agent, and may even release material into a holding reservoir or chamber (not shown) associated with agent-dispensing device 110 from which the material is ultimately released to the user in response to deactivation of the locking mechanism. In one embodiment, agent-dispensing device 110 may include an actuator that is activated by the activation signal and triggers opening of an outlet on the cartridge.

Cartridge 320 can include any of a number of packaging forms appropriate for storing and dispensing agents for treating and/or preventing a disease or condition. Non-limiting examples of packaging forms include one or more of a pressurized canister, glass vial with septum, blister package, other packaging with removable seals, aluminum can or bottle, antistatic bag, ampule, sachet, collapsible tube, flexible pouch, bottle, box, plastic bottle, pouch, or microchip. The one or more agents stored in cartridge 320 can be in any of a number of physical forms, non-limiting examples of which include gaseous form, solid form, liquid or gel form. In one embodiment, the one or more agents include solid form agents, e.g., one or more of a pill, tablet, small particles, powder, or dissolvable film.

Cartridge 320 is configured for storing and dispensing one or more agents for preventing and/or treating a disease or condition. In one embodiment, the one or more agents include one or more therapeutic or preventative agents for preventing and/or treating a disease or condition, non-limiting examples of which have been described above herein. In one embodiment, the one or more agents include one or more vaccines, non-limiting examples of which have been described above herein. It is anticipated that other vaccines currently in development for human immunodeficiency virus (HIV) and cancer, for example, will be of use in the systems and methods described herein. In one embodiment, the one or more agents include one or more antidotes used to counteract the effects of a poison, non-limiting examples of which have been described above herein. In one embodiment, the one or more agents include one or more controlled substances, non-limiting examples of which have been described above herein and are described in greater detail in Title 21 Code of Federal Regulations (C.F.R.) §§1308.11 through §§1308.15.

In one embodiment, cartridge 320 can include a single storage space from which one or more agents are controllably released. For example, cartridge 320 can include a replaceable canister configured to store and dispense multiple metered doses of an inhalant, e.g., the asthma medication salbuterol or the flu vaccine FluMist®. For example, cartridge 320 can include a replaceable vial configured to store and dispense multiple doses of an injectable agent, e.g., insulin. In one embodiment, cartridge 320 includes a separate storage space for each agent to be stored and dispensed. For example, cartridge 320 include two storage spaces, a first storage space containing agent X and a second storage space containing agent Y. In one embodiment, docking site 320 is configured to accept a first and second cartridge, the first cartridge configured to store and dispense at least one first agent and the second cartridge configured to store and dispense at least one second agent. In one embodiment, cartridge 320 can include a plurality of storage spaces from which each dose of one or more agents is dispensed. For example, cartridge 320 may include a series of storage spaces, each storage space covered by a removable seal. Replacing cartridge 320 with a new cartridge containing one or more agents that differ from the one or more agents in the replaced cartridge 320 may trigger an update to what is provided to the user in the web-based interactive tool, e.g., an updated training and verification module to reflect the new one or more agents intended for use with the agent-dispensing device.

In one embodiment, agent-dispensing device 110 includes cartridge identification circuitry 330 configured to read a cartridge identification code, e.g., a radiofrequency tag or bar code, associated with the inserted cartridge. The cartridge identification code can be used to identify the one or more agents contained in the cartridge and dosing information. In one embodiment, the output of the training module, e.g., the type of information and/or instructions provided to the user from the web-based interactive tool, is dependent upon the at least one cartridge configured for storing and dispensing the one or more agents. For example, agent-dispensing device 110 may be capable of accepting different types of cartridges containing different types of agents. As such, the training and verification provided to the user from the web-based interactive tool is customized to reflect the content of the cartridge, which may be determined based on the cartridge identification code.

Figure 4:
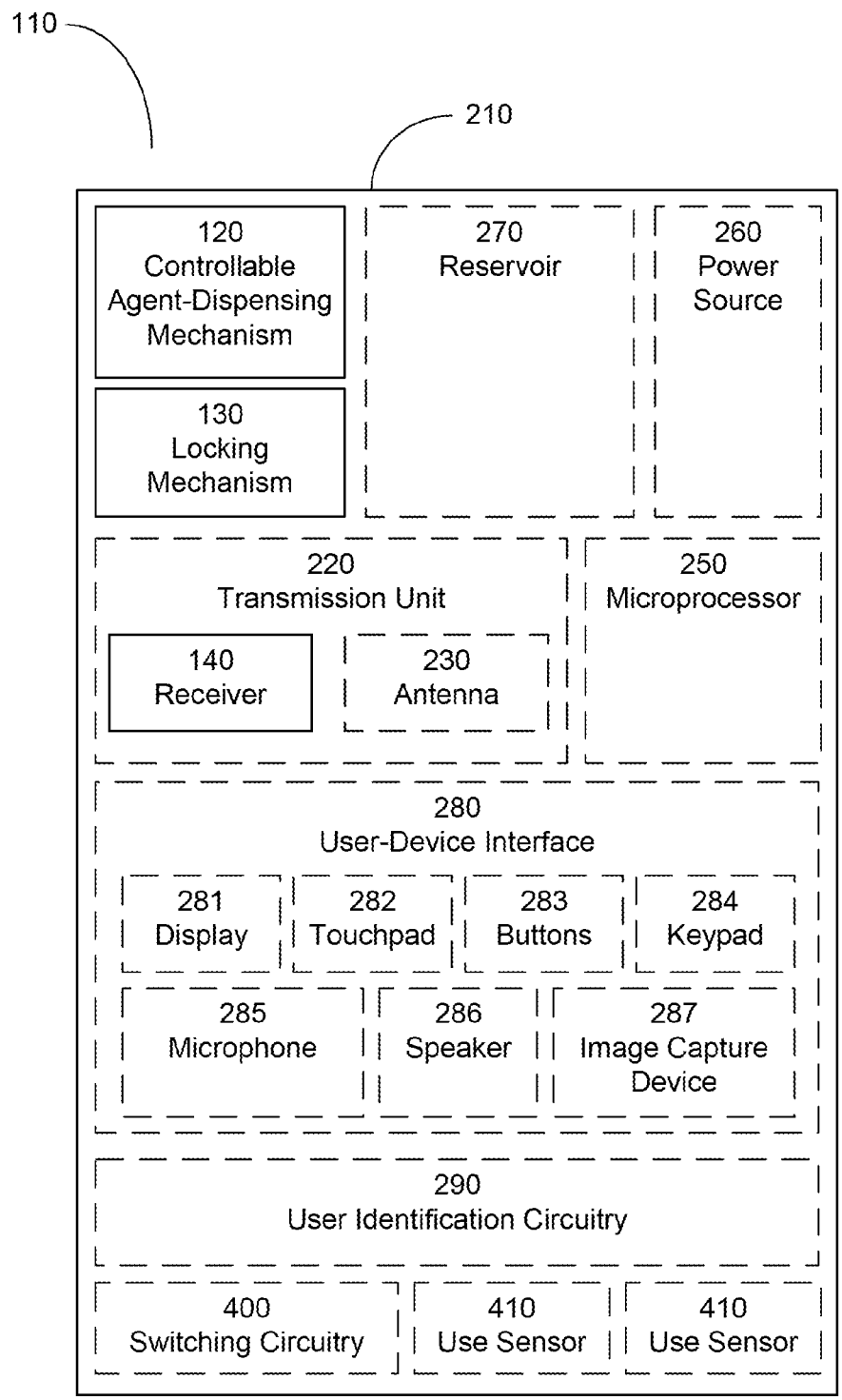
FIG. 4 is a schematic illustrating further aspects of an embodiment of an agent-dispensing device such as shown in FIG. 2.

In one embodiment, a system for competency training and use authorization for dispensing an agent includes a training device configured to simulate use of an agent dispensing device. In one embodiment, the training device is a device separate from the agent-dispensing device. See, e.g., U.S. Pat. Nos. 4,984,158; 5,431,154, which is incorporated herein by reference. In one embodiment, the training device is incorporated into the agent-dispensing device. See, e.g., U.S. Patent Application 2008/0147044, which is incorporated herein by reference. FIG. 4 illustrates further embodiments of agent-dispensing device 110 including a training component. Agent-dispensing device 110 can optionally include switching circuitry 400 configured to switch agent-dispensing device 110 from a dispensing mode to a training mode. In a dispensing mode, agent-dispensing device 110 is configured to deactivate the locking mechanism in response to a signal upon verifying the competency of the user and to respond to a trigger, e.g., pushing of a button, to activate the controllable agent-dispensing mechanism. In the training mode, agent-dispensing device 110 is configured to allow the user to proceed through all or part of the functional steps needed to administer one or more agents from agent-dispensing device 110 without actually administering any agent. In one embodiment, agent-dispensing device 110 in the training mode dispenses a placebo, e.g., a sugar pill, saline, or a puff of air. In one embodiment, agent-dispensing device 110 in the training mode has a retractable injection needle that does not penetrate the skin while in the training mode. In one embodiment, switching from dispensing mode to training mode may include locking the locking mechanism to override any activation signal until training with the device in training mode has been completed.

Agent-dispensing device 110 can optionally include one or more use sensors 410 configured to monitor the use of the agent-dispensing device in either the dispensing mode or the training mode. For example, use sensor 410 may be used to monitor one or more steps in a training protocol in the training mode. In one embodiment, use sensor 410 includes circuitry configured to monitor the proper or improper use of the agent-dispensing device while the agent-dispensing device is in at least one of a dispensing mode or a training mode. For example, use sensor 410 can include circuitry, e.g., wire connector(s), operably connected to microprocessor 250 which upon receipt of a signal from use sensor 410 instructs transmission unit 220 to send a signal to a computing device of the system to provide information to the verification module regarding the monitored one or more steps in the training protocol. The verification module of the web-based interactive tool is configured to receive at least one signal from the agent-dispensing device, the at least one signal including information regarding a proper or improper use of the agent-dispensing device acquired from the one or more use sensors. Use sensor(s) 410 can include at least one of an accelerometer, a timer, an actuator, a pressure sensor, a touch sensor, a temperature sensor, an image capture device, or an inclinometer. Other non-limiting examples of use sensors include flex sensors, flow sensors, force sensors, gas sensors, gyroscopes, image sensors, moisture sensors, motion sensors, optical sensors, temperature sensors, and vibrations sensors. In one embodiment, the use sensors are small micro electro-mechanical systems (MEMS) sized for inclusion in a handheld agent-dispensing device. In one embodiment, use sensor 410 is an accelerometer, non-limiting examples of which include piezoelectric, piezoresistive, or capacitance accelerometers, which convert mechanical motion into an electrical signal. In one embodiment, use sensor 410 is an inclinometer, non-limiting examples of which include tilt sensors, accelerometers, liquid capacitive, electrolytic, gas bubble in fluid, and pendulum. In one embodiment, use sensor 410 is a pressure or touch sensor for use in monitoring whether or not a particular component of the agent-dispensing device has been touched, e.g., a button pressed. A timing sensor(s) may be used to monitor when and in what sequence one or more buttons are pressed. In one embodiment, use sensor 410 can include a camera, charge-coupled device, or other image capture device configured to capture images of the user or parts of the user, e.g., a skin surface, while using the agent-dispensing device.

Figure 5:
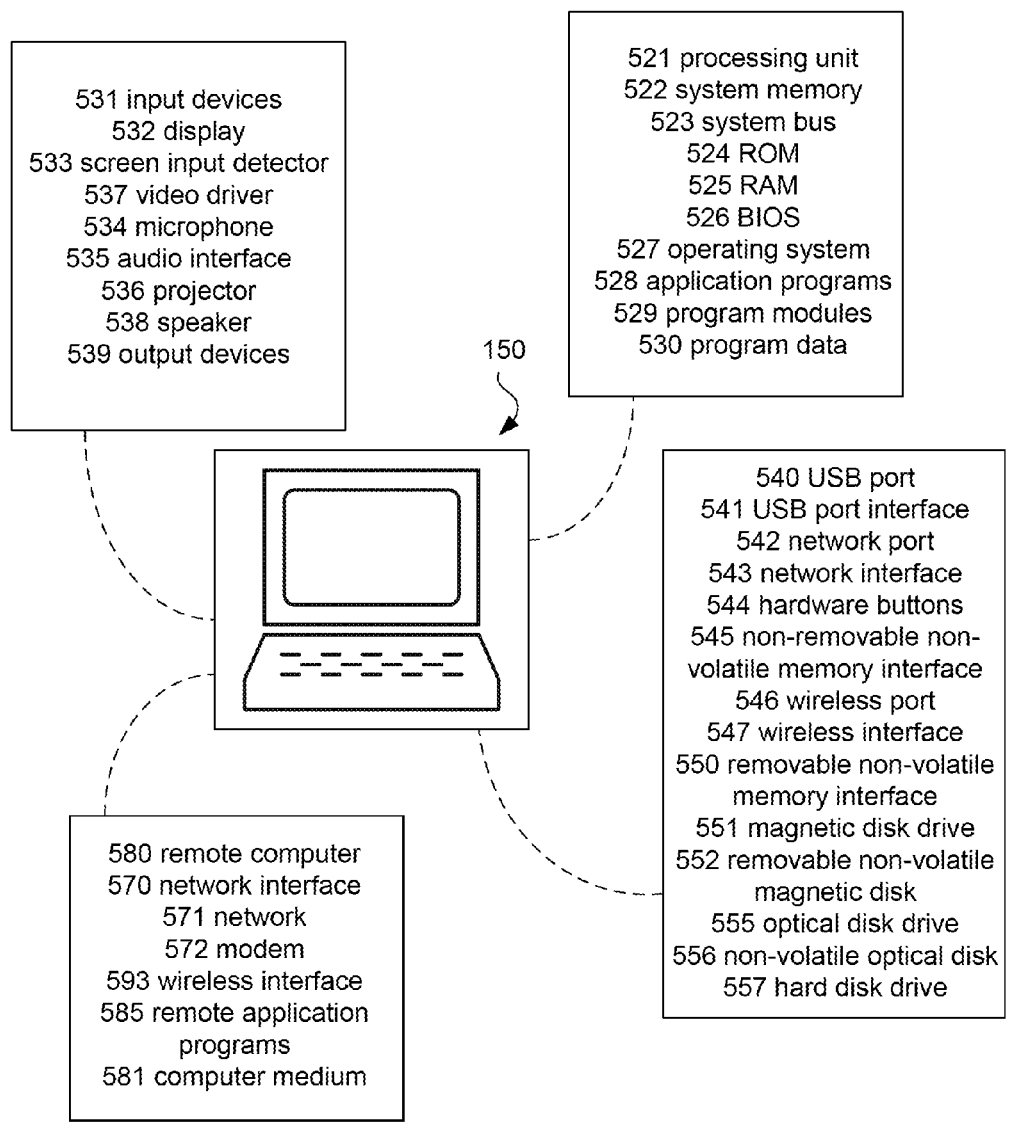
FIG. 5 is a schematic of an embodiment of a computing device.

FIG. 5 illustrates further embodiments of computing device 150 for use in a system for competency training and use authorization for dispensing an agent. Computing device 150 includes a processing unit 521, a system memory 522, and a system bus 523 that couples various system components including the system memory 522 to the processing unit 521. Processing unit 521 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In one embodiment, the computing device includes one or more ASICs having a plurality of pre-defined logic components. In one embodiment, the computing device includes one or more FPGA having a plurality of programmable logic commands.

The system bus 523 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

Computing device 150 includes a user interface, e.g., one or more input devices 531 and/or output devices 539 for use by a user to interface with the computing device and the web-based interactive tool. The one or more input devices 531 can be used to enter information into the computing device and may be integrated into the computing device or may be one or more peripheral devices operably connected through a wired or wireless connection to the computing device. Non-limiting examples of input devices 531 include a graphical user interface, a display, a keyboard, a keypad, a trackball, a joystick, a touch-screen, a mouse, a microphone, an image scanner, a digital camera, a webcam, a light pen, a bar code reader, a fingerprint scanner, a retinal scanner, a game pad, a stylus pen a switch, a dial, or the like.

The user interface may include a character, a key-based, or another user data input via a keyboard or touch sensitive display. The user interface may include using a stylus (not shown). Moreover, the user interface is not limited to an actual touch-sensitive panel arranged for directly receiving input, but may alternatively or in addition respond to another input device such as a microphone. A user may enter commands and information into the computing device 150 through user input devices, such as a number of switches and buttons, illustrated as hardware buttons 544, connected to the system via a suitable interface 545. Input devices 531 may further include a touch-sensitive display with suitable input detection circuitry, illustrated as a display 532 and screen input detector 533. The output circuitry of the touch-sensitive display 532 is connected to the system bus 523 via a video driver 537. Other input devices may include a microphone 534 connected through a suitable audio interface 535, and a physical hardware keyboard 510. Input device 531 may further include a microphone, keyboard, or pointing device, commonly referred to as a mouse, trackball, or touch pad. Other input devices may include at least one of a touch sensitive display, joystick, game pad, satellite dish, and scanner.

The user interface includes one or more output devices 539 over which processed information is viewed as output results and may be integrated into the computing device or may be one or more peripheral devices operably connected through a wired or wireless connection to the computing device. Output devices may include at least one the display 532, or a projector display 536. Non-limiting examples of output devices 539 include but are not limited to television screens, computer monitors, liquid crystal displays, audio speakers, audio headphones, and printers. In one embodiment, the computing device 150 may include at least one speaker 538 connected through a suitable audio interface 535. The one or more output devices 539 can be used to present text, images, audio and/or video content from the web-based interactive tool. In one embodiment, the input/output devices include an agent-dispensing device operably connected through a wired or wireless connection to the computing device.

In one embodiment, the one or more input/output devices are connected to the processing unit of the computing device through one or more user input interface that is coupled to the system bus, but may be connected by other interface and bus structures, such as a parallel port, game port, or a universal serial bus (USB). For example, input devices 531 or output devices 539, may be connected to the processing unit 521 through a USB port 540 and USB port interface 541, to the system bus 523. Alternatively, the other external input devices 531 and output devices 539 may be connected by other interfaces, such as a parallel port, game port or other port. The computing device 150 may further include or be capable of connecting to a flash card memory (not shown) through an appropriate connection port (not shown). The computing device 150 may further include or be capable of connecting with a network through a network port 542 and network interface 543, and through wireless port 546 and corresponding wireless interface 547 may be provided to facilitate communication with other peripheral devices, for example, the agent-dispensing device and/or a training device. It will be appreciated that the various components and connections shown are examples and other components and means of establishing communication links may be used.

In one embodiment, image-based applications such as viewers and/or toolkits (e.g., Insight Segmentation and Registration Toolkit (ITK)), are incorporated for further intake of information. In one embodiment, CAD implementations, image segmentation, or other image analysis algorithms may allow processing of images received from an image capture device.

The system memory includes read-only memory (ROM) 524 and random access memory (RAM) 525. A basic input/output system (BIOS) 526, containing the basic routines that help to transfer information between sub-components within computing device 150, such as during start-up, is stored in the ROM 524. A number of program modules may be stored in the ROM 524 or RAM 525, including an operating system 527, one or more application programs 528, other program modules 529 and program data 530.

Computing device 150 includes computer-readable media products and may include any media that can be accessed by the computing device 150 including both volatile and non-volatile media, removable and non-removable media. By way of example, and not of limitation, computer-readable media may include non-transitory signal-bearing media. By way of example, and not of limitation, computer-readable media may include computer storage media. By way of further example, and not of limitation, computer-readable media may include a communication media.

Communication media may typically embody computer-readable instructions, data structures, program modules, or other data in a modulated data signal such as a carrier wave or other transport mechanism and include any information delivery media. The term "modulated data signal" means a signal that has one or more of its characteristics set or changed in such a manner as to encode information in the signal. By way of example, and not limitation, communication media include wired media, such as a wired network and a direct-wired connection, and wireless media such as acoustic, radiofrequency, optical, and infrared media.

Computing device 150 may also include other removable/non-removable, volatile/nonvolatile computer storage media products implemented in any method or technology for storage of information such as computer-readable instructions, data structures, program modules, or other data. For example, such media includes a non-removable non-volatile memory interface (hard disk interface) 545 reads from and writes for example to non-removable, non-volatile magnetic media, or a removable non-volatile memory interface 550 that, for example, is coupled to a magnetic disk drive 551 that reads from and writes to a removable, non-volatile magnetic disk 552, or is coupled to an optical disk drive 555 that reads from and writes to a removable, non-volatile optical disk 556, such as a CD ROM. Other removable/nonremovable, volatile/non-volatile computer storage media that can be used in the example operating environment include, but are not limited to, magnetic tape cassettes, magnetic tape, magnetic disk storage, optical disk storage, memory cards, flash memory cards, DVDs, electrically erasable programmable read-only memory (EEPROM), digital video tape, solid state RAM, and solid state ROM or any other medium which can be used to store the desired information and which can be accessed by the computing device 150. The hard disk drive 557 is typically connected to the system bus 523 through a non-removable memory interface, such as the interface 545, and magnetic disk drive 551 and optical disk drive 555 are typically connected to the system bus 523 by a removable non-volatile memory interface, such as interface 550. In one embodiment, computing device 150 includes a computer-readable media drive or memory slot configured to accept non-transitory signal-bearing medium (e.g., computer-readable memory media, computer-readable recording media, or the like). In one embodiment, a computer storage media may include a group of computer storage media devices. In one embodiment, a computer storage media may include an information store. In one embodiment, an information store may include a quantum memory, a photonic quantum memory, or atomic quantum memory. Combinations of any of the above may also be included within the scope of computer-readable media.

In one embodiment, a program or set of instructions for causing a system to execute any of the disclosed methods can be stored on, for example, a computer-readable recording medium (CRMM), a non-transitory signal-bearing medium, or the like. Non-limiting examples of signal-bearing media include a recordable type medium such as magnetic tape, floppy disk, a hard disk drive, Compact Disc (CD), a Digital Video Disk (DVD), Blu-Ray Disc, digital tape, computer memory, or the like, as well as transmission type medium such as a digital and/or analog communication medium (e.g., fiber optic cable, waveguide, wired communications link, wireless communication link). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINI-DISC, non-volatile memory card, EEPROM, optical disk, optical storage, RAM, ROM, system memory, web server, cloud, or the like.

The drives and their associated computer storage media discussed above provide storage of computer-readable instructions, data structures, program modules, and other data for the computing device 150.

The computing device may operate in a networked environment using logical connections to one or more remote computers, such as a remote computer 580. The remote computer 580 may be a personal computer, a server, a router, a network PC, a peer device, or other common network node, and typically includes many or all of the elements described above relative to the computing device 150. The network logical connections include a local area network (LAN) and a wide area network (WAN), and may also include other networks such as a personal area network (PAN) (not shown). Such networking environments are commonplace in offices, enterprise-wide computer networks, intranets, and the Internet.

When used in a networking environment, the computing device is connected to the network 571 through a network interface, such as the network interface 570, the modem 572, or the wireless interface 593. The network may include a LAN network environment, or a WAN network environment, such as the Internet. In a networked environment, program modules depicted relative to the computing device 150, or portions thereof, may be stored in a remote memory storage device. By way of example, and not limitation, remote application programs 585 as residing on computer medium 581. It will be appreciated that the network connections shown are examples and other means of establishing communication link between the computers may be used.

In some embodiments, the computing device includes one or more modules optionally operable for communication with one or more input/output components that are configured to relay user output/input. In one embodiment, a module includes one or more instances of electrical, electromechanical, software-implemented, firmware-implemented, or other control devices. Such devices include one or more instances of memory, computing devices, antennas, power or other supplies, logic modules or other signaling modules, gauges or other such active or passive detection components, piezoelectric transducers, shape memory elements, micro-electro-mechanical systems (MEMS) elements, or other actuators.

In certain instances, one or more elements of the computing device 150 may be deemed not necessary and omitted. In other instances, one or more other components may be deemed necessary and added to computing device 150.

Figure 6:
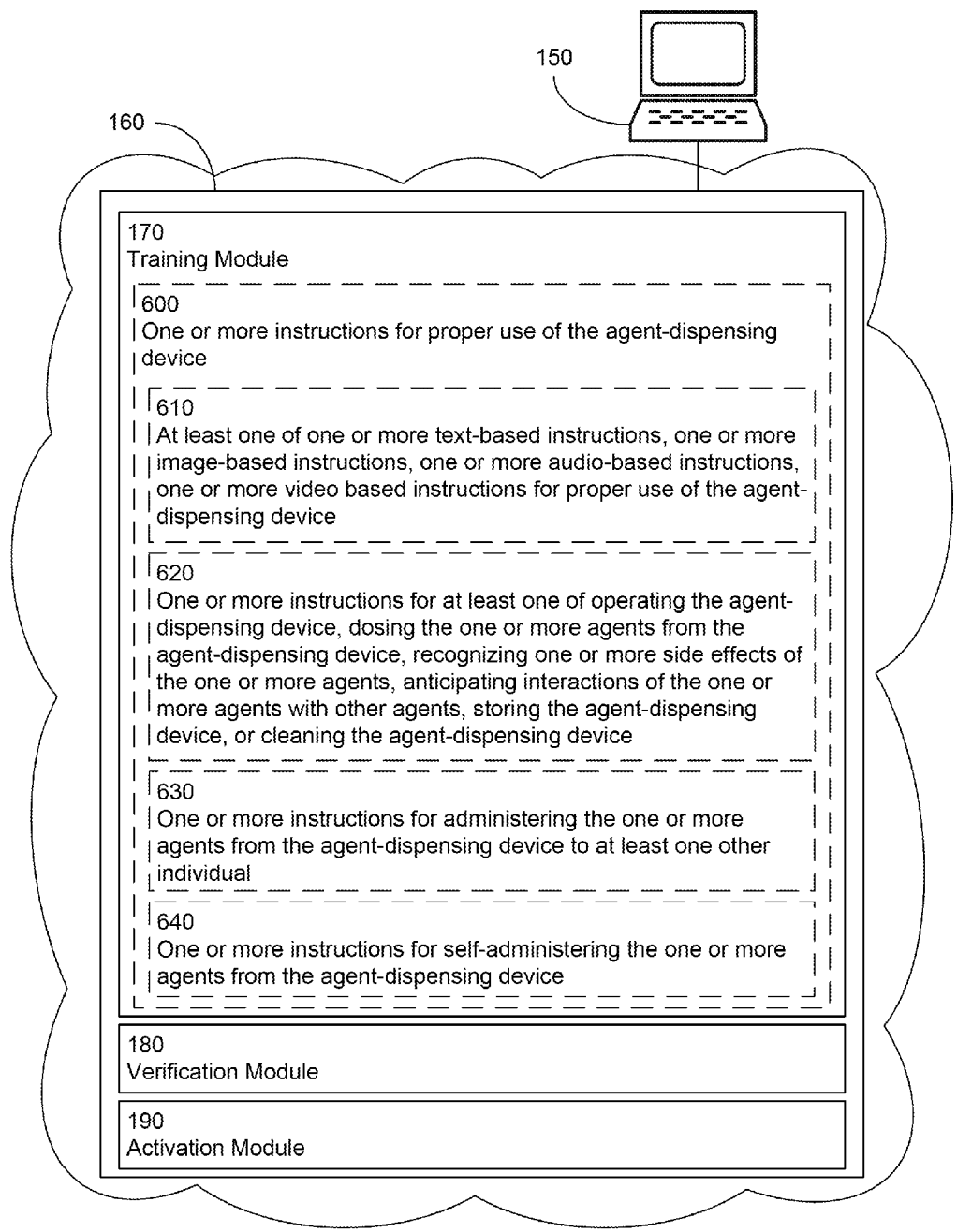
FIG. 6 is a schematic of an embodiment of a web-based interactive tool.

FIG. 6 illustrates further aspects of a system for competency training and use authorization for dispensing an agent that includes a web-based interactive tool. Web-based interactive tool 160 includes training module 170 to provide training to a user in proper use of the agent-dispensing device, verification module 180 operable to verify a competency of the user in the proper use of the agent-dispensing device, and activation module 190 responsive to verification module 180 and operable to provide an activation signal to a receiver on the agent-dispensing device to deactivate a locking mechanism to allow dispensing of one or more agents from the agent-dispensing device after verifying the competency of the user.

Training module 170 can include one or more instructions for proper use of the agent-dispensing device, as shown in block 600. The one or more instructions may be presented to the user as text, image, audio, and/or video content as part of web-based interactive tool 160. The one or more instructions can include one or more instructions for proper use of the agent-dispensing device, the one or more agents, and/or one or more associated agent-containing cartridges. The one or more instructions can include at least one of one or more text-based instructions, one or more image-based instructions, one or more audio-based instructions, and/or one or more video-based instructions, as shown in block 610.

In one embodiment, the one or more instructions include one or more text-based instructions. For example, the one or more instructions can be provided to the user a series of web-pages associated with the web-based interactive tool and including text describing proper use of the agent-dispensing device. For example, one or more text-based instructions may be presented as a word document, a slide presentation, web-based screen shots, or other means or application for displaying text on a display associated with a computing device.

In one embodiment, the one or more text-based instructions may be combined with one or more image-based instructions and/or audio-based instructions. For example, the one or more instructions may be provided to the user as a textual presentation with an audio feed reading and/or embellishing the textual presentation. For example, the one or more instructions may be provided to the user as a slide presentation, e.g., a PowerPoint presentation or a series of photos in Flickr or other image sharing application, including instructional images with one or more associated explanatory audio instructions.

In one embodiment, the one or more instructions are provided to the user as a web-based audio/video presentation with an individual(s), e.g., an actor or a medical professional, demonstrating and/or describing proper use of the agent-dispensing device. For example, the one or more instructions may be provided to the user as a video clip that includes instructions for proper use of the agent-dispensing device. For example, web-based interactive tool 160 may include an embedded audio/video presentation. For example, the audio/video presentation captured on a digital video camera can be converted to QuickTime, RealMedia, H.264, or OGG using Quick Media Converter (Microsoft, Redmond, Wash.) to allow streaming video for HTML or HTML5 web integration. For example, the audio/video presentation may be captured in H.264, Theora OGG, and WebM formats and HTML5 used for embedding. For example, the web-based interactive tool may include a link to another website, e.g., YouTube (YouTube, LLC, San Bruno, Calif.), Vimeo (New York, N.Y.), Facebook (Palo Alto, Calif.), Google Video (Mountain View, Calif.), Metacafe (Palo Alto, Calif.), or other video sharing website that hosts the audio/video instructions. In one embodiment, the audio/video instructions may include a series of narrated images using graphics interchange format (GIF) animation. In one embodiment, an embedded audio/video presentation is accessible to the user on the computing device using Windows Media® Player (from Microsoft, Redmond, Wash.) or Flash Player (from Adobe Systems Incorporated, San Jose, Calif.).

In one embodiment, training module 170 of web-based interactive tool 160 is entirely an audio presentation describing the proper use of the agent-dispensing device and/or associated agent-containing cartridge. In this regard, the audio presentation may be transmitted through one or more speakers associated with the computing device of the system. Alternatively, the audio presentation may be transmitted through a telephone, through a recording taped on an appropriate medium, e.g., a compact disc, Blu-Ray disc, or cassette tape, through a radio transmission, through an MP3 audio file, or other transmission form that allows the user to listen to the presentation.

The one or more instructions can optionally include one or more instructions for at least one of operating the agent-dispensing device, dosing the one or more agents from the agent-dispensing device, recognizing one or more side effects of the one or more agents, anticipating interactions of the one or more agents with other agents, storing the agent-dispensing device, or cleaning the agent-dispensing device as illustrated in block 620. Other non-limiting examples of instructions include instructions for proper handling and care of the agent-dispensing device, e.g., cleaning, changing batteries, and the like; proper handling and care of replaceable cartridges indicated for use with the agent-dispensing device, e.g., proper insertion into the agent-dispensing device; storage information (room temperature, chilled, or frozen, depending upon the associated one or more agent either included in the agent-dispensing device or in one or more associated replaceable cartridges); instructions for dosing, e.g., dose amount, timing of doses, schedule of doses, dosing with or without food, dosing with or without liquid, dosing with other medications, dosing with certain foods, dosing with certain nutraceuticals or herbal medicines, missed doses, and the like; instructions for monitoring adverse events, e.g., types of possible adverse events associated with a given agent, suggestions for preventing adverse events; instructions for proper use of the agent-dispensing device, e.g., how to hold the device, how to position on the surface of skin, and the like.

In one embodiment, training module 170 of web-based interactive tool 160 includes information from the prescribing information provided to the Food & Drug Administration (FDA) by a pharmaceutical company or other entity when a prescription medication or over-the-counter medication is brought to the market, non-limiting examples of which include indications and usage, dosage and administration, dosage forms and strength, contraindications, warnings and precautions, black-box warnings, adverse reactions, drug interactions, use in specific populations (e.g., pregnant or nursing women, elderly, children, male versus female, hepatic impairment, renal impairment), drug abuse and dependence (in the case of controlled substances), overdosage (e.g., symptoms and treatment), description of agent, clinical pharmacology (e.g., mechanism of action, pharmacodynamics, pharmacokinetics), nonclinical toxicology (e.g., carcinogenesis, mutagenesis, impairment of fertility), how supplied/storage and handling, and patient counseling information. As an example, see the prescribing information for morphine sulfate oral solution (from Roxane Laboratories, Inc. Columbus, Ohio), which is incorporated herein by reference.

In one embodiment, training module 170 of web-based interactive tool 160 includes text, image, audio, and/or video content including one or more instructions for administering one or more agents from the agent-dispensing device to another individual, as illustrated in block 630. The one or more agents can include one or more over-the-counter medications, prescription medications, vaccines, antimicrobials, antimalarials, or other agents configured to prevent and/or treat a disease or condition. The text, image, audio, and/or video content can include instructions for administering one or more agents from the dispensing device to another individual by inhalation, injection, transdermal, or oral administration. For example, a user, e.g., a parent, home aide, or other caregiver, at a remote distance from a medical clinic or pharmacy may receive the agent-dispensing device and any associated agent-containing cartridges in the mail or by any other delivery service. Once the agent-dispensing device is delivered, the user can access the web-based interactive tool, undergo training and verification, and activate the agent-dispensing device, all without having to travel to a medical clinic or other facility.

In one embodiment, training module 170 of web-based interactive tool 160 optionally includes text, image, audio, and/or video content including one or more instructions for self-administering one or more agents from the agent-dispensing device, as illustrated in block 640. The text, image, audio, and/or video content can include instructions for self-administering one or more agents from the dispensing device by self-inhalation, self-injection, transdermal, and oral administration. For example, an individual at a remote distance from a medical clinic or pharmacy may receive the agent-dispensing device and any associated agent-containing cartridges in the mail or by any other delivery service. Once the agent-dispensing device is received, the individual can access the web-based interactive tool, undergo training and verification, and activate the agent-dispensing device, all without having to travel to a medical clinic or other facility.

Figure 7:
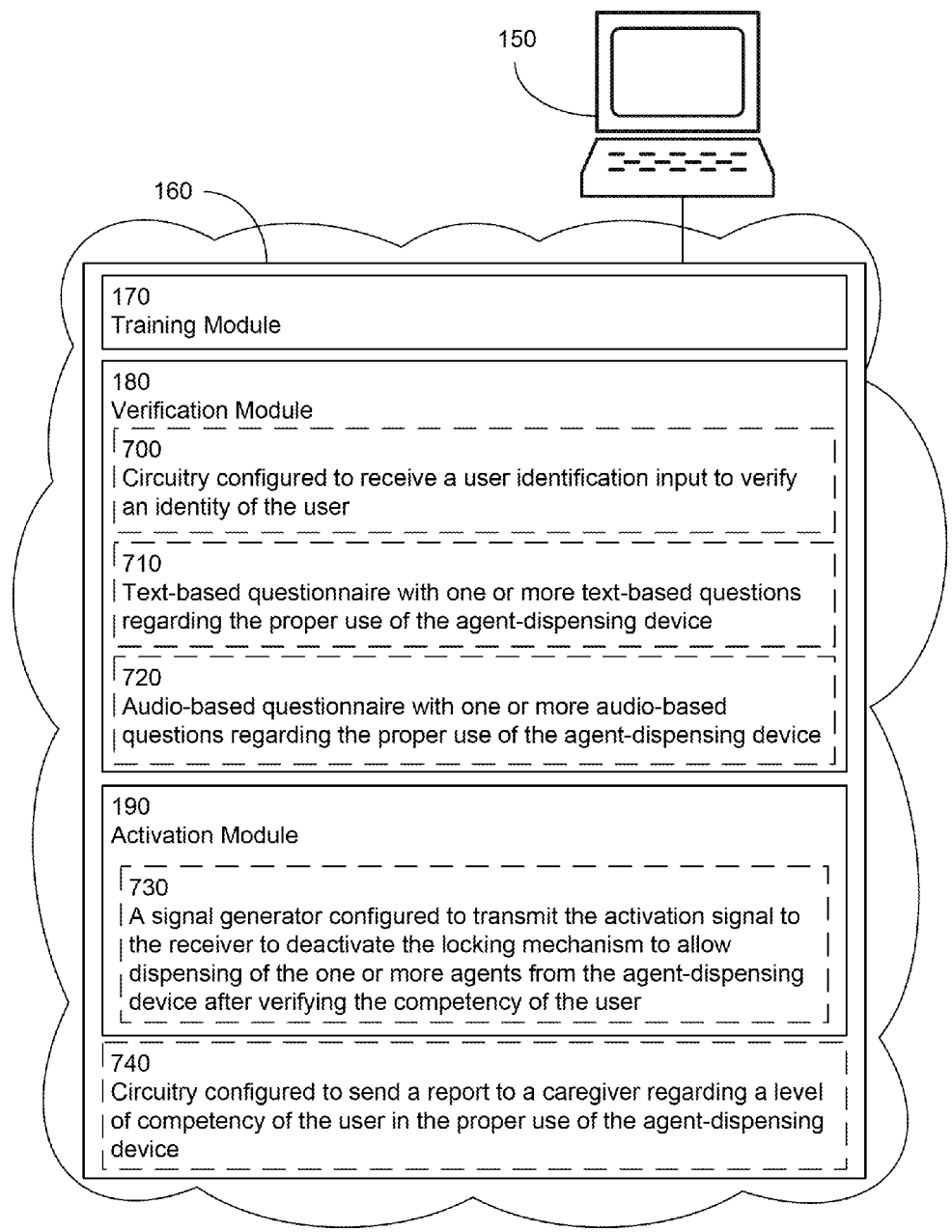
FIG. 7 is a schematic of an embodiment of a web-based interactive tool.

FIG. 7 illustrates further aspects of web-based interactive tool 160. Web-based interactive tool includes verification module 180 to verify a competency of the user in proper use of the agent-dispensing device. In one embodiment, verification module 180 includes circuitry configured to receive a user identification input to verify an identity of the user, as shown in block 700. In one embodiment, the user identification input includes an identification code that is entered into either the computing device and/or the agent-dispensing device and compared with a set of identification codes to verify an identity of the user. In one embodiment, the user identification input is one or more biometric parameter that can be entered into either the computing device and/or the agent-dispensing device and compared with a set of biometric parameters of known users to verify an identity of the user. In this way, the system knows who is being verified during the verification process. In one embodiment, the user identification input may also be an authorization code that is compared with a set of authorization codes for authorized users to verify that the user is authorized to use the agent-dispensing device and/or the web-based interactive tool.

In one embodiment, verification includes one or more means for verifying that the user is knowledgeable about the use of the agent-dispensing device and its contents. In one embodiment, verifying the knowledge of the user can include an examination, e.g., a test, e.g., a web-based multiple-choose test, either in written or oral form, for which the user must provide correct responses. In one embodiment, verification module 180 can include a text-based questionnaire with one or more text-based questions regarding the proper use of the agent-dispensing device, as shown in block 710. For example, the text-based questionnaire is provided to the user on a display of computing device 150 and the user provides responses to the text-based questionnaire using one or more of the user interfaces associated with computing device 150, e.g., a keyboard or touchpad. In one embodiment, verification module 180 can include an audio-based questionnaire with one or more audio-based questions regarding the proper use of the agent-dispensing device, as shown in block 720. For example, verification module 150 may include an audio component able to audibly project questions to the user through one or more speakers associated with computing device (or the agent-dispensing device itself) and the user provides responses to the audio-based questions by using one or more user interfaces. In one embodiment, the user may enter oral responses by speaking into a microphone associated with computing device 150. In one embodiment, the user may enter textual responses using a keyboard or touchpad. The text-based or audio-based questionnaire can include at least one of multiple choice questions, true/false questions, and/or short answer questions. The text-based or audio-based questionnaire can include one or more questions related to either the use of the agent-dispensing device itself or the one or more agents that will be dispensed from the agent-dispensing device. For example, the text-based or audio-based questionnaire can include one or more questions related to the steps required to dispense one or more agents from the device, how to store the device, how to clean the device, or how to service the device. For example, the text-based or audio-based questionnaire can include one or more questions related to the one or more agents including, but not limited to, dosing, scheduling, side effects, interactions with other agents, and the like. The user's responses to the text-based or audio-based questionnaire are used to assess the competency of the user in proper use of the agent-dispensing device. For example, the user's responses to the questionnaire may be compared with a stored set of responses and a questionnaire score assigned to the user's responses. If the user's questionnaire score meets or exceeds a pre-defined performance threshold, the user is deemed competent.

Returning to FIG. 7, web-based interactive tool 160 further includes activation module 190 responsive to verification module 180 and operable to provide an activation signal to the receiver to deactivate the locking mechanism to allow dispensing of the one or more agents from the agent-dispensing device after verifying the competency of the user. In one embodiment, activation module 190 further includes a signal generator configured to transmit the activation signal to the receiver to deactivate the locking mechanism to allow dispensing of the one more agents from the agent-dispensing device after verifying the competency of the user, as illustrated in block 730. The signal generator can include at least one of an electromagnetic signal generator, an optical signal generator, an electrical signal generator, a radio signal generator, a microwave signal generator, an acoustic signal generator, or a magnetic signal generator. In one embodiment, the signal generator generates a wired signal, e.g., an electrical current along a wire. In one embodiment, the signal generator generates a wireless signal, e.g., a radio signal.

Web-based interactive tool 160 optionally includes circuitry configured to send a report to a caregiver regarding a level of competency of the user in the proper use of the agent-dispensing device as shown in block 740. The report may be sent through either a wired or wireless telephone communication, e.g., with an audio recording or a text message. The report may be sent from computing device 150 to a caregiver's computing device, e.g., via e-mail. In one embodiment, the report can include a user's performance score on one or more of the performance modes of the verification module. For example, the report may include a performance score on a text-based or audio-based questionnaire. For example, the report may include a performance score based on analysis of captured images. For example, the report may include a performance score based on analysis of information obtained from use sensors incorporated into the agent-dispensing device. In one embodiment, the report can include images of the user using the agent-dispensing device. For example, the report may include a video stream including a user using and/or training with the agent-dispensing device. In general, a caregiver is interested in ensuring that the user is capable of administering the one or more agents either to him or her self or to one or more other individuals. Repeated reports indicating that the user has failed to meet or exceed the pre-defined performance threshold on multiple tries may indicate a need for the caregiver to contact the user in person, e.g., by phone or e-mail, to understand what the user is having difficulties with and guide them in improving performance to ensure that the one or more agents are appropriately dispensed and in a timely fashion.

Figure 8:
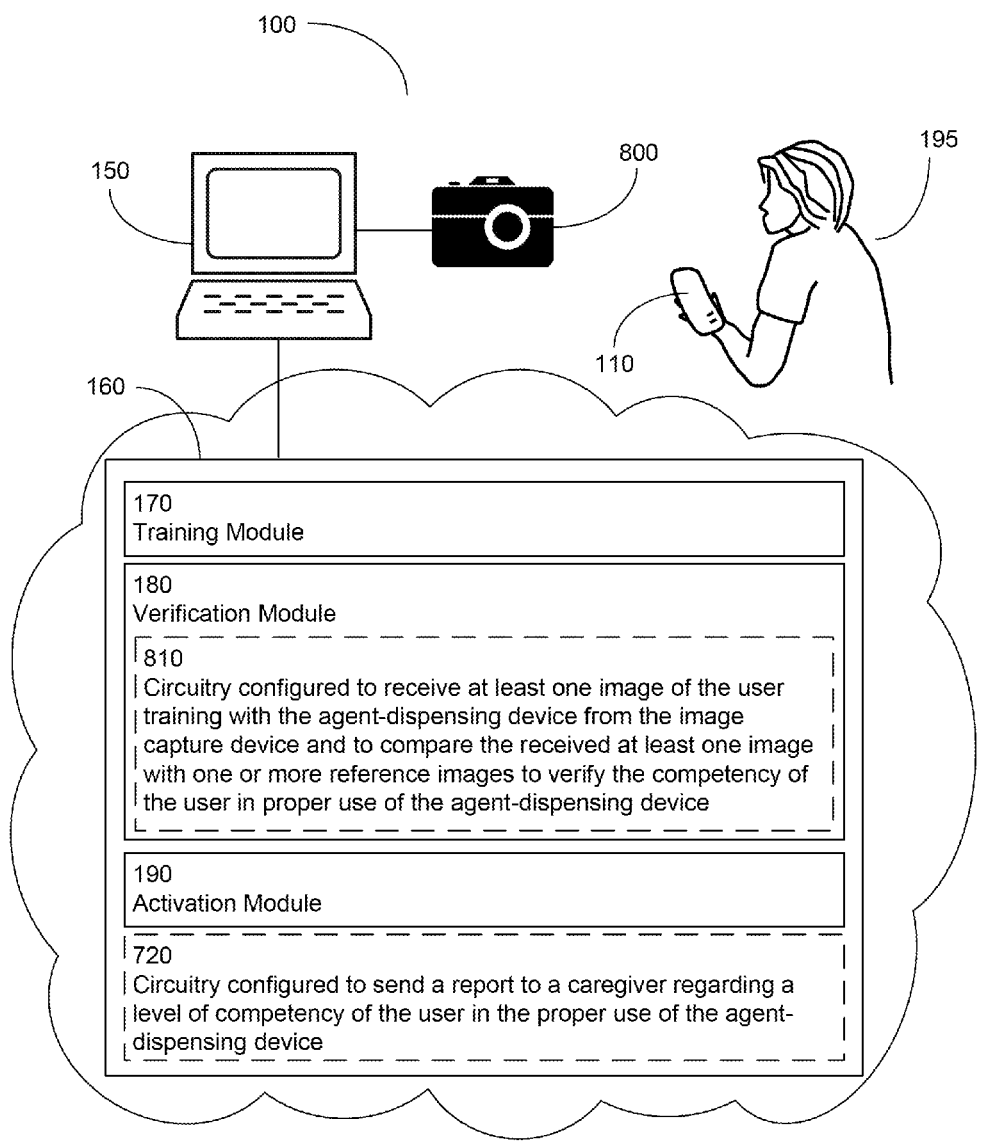
FIG. 8 is a schematic of an embodiment of a system for competency training and use authorization including an image capture device.

FIG. 8 shows further aspects of a system for competency training and use authorization for dispensing an agent. System 100 includes agent-dispensing device 110 for dispensing one or more agents to user 195. System 100 further includes computing device 150 configured to provide web-based interactive tool 160 to user 195. In one embodiment, system 100 includes image capture device 800 operably coupled to verification module 180 of web-based interactive tool 160. Image capture device 800 can include, but is not limited to, one or more passive or active scanners, digital cameras, charge-coupled device (CCD), complementary metal oxide semiconductor (CMOS), infrared sensor, or any other device or combination thereof suited to capturing an image of user 195. In one embodiment, image capture device 800 includes a motion input sensing device, e.g., a Kinect-like system (from, e.g., Microsoft, Redmond, Wash.). Image capture device 800 is further configured to transmit one or more output signals having information regarding the one or more captured digital images.

In one embodiment, verification module 180 includes circuitry configured to receive at least one image of user 195 training with agent-dispensing device 110 from image capture device 800 and to compare the received at least one image with one or more reference images to verify the competency of user 195 in proper use of agent-dispensing device 110, as illustrated in block 810. In one embodiment, the one or more reference images for use in comparing with the received at least one image of the user training with the agent-dispensing device are stored in verification module 180 of web-based interactive tool 160. In one embodiment, the one or more reference images are accessible to verification module 180 from some other source, e.g., a remote database accessed through the Internet.

In one embodiment, verification module 180 of web-based interactive tool 160 includes software components or algorithms capable of evaluating the performance/competency of the user and generates a test score. In general, the computing device is operable to detect features depicted in the captured images, e.g., physical registration landmarks, and match these features with features in the one or more reference images. Features and the relationships between them may be detected using any of a number of feature-based methods including, but not limited to, segmentation methods, distance transform, affinely invariant neighborhoods, Harris corner detection, Maximally Stable External Regions, Canny detector, Laplacian of Gaussian, elastic contour extraction, existing edge detection, line intersections, local extrema of wavelet transform, inflection points of curves, and the like. Verification module 180 is further operable to match the features detected in the one or more images with features in the one or more reference images using one or more feature-matching methods, non-limiting examples of which include Euclidean distance matching, invariant moments, nearest neighbor based matching, correlation-like methods, Fourier methods, mutual information methods, optimization methods. Further non-limiting examples include methods using spatial relations, e.g., graph matching algorithms, methods using invariant descriptors, and relaxation methods. The following references are incorporated by reference and include descriptions of computational methods for image registration: Szeliski *Foundations and Trends in Computer Graphics and Vision*, Vol. 2, No. 1 (2006) 1-104, Zitova & Flusser *Image Vision Computing* (2003) 21:977-1000. In one embodiment, verification module 180 includes algorithms for analyzing captured images for position of the agent-dispensing device relative to the user, how the agent-dispensing device is being held, how long it takes the user to dispense the agent from the agent-dispensing device, the position of the user while dispensing, and the like, and comparing with reference images or other data forms. In one embodiment, verification module 180 includes software applications for assessing images captured using a Kinect-like motion sensing input device.

In one embodiment, image capture device 800 is used to generate streaming video of the user training with the agent-dispensing device. In one embodiment, the streaming video of the user may be assessed by a third party as to the competency of the user in the proper use of the agent-dispensing device. For example, the user may proceed through a series of steps associated with proper use of the agent-dispensing device and/or associated replaceable cartridges. While the user is performing the steps, live or taped video is being captured for viewing by a third party examiner. In one embodiment, image capture device 800 is linked to a video-conferencing capability or voice-over-Internet Protocol system, e.g., SKYPE® (Microsoft, Redmond, Wash.), Google Talk (Google, Mountain View, Calif.), or similar applications, in which the user is in live video communication with a third party examiner at a remote location who generates a test score based on the performance/competency of the user.

In one embodiment, correct completion of one or more steps in a training protocol for properly using an agent-dispensing device can be monitored by one or more use sensors in the agent-dispensing device and communicated to the verification module as the user performs the steps. For example, the agent-dispensing device can include circuitry configured to record completion of a series of operational steps in the training protocol needed to properly use the agent-dispensing device. For example, a series of training protocol steps might include turning on the agent-dispensing device, inserting a cartridge in the proper orientation, priming the cartridge, inserting a portion of the agent-dispensing device to an appropriate depth in a body orifice, and pressing a "dispense" button. In one embodiment a signal is sent to the verification module containing information indicating that a particular step in the training protocol has been completed.

Figure 9:
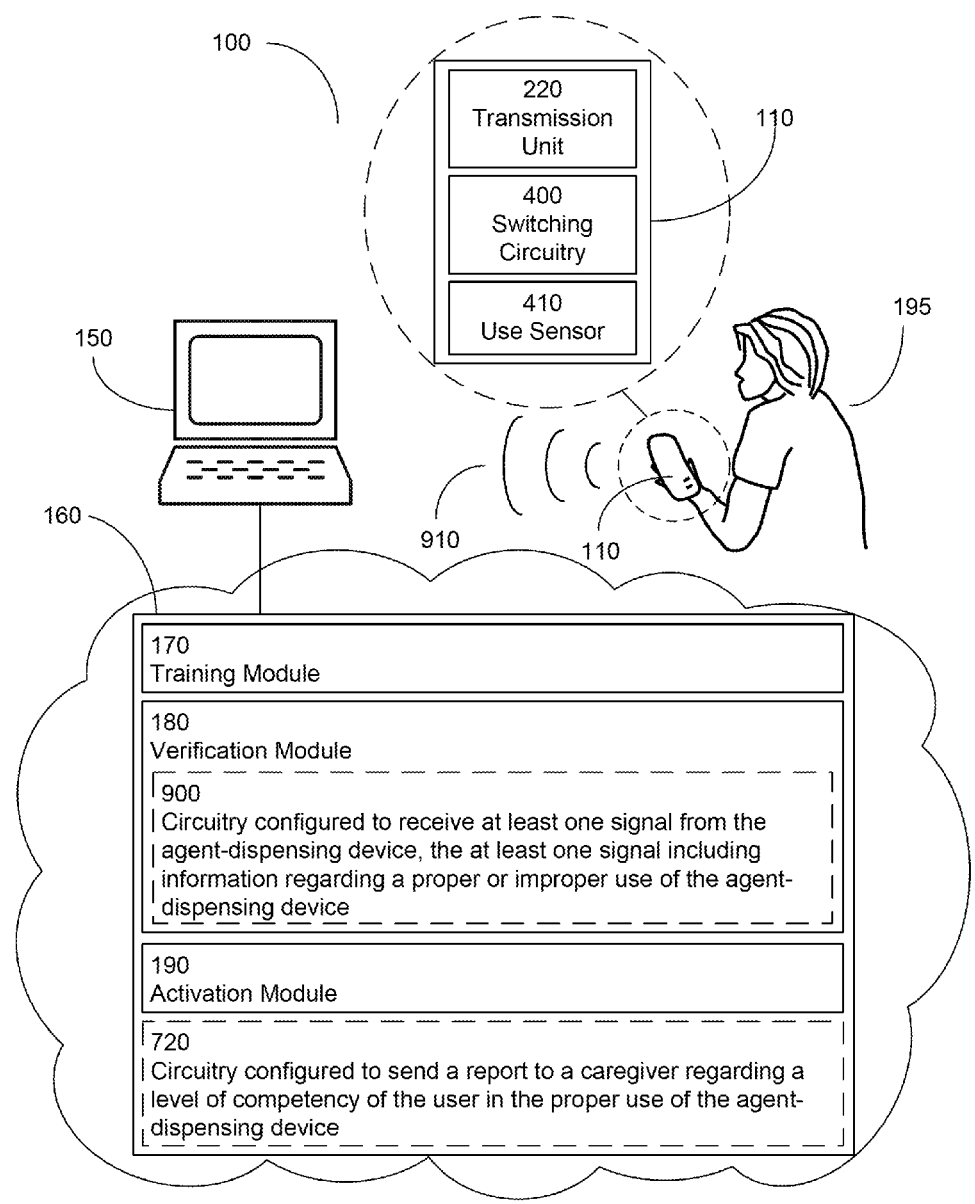
FIG. 9 is a schematic of an embodiment of a system of competency training and use authorization including use sensors on an agent-dispensing device.

FIG. 9 shows further aspects of a system for competency training and use authorization for dispensing an agent. System 100 can include agent-dispensing device 110 for dispensing one or more agents to user 195. System 100 further includes computing device 150 configured to provide web-based interactive tool 160 to user 195. Agent-dispensing device 110 can optionally include circuitry configured to transmit at least one signal 910 from agent-dispensing device 110, the at least one signal 910 including information regarding the proper or improper use of agent-dispensing device 110. Signal 910 including information regarding the proper or improper use of agent-dispensing device 110 can include either a wired or wireless transmission. Signal 910 can include an electrical signal, a radio signal, an electromagnetic signal, an acoustic signal, or an optical signal. Signal 910 can include information obtained from one or more use sensors 410 incorporated into agent-dispensing device 110 and configured to monitor proper or improper use of the device. In one embodiment, verification module 180 includes circuitry to receive at least one signal 910 from agent-dispensing device 110, the at least one signal including information regarding a proper or improper use of the agent-dispensing device, as illustrated in block 900. In one embodiment, the circuitry to receive at least one signal 910 from agent-dispensing device 110 is used to verify the competency of user 195 in the proper use of agent-dispensing device 110. In one embodiment, agent-dispensing device 110 includes switching circuitry 400 to switch agent-dispensing device 110 from a dispensing mode to a training mode. Agent-dispensing device 110 may further include one or more use sensors 410 configured to monitor proper or improper use of agent-dispensing device 110 while the device is in at least one of the dispensing mode or the training mode. The one or more use sensors 410 can include at least one of an accelerometer, a timer, an actuator, a pressure sensor, a touch sensor, a temperature sensor, an image capture device, or an inclinometer. For example, use sensor 410 that is an image capture device can be used to capture images of the user performing one or more operational steps for use of agent-dispensing device 110. For example, use sensor 410 that is a pressure sensor can be used to monitor temporal and/or spatial pressing of one or more buttons on agent-dispensing device 110. Output from the one or more use sensors, e.g., one or more signals 910 including information regarding the proper or improper use of agent-dispensing device 110, may be transmitted from transmission unit 220 back to computing device 150.

Figure 10:
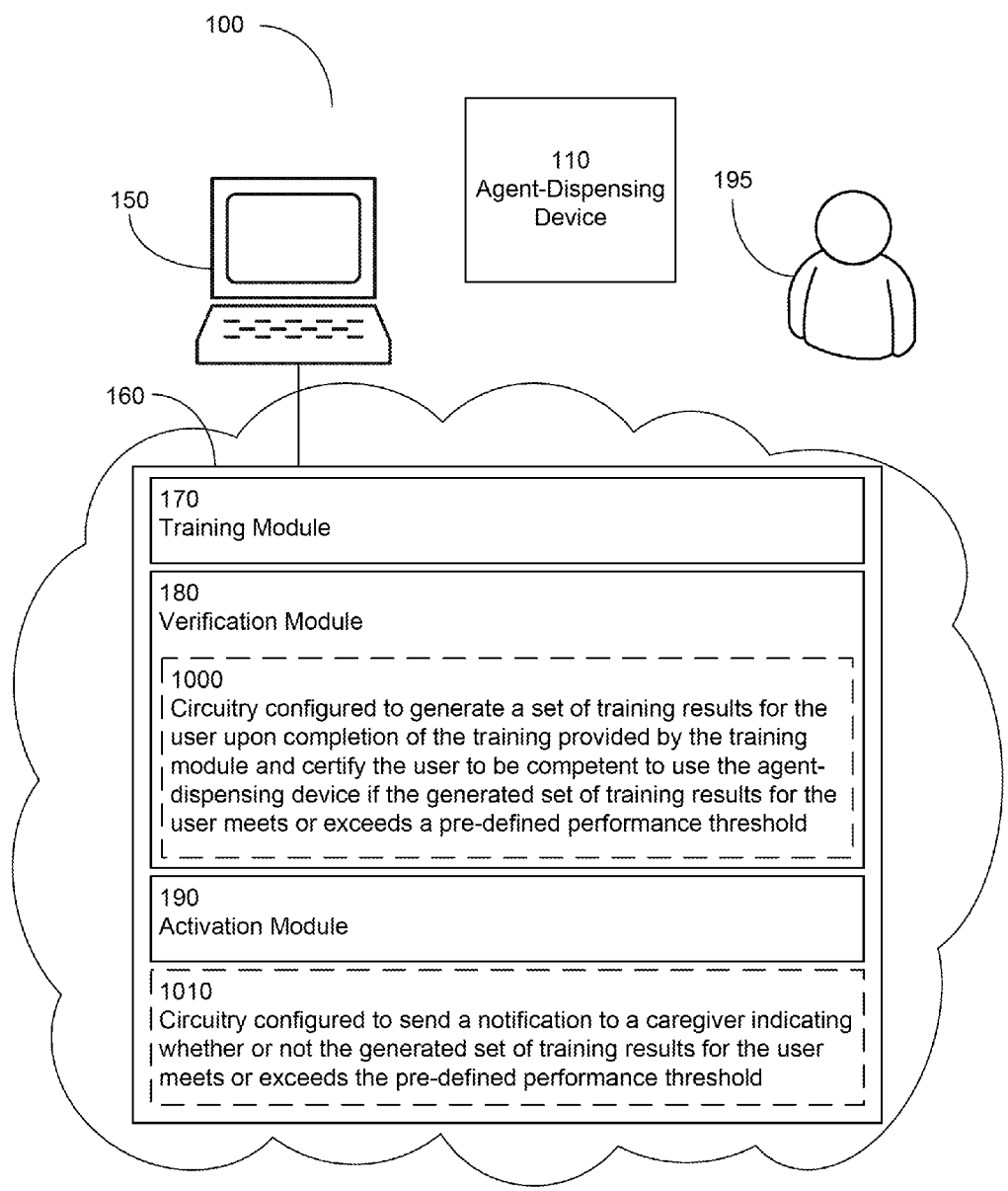
FIG. 10 is a schematic of an embodiment of a web-based interactive tool.

FIG. 10 illustrates further aspects of a system for competency training and use authorization for dispensing an agent. System 100 includes agent-dispensing device 110 for use in dispensing one or more agents to user 195. System 100 further includes computing device 150 operable to access and run web-based interactive tool 160 including training module 170, verification module 180, and activation module 190. Verification module 180 can optionally include circuitry configured to generate a set of training results for user 195 upon completion of the training provided by training module 170 and certify user 195 to be competent to use agent-dispensing device 110 if the generated set of training results for user 195 meets or exceeds a pre-defined performance threshold, as shown in block 1000. In one embodiment, the set of training results includes training results from a questionnaire, e.g., the number of questions answered correctly on a written or oral test completed using the web-based interactive tool. In one embodiment, the set of training results includes training results from image analysis comparing captured images with reference images. In one embodiment, the set of training results includes a test score provided by a third party examiner who observes the user either through live or taped video feed while the user is performing a series of competency steps or training protocol with the agent-dispensing device. In one embodiment, the set of training results is based on feedback provided by the agent-dispensing device, e.g., from one or more use sensors, while the user is using the device in a dispensing and/or training mode.

In one embodiment, the pre-defined performance threshold can include a percentage of correct responses to a text-based or audio-based questionnaire. For example, the pre-defined performance threshold may be set at 85%. For example, the pre-defined performance threshold may be set at 100%. The pre-defined performance threshold may include a training test score of up to 100%, e.g., up to 100% correct answers on a performance/competency exam. The pre-defined performance threshold may include a training test score of up to 10 on a 1 to 10 performance scale. In one embodiment, the pre-defined performance threshold may be set depending upon the type of agent-dispensing device and/or the one or more agents to be dispensed and/or the importance of the information provided to the user. For example, an agent that has a high likelihood of adverse reactions or to be addicting may have a higher pre-defined performance threshold than an agent with lower potential for side-effects or chance of addiction to ensure that the user adequately understands the risks associated with using or administering the agent prior to activating the agent-dispensing device. In one embodiment, the pre-defined performance threshold may be set based on the anticipated user, e.g., a medically trained user versus an untrained user. In one embodiment, the pre-defined performance threshold may be updated in the verification module of the web-based interactive tool to reflect a change. In general, the pre-defined performance threshold can be set by the maker of the agent-dispensing device and/or cartridges, e.g., a pharmaceutical company, the distributer of the agent-dispensing device and/or cartridges, e.g., a pharmacy, a caregiver, e.g., a doctor, nurse, aide worker, or other caregiver. The pre-defined performance threshold may be set based on the difficulty of using the dispensing device, potential harm caused by inappropriate use of the dispensing device, and/or the critical nature of the prescribing information.

Web-based interactive tool 160 can optionally include circuitry configured to send a notification to a caregiver indicating whether or not the generated set of training results for the user meets or exceeds the pre-defined performance threshold, as shown in block 1010. In general, a caregiver is interested in ensuring that the user is capable of administering the one or more agents either to him or her self or to one or more other individuals. Repeated notification indicating that the user has failed to meet or exceed the pre-defined performance threshold on multiple tries may indicate a need for the caregiver to contact the user in person, by phone, or e-mail to understand what the user is having difficulties with and guide them in improving performance to ensure that the one or more agents are appropriately dispensed and in a timely fashion.

Figure 11:
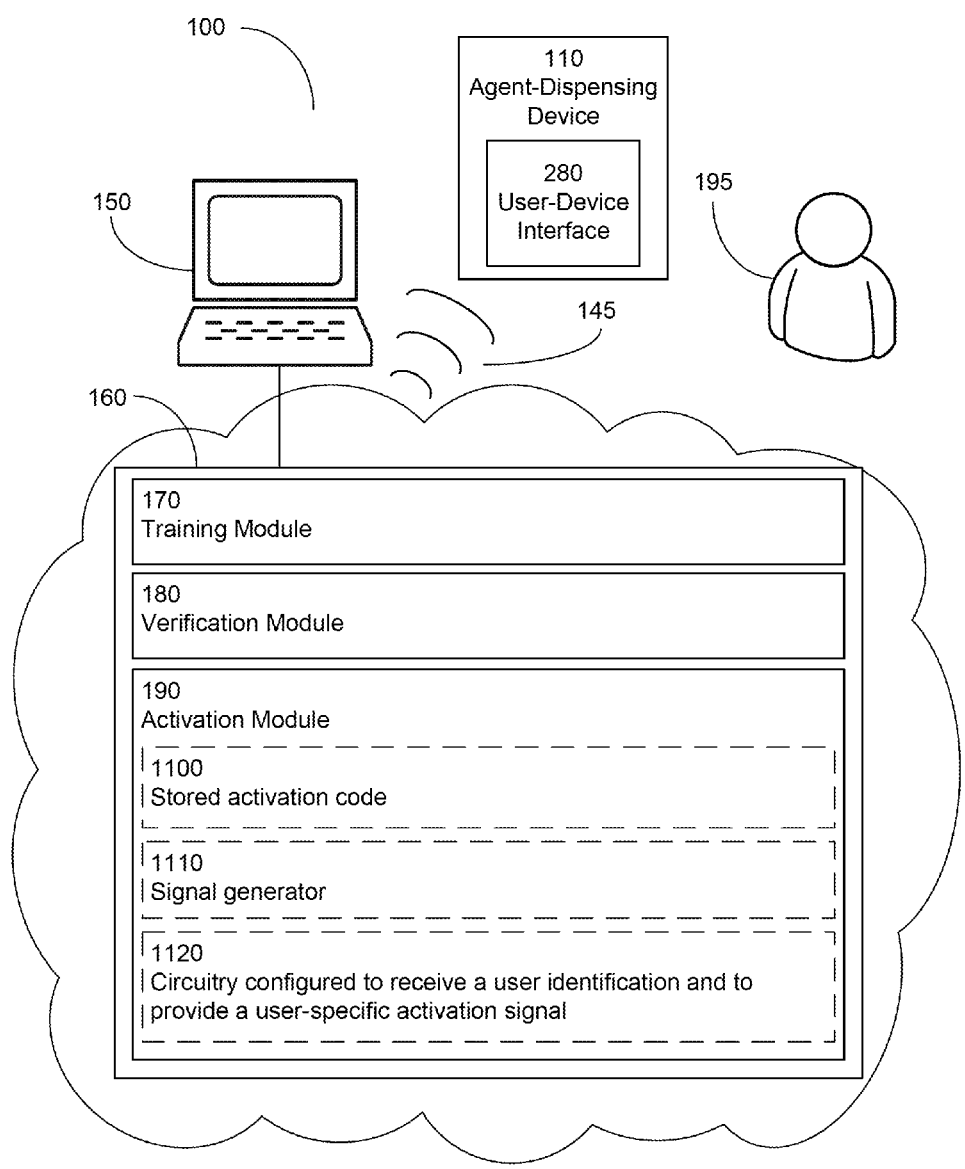
FIG. 11 is a schematic of an embodiment of a web-based interactive tool.

FIG. 11 illustrates further aspects of a system for competency training and use authorization for dispensing an agent. System 100 includes agent-dispensing device 110 for use in dispensing one or more agents to user 195. System 100 further includes computing device 150 operable to access and run web-based interactive tool 160 including training module 170, verification module 180, and activation module 190. Activation module 190 is responsive to verification module 180 and operable to provide an activation signal 145 to a receiver to deactivate a locking mechanism to allow dispensing of one or more agents from agent-dispensing device 110 after verifying the competency of user 195.

In one embodiment, activation module 190 includes a stored activation code 1100. Stored activation code 1100 can be provided to user 195 after verifying the competency of user 195 and configured to deactivate the locking mechanism when entered into agent-dispensing device 110 with a user-device interface 280. Stored activation code 1100 can include but is not limited to number code, text code, or alphanumeric code. User-device interface 280 can include, but is not limited to, a display, a speaker, a keypad, buttons, a touchpad, a microphone, or an image capture device. For example, user 195 may be provided an alphanumeric code from the activation module upon verification of competency. The user then enters the alphanumeric code into agent-dispensing device 110 either by entering the alphanumeric code on a keypad or touchpad associated with agent-dispensing device 110 or reciting the alphanumeric code into a microphone associated with agent-dispensing device 110. The alphanumeric code is interpreted by circuitry associated with the locking mechanism, e.g., compared with authorized codes, and if the entered alphanumeric code is an authorized code, the locking mechanism is deactivated to allow dispensing of the one or more agents. In one embodiment, stored activation code 1100 can include a bar code, QR code, or similar code that is displayed on the display of computing device 150 and captured by user-device interface 280, e.g., an image capture device or a bar code scanner, associated with agent-dispensing device 110. In one embodiment, the imaged or scanned code is interpreted by circuitry associated with the locking mechanism, e.g., compared with authorized codes, and if the captured code is an authorized code, the locking mechanism is deactivated to allow dispensing of the one or more agents.

In one embodiment, activation module 190 includes a signal generator 1110. Signal generator 1110 is configured to transmit activation signal 145 to the receiver to deactivate the locking mechanism to allow dispensing of the one or more agents from agent-dispensing device 110 after verifying the competency of user 195. In one embodiment, signal generator 1110 is configured to send a wired transmission, e.g., an electrical signal, along a wire connecting computing device 150 and agent dispensing device 110. In one embodiment, signal generator 1110 is configured to transmit a wireless activation signal directly to the agent-dispensing device after verifying the competency of the user. The wireless activation signal may be sent from a computing device running the web-based interactive tool to agent-dispensing device 110 through a wireless Bluetooth transmission. In one embodiment, the wireless activation signal to deactivate the locking mechanism is provided from a remote data center either through the computing device or directly to the agent-dispensing device.

In one embodiment, activation circuitry 190 further includes circuitry configured to receive a user identification and to provide a user-specific activation signal as illustrated in block 1120. The user identification can be received from the verification module in which a user identification input has been used to verify the identity of the user. In response to the identity of the user, a user-specific activation signal is transmitted. For example, if the user is identified as an authorized user, the signal will be sent. For example, if the user is not identified as an authorized user, the signal may be blocked despite the user's competency having been verified. In one embodiment, the user-specific activation signal may also be agent specific. For example, a first user may have access to agent X and agent Y while a second user may only have access to agent X and as such, the user-specific activation signal provided and the locking mechanism deactivated may reflect these differences in access.

Figure 12:
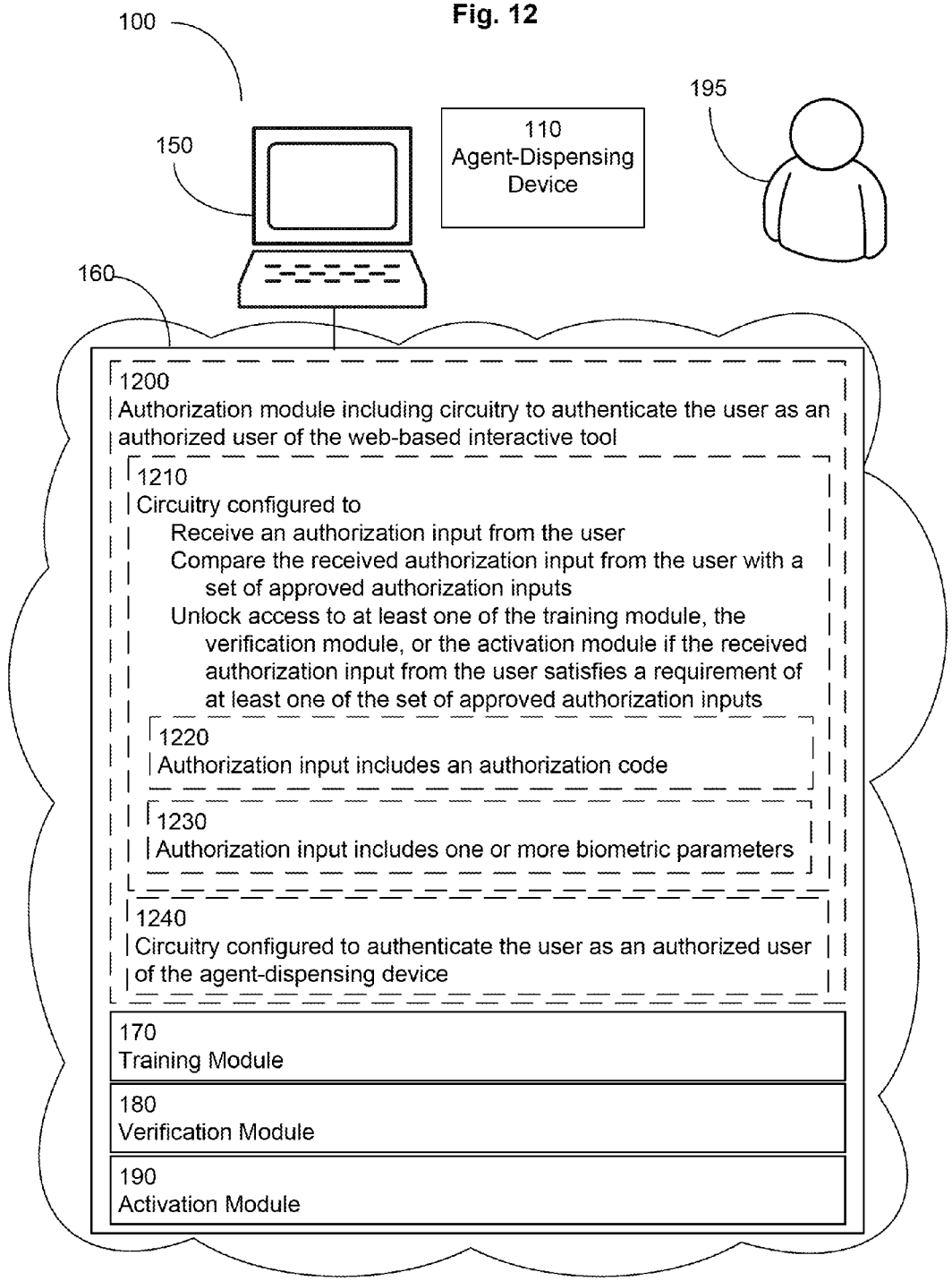
FIG. 12 is a schematic of an embodiment of a web-based interactive tool.

FIG. 12 illustrates further aspects of a system for competency training and use authorization for dispensing an agent. System 100 includes agent-dispensing device 110, computing device 150, and web-based interactive tool 160 including training module 170, verification module 180, and activation module 190. In one embodiment, web-based interactive tool 160 further includes authorization module 1200. Authorization module 1200 includes circuitry configured to authenticate user 195 as an authorized user of web-based interactive tool 160. In one embodiment, authorization module 1200 includes circuitry to authenticate user 195 as an authorized user of all or part of web-based interactive tool 160. For example, a user may be able to access the training module but only authorized users are able to access the verification and activation modules. In one embodiment, authorization module 1200 is configured to determine whether or not user 195 is authorized to access web-based interactive tool 160 to initiate training, verification, and activation for use of a particular agent-dispensing device and/or associated agent-containing cartridge. For example, authorization module 1200 may be used to allow only an authorized user to use the training and verification modules and ultimately activate agent-dispensing device 110 and as such would act as a deterrent to inappropriate and/or illegal use of the agent-dispensing device and/or associated agent-containing cartridge. In one embodiment, authorization module includes circuitry to authenticate the user as an authorized user of a specific agent-dispensing device 110 and/or associated agent-containing cartridges. For example, authorization module 1200 may be used to prevent an individual who has stolen or inappropriately obtained the agent-dispensing device and/or agent-containing cartridges from being able to use the device. For example, authorization module 1200 may be used to ensure that only competent, well-trained users are able to activate the agent-dispensing device and access the associated agents.

In one embodiment, authorization module 1200 includes circuitry to receive an authorization input from the user, compare the received authorization input from the user with a set of approved authorization inputs, and unlock access to at least one of the training module, verification module, or activation module if the received authorization input from the user satisfies a requirement of at least one of the set of approved authorization inputs, as illustrated in block 1210.

In one embodiment, the authorization input includes an authorization code 1220. Authorization code 1220 can be entered into computing device 150 to access web-based interactive tool 160. For example, web-based interactive tool 160 may include an introductory web-page that includes a space(s) for entering one or more authorization codes to gain access to other aspects of web-based interactive tool 160. In one embodiment, authorization code 1220 can include a login, e.g., a user ID name and password specific for an authorized user. In one embodiment, authorization code 1220 is provided on a smartcard, radiofrequency identification (RFID) tag, or other data form that can be "read" by computing device 150 or operably connected device to allow access to web-based interactive tool 160. In one embodiment, authorization code 1220 is provided by a physician, a pharmacist, and/or a manufacturer of the agent-dispensing device and/or agent-containing cartridge when the device is prescribed and/or purchased legally.

In one embodiment, the authorization input includes one or more biometric parameters 1230. Non-limiting examples of biometric parameters include facial recognition, voice recognition, finger prints, retinal scan, blood vessel scans, DNA, handwriting, or other means of identifying a specific user. The one or more biometric parameters provided by a user may be compared with a set of biometric parameters of authorized users using one or more comparison algorithms associated with authorization module 1200

In one embodiment, one or more biometric parameters 1230 can include facial recognition. For example, the computing device of the system may include or be operably connected to an image capture device, e.g., a video camera, which captures an image of the user and uses a facial recognition algorithm to determine whether the image of the user matches that of one of a set of authorized users (see, e.g., Phillips et al., *Proceedings of the 7$^{th}$ International conference on Automatic Face and Gesture Recognition*, FGR06, Southampton, UK, 10-12 Apr. 2006, pp. 15-24). Extensive information on facial recognition, associated algorithms, and commercial vendors can be accessed at http://www.face-rec.org/.

In one embodiment, the biometric parameter can include fingerprint recognition. For example, the computing device of the system may include or be operably connected to a fingerprint scanning or reader device and associated recognition software, which scans the fingerprint(s) of the user and determines whether the fingerprint(s) of the user matches that of one of a set of authorized users. Any of a number of examples of fingerprint readers that connect to a computing device, e.g., a personal computer or cellular phone, are commercially available (from, e.g., Zvetco Biometrics, LLC, Casselberry, Fla.; Microsoft, Redmond, Wash.). In one embodiment, the fingerprint scanner can be associated with the agent-dispensing device. A non-limiting example of a dispensing device with fingerprint identification is described in 2011/0166700, which is incorporated herein by reference.

Authorization module 1200 may further include circuitry configured to authenticate the user as an authorized user of the agent-dispensing device as shown in block 1240. In one embodiment, authorization module 1200 includes a list of authorized users of a given agent-dispensing device and/or agent-containing cartridge. The list of authorized users can be in the form of a list of names, a list of social security numbers, an authorization code, a user-specific biometric parameters, or any other property, number, or code that is specific for a given individual. If an unauthorized user is trying to use the agent-dispensing device, authorization module 1200 may further include circuitry to prevent the activation module from providing the activation signal or to prevent the agent-dispensing device from dispensing one or more agents, e.g., transmitting a signal to lock or incapacitate one or more of the functional components of the agent-dispensing device.

Figure 13:
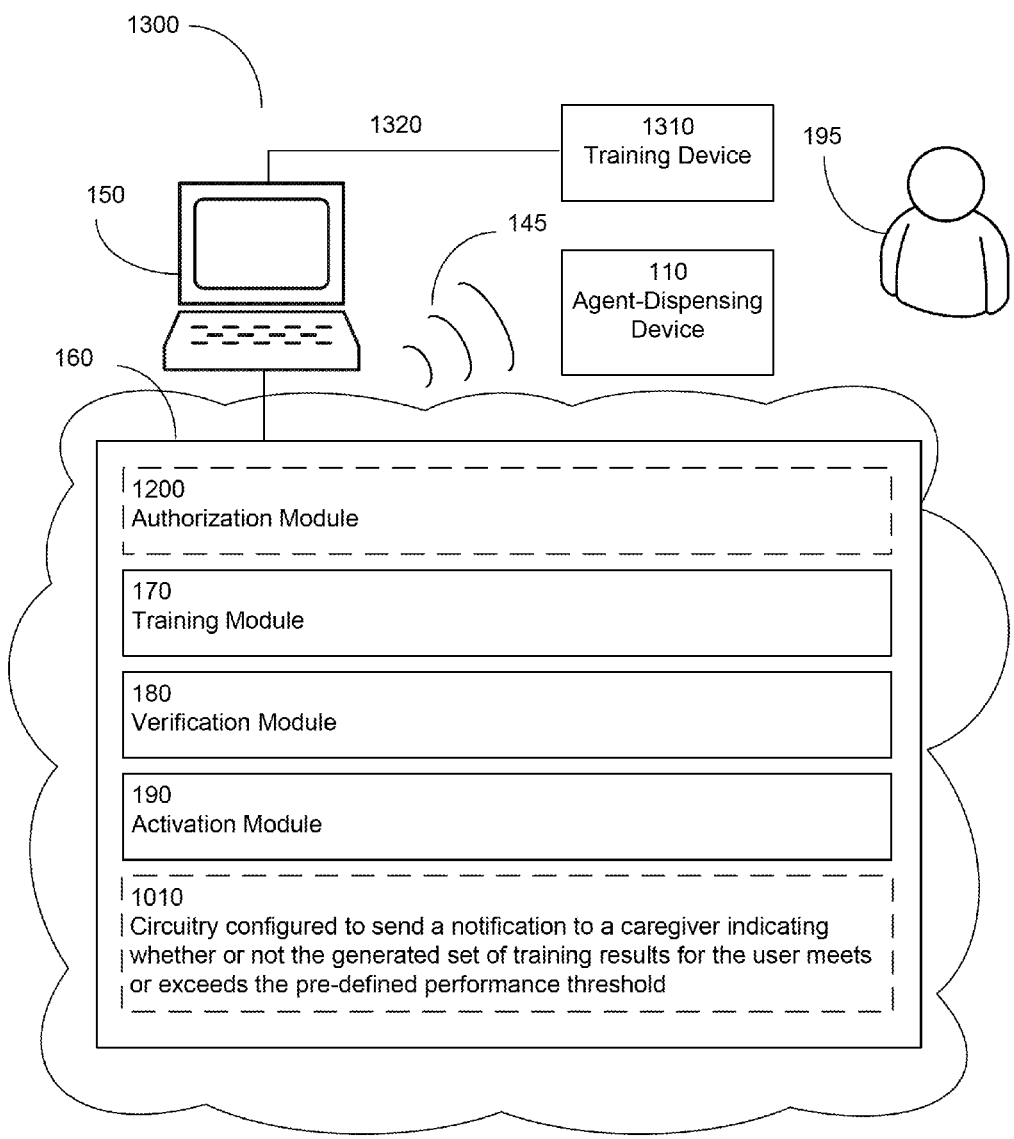
FIG. 13 is a schematic of an embodiment of a system for competency training and use authorization including a separate training device.

FIG. 13 shows a schematic of a system for competency training and use authorization for dispensing an agent that includes a training device. System 1300 includes agent-dispensing device 110, computing device 150, and web-based interactive tool 160 accessible to user 195 through computing device 150. Web-based interactive tool includes training module 170, verification module 180, activation module 190, and optionally authorization module 1200. System 1300 further includes training device 1310 which is a stand-alone device separate from agent-dispensing device 110. Training device 1310 is in communication with computing device 150 through a communication link 1320. Communication link 1320 can include at least one of a wired or wireless communication link. Training device 1310 may be used in conjunction with the training module 170 and/or verification module 180 to instruct user 195 in proper use of agent-dispensing device 110 without actually administering an agent to the user or other individual. Training device 1310 is meant to simulate all or part of the operational steps associated with dispensing one or more agents from agent-dispensing device 110 without actually dispensing an agent. For example, the training device 1310 may be used to train a user in the use of an injector device without actually injecting an agent into the skin. For example, training device 1310 may be used to train an individual in the use of an inhaler without actually inhaling an agent into the lung. See, e.g., U.S. Pat. No. 6,358,058, which is incorporated herein by reference. A commercially available example of an inhaler trainer includes 2Tone Inhaler Trainer from Dynamitech Medical, Bakersfield, Calif.

Training device 1310 may be configured to administer a placebo, e.g., water, saline, sugar pill, or sugar solution. In one embodiment, a training device that includes an injection mechanism as the means of administering an agent may or may not actually inject a needle or needles into an individual as part of the training procedure. For example, in one embodiment, the training device may be configured to inject saline as part of the training procedure.

In one embodiment, training device 1310 is configured to document whether or not the user follows a set of defined steps for using the training device and by analogy the agent-dispensing device. For example, the training device may require first loading in a cartridge in an appropriate orientation, arming the training device so that it is ready to dispense the contents of the cartridge, and place the training device in the vicinity of the appropriate delivery site, e.g., in the mouth for inhalation, on the upper arm or thigh for a single needle injection, on the abdomen for transdermal administration, and the like.

In one embodiment, use of training device 1310 by user 195 is monitored electronically. For example, a series of operational steps may be carried out by a user as part of a training protocol and the completion and accuracy of each step monitored by one or more use sensors incorporated into training device 1310. For example, training device 1310 may include a use sensor, e.g., an accelerometer, which monitors whether training device 1310 has been shaken appropriately prior to a mock administration of an agent. For example, training device 1310 may include a use sensor, e.g., a pressure sensor, which monitors whether specific buttons have been pushed in a specific sequence. Non-limiting examples of use sensors have been described above herein. In one embodiment, training device 1310 may include circuitry configured to transmit at least one signal from training device 1310 to computing device 150, the at least one signal including information regarding a proper or improper use of the training device as garnered from the one or more use sensors. Training device 1310 is in wired or wireless communication link 1320 with at least one of computing device 150 or agent-dispensing device 110. For example, information regarding the completion and accuracy of each step can be transmitted from a transmission unit incorporated in training device 1310 to computing device 150 to provide an indication as to whether the user has learned the appropriate steps and/or technique for using the training device and by analogy the actual agent-dispensing device. Non-limiting aspects of a transmission unit have been described above herein.

In one embodiment, verification module 180 of web-based interactive tool 160 includes circuitry configured to receive at least one signal from training device 1310, the at least one signal including information regarding a proper or improper use of training device 1310. Verification module 180 can further include circuitry configured to generate a set of training results for the user based on input from training device 1310 and certify that the user is competent to use the agent-dispensing device if the generated set of training results for the user meets or exceeds a pre-defined performance threshold.

In one embodiment, use of training device 1310 is monitored visually. In one embodiment, system 1300 may include an image capture device (not shown) associated with training device 1310 and/or computing device 110 for use in visually monitoring a user while using training device 1310. For example, a user may be filmed using an image capture device associated with the training device or the computing device while training with the training device and the video images compared with stored reference images or streamed back to a third party observer at a remote location for evaluation of the user's competency with the training device. In one embodiment, verification module 180 includes circuitry configured to receive at least one image of the user 195 training with training device 1310 from an image capture device and to compare the received at least one image with one or more reference images to verify the competency of user 195 in proper use of training device 1310 and by extension, competency in proper use of agent-dispensing device 110.

In one embodiment, training device 1310 includes a device that simulates a body or tissue target site and may be used in conjunction with agent-dispensing device in at least one of a dispensing mode or a training mode. For example, training device 1310 may include an injection simulator that simulates anatomical features of an injection site on a part of a subject's body, e.g., on a part of a subject's arm. See, e.g., various injection simulators available from Simulution®, Burnsville, Minn. For example, training device 1310 may include a simulator that simulates an orifice into which dispensing device is intended to be insert, for example mouth, nostrils, or portions of the urogenital tract. See, e.g., various patient and medical simulators from Simulaids, Coalville Leicestershire, UK.

Figure 14:
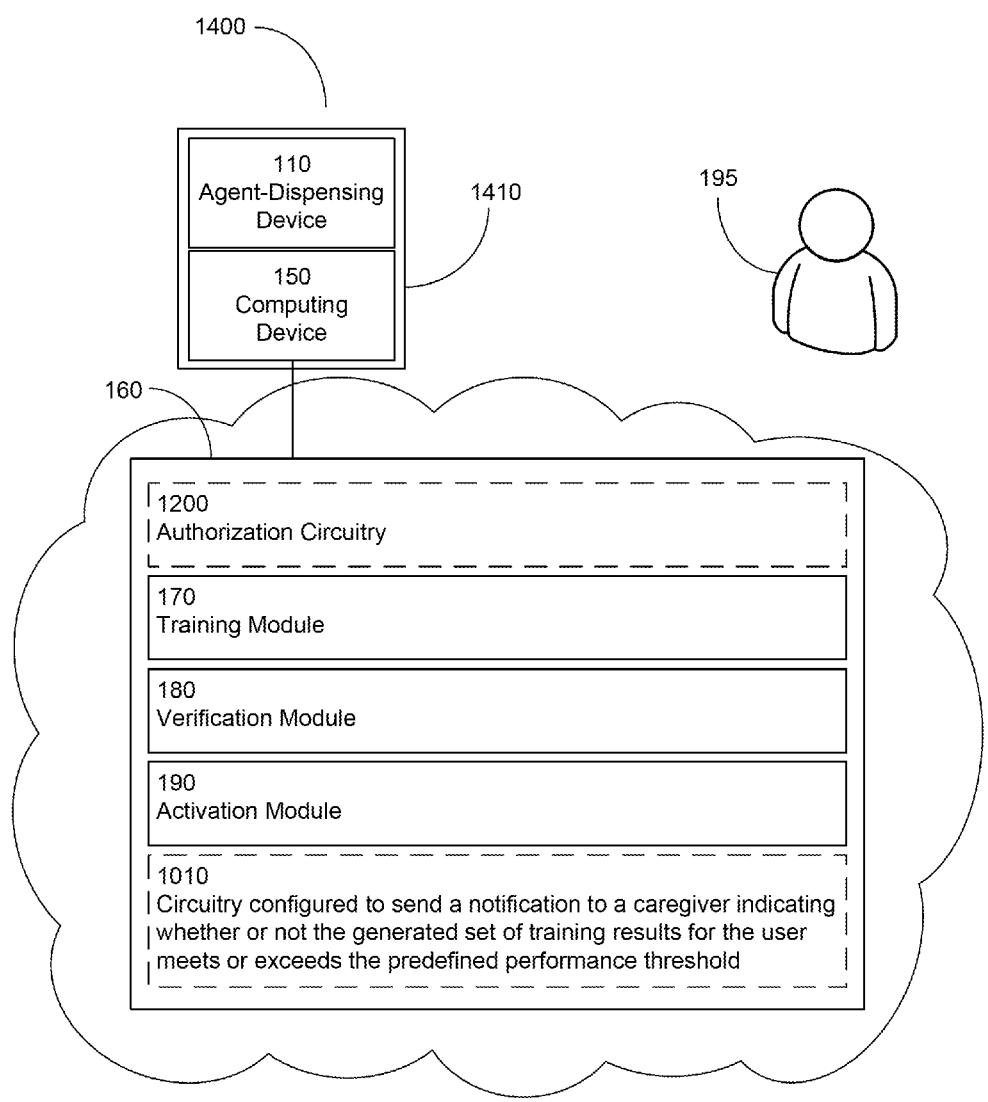
FIG. 14 is a schematic of an embodiment of a system for competency training and use authorization including a combined agent-dispensing device and computing device.

FIG. 14 shows a schematic of a system for competency training and use authorization for dispensing an agent. System 1400 includes device 1410 that includes agent-dispensing device 110 and computing device 150 in a single unit. System 1400 further includes web-based interactive tool 160 accessible to user 195 through computing device 150. Web-based interactive tool 160 includes training module 170, verification module 180, activation module 190, and optionally authorization module 1200. In one embodiment, device 1410 including combined agent-dispensing device 110 and computing device 150 is a handheld device. For example, device 1410 may include a mobile device, e.g., a mobile phone, which stores and dispenses one or more agents. In one embodiment, device 1410 is a smartphone device that includes one or more reservoirs containing one or more agents. The one or more reservoirs can be incorporated directly into the smartphone device or attachable as an accessory to a standard smartphone device. An example of a mobile phone with the capacity to store an agent, e.g., a medication, is described in U.S. Patent Application Publication 2007/0184812, which is incorporated herein by reference. For example, device 1410 may include a dedicated hand-held device, designed and operated solely for the purpose of dispensing one or more agents after training and verification. In one embodiment, device 1410 including combined agent-dispensing device 110 and computing device 150 is a desktop device. Device 1410 is configured to dispense one or more agents for preventing and/or treating a disease or condition. In general, 1410 including agent-dispensing device 110 and computing device 150 is fully capable of accessing web-based interactive tool 160, e.g., through the Internet, and progressing through training module 170, verification module 180, and activation module 190. Once user 195 has completed the training module and the verification module has verified that the user is competent to use device 1410, the activation module provides a signal to deactivate a locking mechanism to allow dispensing of one or more agents from agent-dispensing device 110. Web-based interactive tool 160 further includes circuitry configured to send a notification to a caregiver indicating whether or not a generated set of training results for the user meets or exceeds a pre-defined performance threshold, as shown in block 1010.

Further non-limiting aspects of device 1410 includes at least one of a controllable dispensing mechanism, a locking mechanism, a transmission unit including a receiver and an antenna, a power source, a user-device interface, a transmission unit including a receiver and an antenna, a microprocessor, at least one reservoir, user identification circuitry, switching circuitry, and one or more use sensors. The one or more components of agent-dispensing device 110 and the one or more components of computing device 150 of device 1410 are operably connected to one another through circuitry, e.g., electrical circuitry. Computing device 150 of device 1410 is operable to run web-based interactive tool 160. The controllable agent-dispensing mechanism of agent-dispensing device 110 is operably connected to the at least one reservoir and is configured to controllably release material in response to an activation signal. In one embodiment, the at least one reservoir is an agent-containing cartridge inserted into a receptacle associated with device 1410. In one embodiment, the at least one reservoir is an agent-containing cartridge attached to the periphery of a standard smartphone, e.g., through a USB port.

Figure 15:
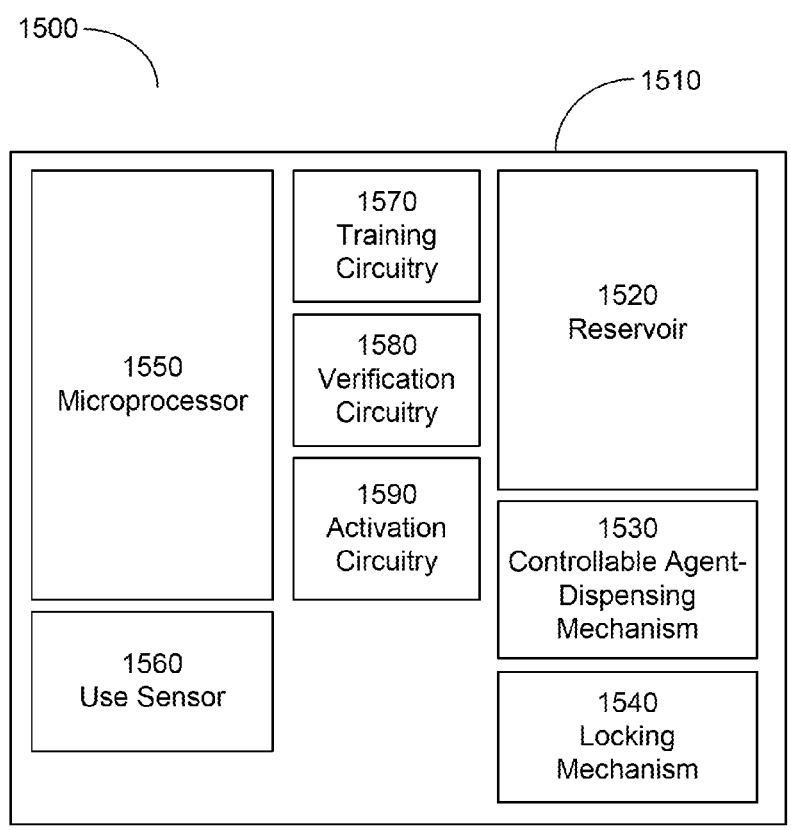
FIG. 15 is a schematic illustrating an embodiment of an agent-dispensing device.

In one embodiment, circuitry for training and verification of competency of a user prior to authorizing dispensing of one or more agents is entirely self-contained within an agent-dispensing device. FIG. 15 shows a schematic of an embodiment of an agent-dispensing device. Agent-dispensing device 1500 includes housing 1510. Housing 1510 includes at least one reservoir 1520 configured to store one or more agents for treating and/or preventing a disease and/or condition. Housing 1510 further includes controllable agent-dispensing mechanism 1530 in communication with the at least one reservoir 1520 and locking mechanism 1540 coupled to controllable agent-dispensing device 1530. Housing 1510 further includes microprocessor 1550 including circuitry configured to operate agent-dispensing device 1500 in a dispensing mode or a training mode and one or more use sensors 1560 configured to monitor at least one operational step for use of agent-dispensing device 1500 in the training mode. Agent-dispensing device 1500 further includes training circuitry 1570 configured to train the user in the at least one operational step for use of agent dispensing device 1500 and to assign a value for each of the monitored at least one operational step for use of agent-dispensing device 1500 in the training mode, verification circuitry 1580 configured to determine if the assigned value for each of the monitored at least one operational step for use of agent-dispensing device 1500 in the training mode meets or exceeds a pre-defined performance threshold, and activation circuitry 1590 responsive to verification circuitry 1580 and configured to deactivate locking mechanism 1540 to allow dispensing of the one or more agents from reservoir 1520 if the assigned value for each of the monitored at least one operational step for use of agent-dispensing device 1500 in the training mode meets or exceeds the pre-defined performance threshold.

Agent-dispensing device 1500 is configured to controllably dispense one or more agents for preventing and/or treating a disease or medical condition upon deactivating a locking mechanism of agent-dispensing device 1500 in response to verification that the user is qualified to use agent-dispensing device 1500. Non-limiting examples of diseases and/or conditions include but are not limited to cardiovascular disorders, renal disorders, metabolic disorders, neurodegenerative disorders, psychological disorders, neuromuscular and pain disorders, gastrointestinal disorders, gynecological and urological disorders, cancer, inflammation, autoimmune disorders, dermatological disorders, microbial infections and the like.

Agent-dispensing device 1500 is a self-contained device containing all of the components needed for activation and controllable release of one or more therapeutic or preventative agents after verification of the competency of the user. In one embodiment, agent-dispensing device 1500 includes housing 1510 that is sized for easy use with one or two hands, e.g., a hand-held housing. Agent-dispensing device 1500 can include one or more of an injection device, an inhalation device, a solid form dispensing device, a liquid form dispensing device, a gas form dispensing device, or a transdermal dispensing device. In one embodiment, agent-dispensing device 1500 is configured for intranasal administration of a therapeutic or preventative agent. In one embodiment, agent-dispensing device 1500 is configured for vaginal or rectal administration of a therapeutic or preventative agent. In general, agent-dispensing device 1500 can be configured to administer one or more agents to one or more of an ear, a nostril, a mouth, a throat, a lung, skin, urethra, vagina, or rectum. In one embodiment, agent-dispensing device 1500 can be a smart pill intended for oral ingestion or rectal insertion. In one embodiment, agent-dispensing device 1500 is implantable. In one embodiment, agent-dispensing device 1500 is sized for placement into either the vascular or lymphatic system.

In one embodiment, agent-dispensing device 1500 includes an inhaler device. For example, agent-dispensing device 1500 may be an inhaler, e.g., a metered dose inhaler, for use in administering an inhaled agent, e.g., a corticosteroid and/or beta-adrenoceptor agonist for treating asthma or chronic obstructive pulmonary disease.

In one embodiment, agent-dispensing device 1500 includes an injector device. For example, agent-dispensing device 1500 may be an injector with a needleless injection system, e.g., a jet-injection system, for use in administering a vaccine. An example of a jet injection system is described in Kim & Prausnitz, *Curr. Top. Microbiol. Immunol.* (2012) 351:77-112, which is incorporated herein by reference.

In one embodiment, agent-dispensing device 1500 includes an oral drug dispenser. For example, agent-dispensing device 1500 may hold one or more orally administered agents, e.g., a pill or oral solution, that are controllably released from agent-dispensing device 1500 after training, verification, and activation.

In one embodiment, agent-dispensing device 1500 includes a transdermal drug dispenser. For example, agent-dispensing device 1500 may be a transdermal patch, e.g., an iontophoretic patch, which controllably releases an agent, e.g., an analgesic agent for mitigating pain, across the dermal layer. An example of a controllable iontophoretic transdermal patch is described in Kasha et al., *Drug Discov. Ther.* (2012) 6:256-262, which is incorporated herein by reference.

Agent-dispensing device 1500 includes at least one reservoir 1520 including one or more agents for treating and/or preventing one or more disease and/or condition. In one embodiment, reservoir 1520 is an integral part of agent-dispensing device 1500 and configured to store and dispense one or more agents. The one or more agents stored in reservoir

1520 can be in any of a number of physical forms, non-limiting examples of which include gaseous form, solid form, liquid or gel form. In one embodiment, the one or more agents include solid form agents, e.g., one or more of a pill, tablet, small particles, powder, or dissolvable film.

In one embodiment, reservoir 1520 can include a single storage space from which one or more agents are controllably released. For example, reservoir 1520 can include a hollow space within agent-dispensing device 1500 configured to store and dispense one or more tablets. For example, reservoir 1520 can include a fluid reservoir configured to store and dispense multiple doses of an injectable agent, e.g., insulin. In one embodiment, reservoir 1520 can include a separate storage space for each agent to be stored and dispensed. For example, reservoir 1520 can include two storage spaces, a first storage space containing agent X and a second storage space containing agent Y. In one embodiment, reservoir 1520 can include a plurality of storage spaces from which each dose of one or more agents is dispensed. For example, reservoir 1520 may include a series of storage spaces, each storage space covered by a removable seal. In one embodiment, reservoir 1520 can be configured to be refilled, e.g., having a resealable cover that can be removed by a user or other individual, e.g., a pharmacist, to refill reservoir 1520 with one or more agents. Refilling reservoir 1520 with one or more agents that are different from one or more agents previously stored and dispensed from the agent-dispensing device may trigger an update to what is provided to the user in training circuitry 1570 and verification circuitry 1580 to reflect the new one or more agents intended for use with the agent-dispensing device.

Reservoir 1520 of agent-dispensing device 1500 is configured for storing and dispensing one or more agents for preventing and/or treating a disease or condition. In one embodiment, the one or more agents include one or more therapeutic agents. Non-limiting examples of therapeutic agents for use in an agent-dispensing device have been described above herein. In one embodiment, the one or more agents include one or more preventative agents, e.g., vaccines, non-limiting examples of which have been described above herein. It is anticipated that other vaccines currently in development for human immunodeficiency virus (HIV) and cancer, for example, will be of use in agent-dispensing device described herein. In one embodiment, the one or more agents include one or more antidotes used to counteract the effects of a poison. Non-limiting examples of antidotes have been described above herein. In one embodiment, the one or more agents include one or more controlled substances, a comprehensive list of which are described in the Controlled Substances Act (CSA) of the Comprehensive Drug Abuse Prevention and Control Act of 1970 and codified under Title 21 Code of Federal Regulations. An updated and complete list of the schedules for controlled substances is published annually in Title 21 Code of Federal Regulations (C.F.R.) §§1308.11 through 1308.15 and can be accessed at http://www.deadiversion.usdoj.gov/21cfr/cfr/2108cfrt.htm.

Agent-dispensing device 1500 includes controllable agent-dispensing mechanism 1530. Controllable agent-dispensing mechanism 1530 can include any of a number of means for dispensing a therapeutic or preventative agent for treating and/or preventing a disease and/or condition. Non-limiting examples of controllable agent-dispensing mechanisms include one or more of an inhalation mechanism, an injection mechanism, a nebulization mechanism, an intranasal mechanism, a rectal mechanism, an intravaginal mechanism, a transdermal delivery mechanism, a pill-dispensing mechanism, a solid form dispensing mechanism, a liquid form dispensing mechanism, or a gas form dispensing mechanism. Non-limiting examples of controllable agent-dispensing mechanisms have been described above herein.

Agent-dispensing device 1500 further includes locking mechanism 1540 coupled to controllable agent-dispensing mechanism 1530 and capable of being activated or deactivated through activation circuitry 1590. Locking mechanism 1540 can include any of a number of means for preventing actuation of the controllable agent-dispensing mechanism 1530 or release of agent from agent-dispensing device 1500. Non-limiting examples of locking mechanisms include camshaft-driven locking mechanism, spring loaded bar, bar/slide, retractable pin, latch, or hook which may be electrically, optically, or magnetically actuated in response to an activation signal.

Agent-dispensing device 1500 includes microprocessor 1550 including circuitry configured to operate the agent-dispensing device in a dispensing mode or a training mode. Microprocessor 1550 further includes circuitry configured to control one or more functions of agent-dispensing device 1500 including controlling communication between various components of agent-dispensing device 1500, and controlling communication between external entities and agent-dispensing device 1500. In one embodiment, microprocessor 1550 is operably linked to at least one of controllable agent-dispensing mechanism 1530, locking mechanism 1540, one or more use sensors 1560, training circuitry 1570, verification circuitry 1580, and/or activation circuitry 1590. In one embodiment, microprocessor 1550 is connected to one or more other components of agent-dispensing device 1500 through one or more wired connection, e.g., electrical connections. In one embodiment, microprocessor 1550 is connected to one or more other components of agent-dispensing device 1500 through one or more wireless connection, e.g., optical connections or electromagnetic connection. In one embodiment, microprocessor 1550 includes central processing unit (CPU) of agent-dispensing device 1500. In one embodiment, microprocessor 1550 includes logic, memory and control circuitry configured to control one or more functions of one or more components of agent-dispensing device 1500, e.g., controlling one or more functions of one of controllable agent-dispensing mechanism 1530, locking mechanism 1540, one or more use sensors 1560, training circuitry 1570, verification circuitry 1580, and/or activation circuitry 1590. In one embodiment, microprocessor 1550 may be part of a microcontroller including a microprocessor, memory, clock, and I/O control. In one embodiment, microprocessor 1550 includes embedded software configured to control one or more functions of agent-dispensing device 1500.

Agent-dispensing device 1500 includes one or more use sensors 1560. Use sensors 1560 are configured to monitor one or more steps in a training protocol associated with training a user to properly use agent-dispensing device. Use sensors 1560 are configured to monitor at least one of a series of button, keypad, or other touches, movement of the device, timing and sequence of steps performed in the training protocol, and the like. Use sensors 1360 can include one or more of an accelerometer, a timer, an actuator, a pressure sensor, a touch sensor, a temperature sensor, an image capture device, or an inclinometer, non-limiting examples of which have been described above herein.

Agent-dispensing device 1500 includes training circuitry 1570 configured to train a user in at least one operational step for use of agent-dispensing device 1500 and to assign a value for each of the monitored at least one operational step for use of the agent-dispensing device in a training mode. In one embodiment, training circuitry includes one or more instructions for proper use of agent-dispensing device 1500 including the at least one operational step for use of agent-dispensing device. The one or more instructions are accessible to the user through a user-device interface associated with agent-dispensing device 1500. Training circuitry 1570 includes circuitry for providing at least one of one or more text-based instructions, one or more image-based instructions, one or more audio-based instructions, and/or video-based instructions provided to the user through a user-device interface. In one embodiment, the one or more instructions are entirely contained within training circuitry 1570. In one embodiment, at least one of the one or more instructions is accessed by training circuitry 1570 from an external source, e.g., a website on the Internet. In one embodiment, the output from training circuitry 1570, e.g., the training instructions, is dependent upon the one or more agents stored in the at least one reservoir 1520. In one embodiment, the training instructions, e.g., one or more instructions for the at least one operational step for use of agent-dispensing device 1500, are updateable, reflecting changes in how agent-dispensing device 1500 should be used or changes in the one or more agents being dispensed from the device.

Training circuitry 1570 can provide one or more instructions regarding at least one operational step for use of agent-dispensing device 1560. Non-limiting examples of operational steps include specific buttons to push or switches to flip, a sequencing of buttons to push or switches to flip, a timing between pushing two or more buttons or flipping two or more switches, priming the device, e.g., shaking or pumping the device, cooling the device, heating the device, or moving the device in proximity to a body part, e.g., the mouth or the skin.

Training circuitry 1570 can also provide one or more instructions for at least one of operating agent-dispensing device 1500, dosing the one or more agents from agent-dispensing device 1500, recognizing one or more side effects of the one or more agents, anticipating interactions of the one or more agents with other agents, storing agent-dispensing device 1500, or cleaning agent-dispensing device 1500. Other non-limiting examples of instructions include instructions for proper handling and care of agent-dispensing device 1500, e.g., cleaning, changing batteries, and the like; proper handling and care of replaceable cartridges indicated for use with agent-dispensing device 1500, e.g., proper insertion into agent-dispensing device 1500; storage information (room temperature, chilled, or frozen, depending upon the associated one or more agent either included in agent-dispensing device 1500 or in one or more associated replaceable cartridges); instructions for dosing, e.g., dose amount, timing of doses, schedule of doses, dosing with or without food, dosing with or without liquid, dosing with other medications, dosing with certain foods, dosing with certain nutraceuticals or herbal medicines, missed doses, and the like; instructions for monitoring adverse events, e.g., types of possible adverse events associated with a given agent, suggestions for preventing adverse events; instructions for proper use of agent-dispensing device 1500, e.g., how to hold the device, how to position on the surface of skin, and the like. In one embodiment, training circuitry 1570 includes prescribing information provided to the United States Food & Drug Administration (FDA) by a pharmaceutical company or other entity bringing a prescription medication or over-the-counter medication to the market, non-limiting examples of which have been described above herein.

In one embodiment, training circuitry 1570 is configured to train a user to administer one or more agents from agent-dispensing device 1500 to another individual. For example, training circuitry 1570 can include instructions for at least one operational step to administer one or more agents from agent-dispensing device 1500 to another individual by inhalation, injection, transdermal, or oral administration. For example, a user, e.g., a parent, home aide, or other caregiver, at a remote distance from a medical clinic or pharmacy may receive the agent-dispensing device and any associated agent-containing cartridges in the mail or by any other delivery service. Once the agent-dispensing device is delivered, the user can access training on the device and undergo training and verification, and activate the agent-dispensing device, all without having to travel to a medical clinic or other facility.

In one embodiment, training circuitry 1570 is configured to train a user to self-administer one or more agents from agent-dispensing device 1500. For example, training circuitry 1570 can include instructions for at least one operational step for self-administering one or more agents from agent-dispensing device 1500 by self-inhalation, self-injection, transdermal, and oral administration. For example, an individual at a remote distance from a medical clinic or pharmacy may receive the agent-dispensing device and any associated agent-containing cartridges in the mail or by any other delivery service. Once the agent-dispensing device is received, the individual can access training on the device and undergo training and verification, and activate the agent-dispensing device.

Training circuitry 1570 is also configured to receive information from one or more use sensors 1560 incorporated into agent-dispensing device 1500. In one embodiment, a user trains with agent-dispensing device 1500 in accordance with the training instructions and at least one of the operational steps are monitored with one or more use sensors 1560. Based on feedback from use sensors 1560, training circuitry 1570 is configured to assign a value to each of the monitored at least one operational steps. For example, one or more pressure sensors can be used to monitor temporal and/or spatial pushing of one or more buttons on agent-dispensing device 1500. For example, an accelerometer and a timer can be used to determine if agent-dispensing device 1500 has been adequately shaken or primed prior to use. For example, an image capture device associated with agent-dispensing device 1500 can be used to determine whether the appropriate body part was accessed with the device, e.g., the appropriate portion of skin for an injection or placement of a transdermal patch. In one embodiment, training circuitry 1570 includes one or more algorithms for comparing one or more captured images, e.g., images of the user using the agent-dispensing device, with one or more reference images stored in a memory of the agent-dispensing device and assigns a value for each of the monitored at least one operational step based on the comparison. In one embodiment, training circuitry 1570 is configured to capture video of a user training with agent-dispensing device 1500 and to transmit the captured video an external third party examiner, e.g., via video-conferencing, who transmits back a value for each of the monitored at least one operational step for use of the agent-dispensing device, e.g., a performance score. In one embodiment, training circuitry 1570 may include a text-based or audio-based questionnaire for testing the user's knowledge regarding the use of the agent-dispensing device or the one or more agents and assigns a value based on the user's responses to the questionnaire, e.g., the number of correct answers. A user-device interface, e.g., a display, touchpad, speaker, or microphone, associated with the agent-dispensing device may be used to provide user responses to the questionnaire.

In one embodiment, correct completion of one or more steps in a training protocol for properly using an agent-dispensing device is monitored by one or more use sensors in the agent-dispensing device and communicated to the training circuitry as the user performs the steps. For example, the agent-dispensing device can include circuitry configured to record completion of a series of steps in the training protocol needed to properly use the agent-dispensing device. For example, a series of steps in a training protocol might include turning on the agent-dispensing device, inserting a cartridge in the proper orientation, priming the cartridge, inserting a portion of the agent-dispensing device to an appropriate depth in a body orifice, and pressing a "dispense" button. In one embodiment a signal is sent to the verification module containing information regarding an assigned value for each of the monitored at least one operations step for use of the agent-dispensing device.

Verification circuitry 1580 is configured to determine if the assigned value for each of the monitored at least one operational step for use of the agent-dispensing device in the training mode meets or exceeds a pre-defined performance threshold. For example, each of the monitored at least one operational step for use of the agent-dispensing device may have a score range, e.g., a score range from 0-5, with the training circuitry configured to assign a value from the score range for each of the monitored at least one operation step performed by the user in the training mode. In one embodiment, verification circuitry 1580 includes circuitry configured to receive a set of assigned values for each of the monitored at least one operational step for use of the agent-dispensing device from the training circuitry, and certify the user to be competent to use the agent-dispensing device if each of the set of assigned values for each of the monitored at least one operational step for use of the agent-dispensing device meets or exceeds the pre-defined performance threshold. For example, verification circuitry 1580 may determine if each value meets or exceeds the pre-defined performance threshold for each step, and if each value meets or exceeds the pre-defined performance threshold, the verification module verifies the competency of the user. For example, a first step may have an assigned value of 3 which meets a pre-defined performance threshold of 3, while a second step may have an assigned value of 2 which does not meet a pre-defined performance threshold of 3, and therefore the user's competency cannot be verified. In one embodiment, verification circuitry 1580 include circuitry configured to receive a set of assigned values for each of the monitored at least one operational step for use of the agent-dispensing device from the training circuitry, and certify the user to be competent to use the agent-dispensing device if the sum of the set of assigned values for each of the monitored at least one operational step for use of the agent-dispensing device meets or exceeds the pre-defined performance threshold. For example, verification circuitry 1580 may determine if the sum of each of the values meets or exceeds the pre-defined performance threshold for the sum of the steps, and if the sum of each of the values meets or exceeds the pre-defined performance threshold, the verification module verifies the competency of the user.

In one embodiment, verification circuitry 1580 is configured to receive a set of assigned values for each of the monitored at least one operational step for use of the agent-dispensing device from the training circuitry. In one embodiment, the set of assigned values includes feedback provided by the use sensors while the user trains with the agent-dispensing device in a training mode. In one embodiment, the set of assigned values includes assigned values from a questionnaire, e.g., the number of questions answered correctly on a written or oral test provided by the training circuitry. In one embodiment, the set of assigned values includes results from image analysis comparing captured images with reference images. In one embodiment, the set of assigned values includes a performance score provided by a third party examiner who observes the user either through live or taped video feed while the user is performing at least one operational step for use of the agent-dispensing device.

In one embodiment, the pre-defined performance threshold may be set at 85%. In one embodiment, the pre-defined performance threshold may be set at 100%. For example, the pre-defined performance threshold may include an assigned value of up to 10 on a 1 to 10 performance scale. The pre-defined performance threshold may include an assigned value of up to 100%, e.g., up to 100% correctly performed operational steps or answers on a performance/competency exam. In one embodiment, the pre-defined performance threshold may be set depending upon the type of agent-dispensing device and/or the one or more agents to be dispensed and/or the importance of the information provided to the user. For example, an agent that has a high likelihood of adverse reactions or to be addicting may have a higher pre-defined performance threshold than an agent with lower potential for side-effects or chance of addiction to ensure that the user adequately understands the risks associated with using or administering the agent prior to activating the agent-dispensing device. In one embodiment, the pre-defined performance threshold may be set based on the anticipated user, e.g., a medically trained user versus an untrained user. In one embodiment, the pre-defined performance threshold may be updated in the verification circuitry. In general, the pre-defined performance threshold can be set by the maker of the agent-dispensing device and/or cartridges, e.g., a pharmaceutical company, the distributer of the agent-dispensing device and/or cartridges, e.g., a pharmacy, a caregiver, e.g., a doctor, nurse, aide worker, or other caregiver. The pre-defined performance threshold may be set based on the difficulty of using the agent-dispensing device, potential harm caused by inappropriate use of the dispensing device and/or the critical nature of the prescribing information. In one embodiment, the pre-defined performance threshold is stored in a memory component of the agent-dispensing device. In one embodiment, the pre-defined performance threshold is updatable.

Agent-dispensing device 1500 further includes activation circuitry 1590 responsive to verification circuitry 1580 and configured to deactivate locking mechanism 1540 to allow dispensing of the one or more agents if the assigned value for each of the monitored at least one operational step for use of agent-dispensing device 1500 in the training mode meets or exceeds the pre-defined performance threshold. Activation circuitry 1590 is configured to provide an activation signal to deactivate the locking mechanism to allow dispensing of the one or more agents from the agent-dispensing device after verifying the competency of the user. The activation signal can include at least one of an electromagnetic signal, an optical signal, an electrical signal, a radio signal, a microwave signal, an acoustic signal, or a magnetic signal.

Figure 16:
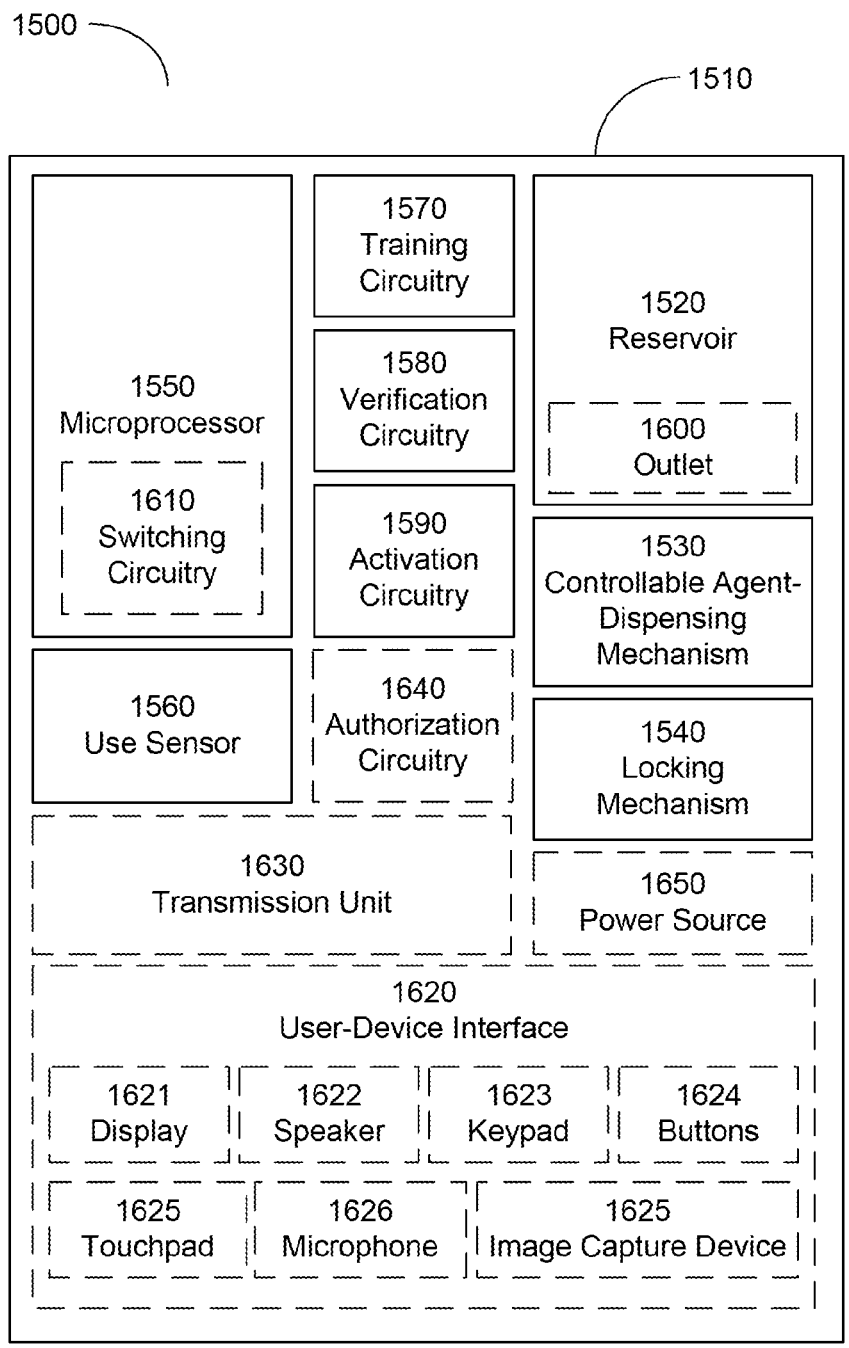
FIG. 16 is a schematic illustrating further aspects of an embodiment of an agent-dispensing device such as shown in FIG. 15.

FIG. 16 illustrates further aspects of an agent-dispensing device such as shown in FIG. 15. Reservoir 1520 of agent-dispensing device 1500 can include one or more outlets 1600. One or more outlets 1600 are configured to allow one or more agents to be dispensed from reservoir 1520 and can include, but are not limited to, one or more of a valve, a septum, a gate, or a removable seal. For example, one or more outlets 1600 can include a valve that is actuated in response to the activation signal. In one embodiment, the one or more outlets 1600 can be used for refilling reservoir with one or more agents. For example, one or more outlets 1600 that includes a lockable screw top can be opened, one or more agents placed in reservoir 1520, and the lockable screw top reclosed.

Microprocessor 1550 of agent-dispensing device 1500 can include switching circuitry 1610. Switching circuitry 1610 is configured to switch operation of agent-dispensing device 1500 between a dispensing mode and a training mode. In the dispensing mode, all of the components necessary for dispensing one or more agents from the device are ready for use once verification and activation have occurred. In the training mode, only a subset of the components necessary for dispensing one or more agents from the device are ready for use, e.g., the components necessary to train the user in proper use of the agent-dispensing device. For example, various buttons or plungers may be actuatable but are otherwise disconnected from the controllable agent-dispensing mechanism such that no agent is dispensed. For example, a needle component of an injection device may be retracted in a training mode. For example, a second reservoir containing a placebo, e.g., water or saline, may be accessed in training mode while a first reservoir containing one or more therapeutic or preventative agents may only be accessed in dispensing mode. Switching from training to dispensing mode can be part of activation mediated by the activation circuitry of the device.

Agent-dispensing device 1500 may further include user-device interface 1620 for interfacing with the user. User-device interface 1620 may be operably linked to training circuitry 1570, verification circuitry 1580, and/or activation circuitry 1590, and can include, but is not limited to, display 1621, speaker 1622, keypad 1623, buttons 1624, touchpad 1625, microphone 1626, and/or image capture device 1625. In one embodiment, training circuitry 1570 includes at least one of text, images, audio, or video training instructions regarding the at least one operational step for use of agent-dispensing device 1500, the training instructions accessible to the user through user-device interface 1620.

In one embodiment, agent-dispensing device 1500 further includes a transmission unit 1630 including an antenna. Transmission unit 1630 including an antenna is configured to transmit and receive wireless signals. For example, transmission unit 1630 may be configured to receive wireless signals containing information with updates to training circuitry 1570, verification circuitry 1580, and/or activation circuitry 1590. In one embodiment, updates are sent to the agent-dispensing device depending upon one or more conditions, non-limiting examples of which include the one or more agents being dispensed, the location of dispensing, or the identity of the user trying to use the device. For example, transmission unit 1630 may be connected to circuitry configured to prepare and transmit information regarding the user's training progress in the form of a report. The report may be transmitted to a caregiver, e.g., a nurse, doctor, or pharmacist to provide information on whether or not the user has been able to train him or herself adequately to enable activation of the agent dispensing device. The report may be transmitted to the manufacturer and/or supplier of the agent-dispensing device to provide information regarding ease of use of the product and/or technical difficulties with the product. Non-limiting aspects of a transmission unit have been described above herein.

In one embodiment, transmission unit 1630 may be configured for bi-directional communication link with an external source. The bi-directional communication link can include one or more of a point-to-point link, a broadcast link, a multipoint link, a point-to-point link, a private link, and/or a public link. The bi-directional communication link can be selected from, but not limited to, a telephone line, an intranet, the Internet, a satellite, a microwave radio relay, a laser waveform, or a global positioning system link. Non-limiting examples of dispensing devices with communication links are described in U.S. Patent Application 2011/0166700, and U.S. Patent Application 2001/0022279, which are incorporated herein by reference.

Agent-dispensing device 1500 can further include authorization circuitry 1640 configured to authenticate the user as an authorized user of the agent dispensing device. Authorization circuitry 1640 is operably linked to microprocessor 1550 and configured to authenticate the user as an authorized user of the agent-dispensing device by comparing a user input with a set of authorized user inputs. User input can be entered using user-device interface 1620 operably connected to authorization circuitry 1640. In one embodiment, the user input may include entering an authorization code using user-device interface 1620, the entered authorization code compared with a set of authorized authorization codes. For example, the user input may include entering an alphanumeric code which is compared to a set of stored authorized alphanumeric codes. In one embodiment, the user input may include one or more biometric parameters, e.g., a fingerprint, a retinal scan, facial recognition, or other biometric input, the entered biometric input compared with stored biometric input for authorized users. For example, agent-dispensing device may include a user-device interface that is a fingerprint scanner on which a potential user must place a finger, e.g., index finger, for comparison with a set of stored authorized fingerprints. In one embodiment, activation permission is tied to a specific user of the agent-dispensing device. For example, the activation circuitry may include circuitry configured to receive a user identification, e.g., an authorization code and/or one or more biometric parameters, and to provide a user-specific activation signal. In one embodiment, activation circuitry 1590 is responsive to authorization circuitry 1640 and configured to deactivate the locking mechanism only for an authorized user of the agent-dispensing device. For example, even if a user is able to go through the training and verification, that user may not be an authorized user, in which case activation may be denied, preventing the one or more agents from being dispensed.

Agent-dispensing device 1500 includes power source 1650. Power source 1650 is operably connected to one or more components of agent-dispensing device including, but not limited to, reservoir 1520, controllable agent-dispensing mechanism 1530, locking mechanism 1540, microprocessor 1550, use sensor 1560, training circuitry 1570, verification circuitry 1580, activation circuitry 1590, outlet 1600, switching circuitry 1610, user-device interface 1620, transmission unit 1630, and authorization circuitry 1640. Non-limiting examples of power sources have been described above herein.

Figure 17:
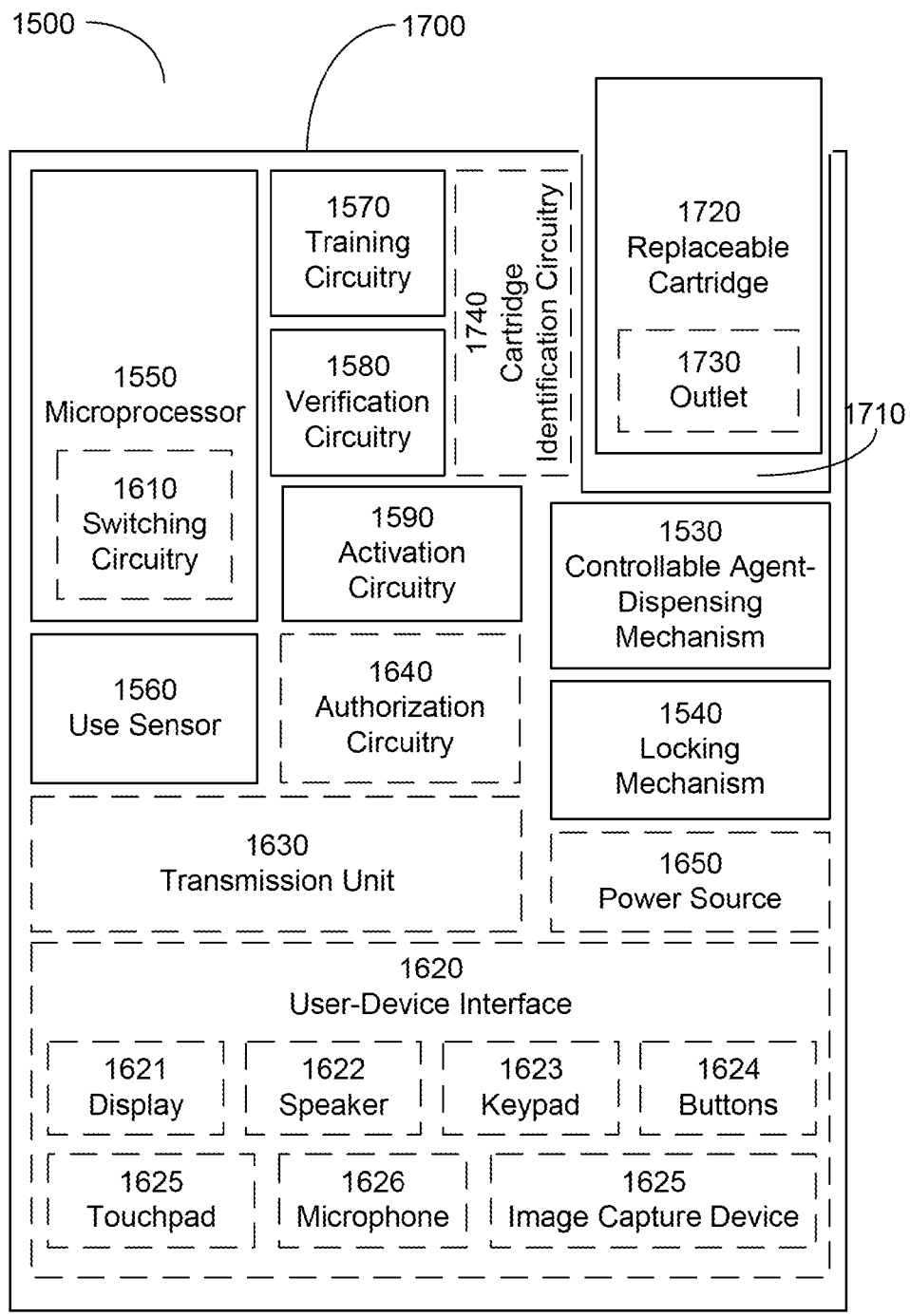
FIG. 17 is a schematic illustrating further aspects of an embodiment of an agent-dispensing device such as shown in FIG. 15.

In one embodiment, the at least one reservoir of agent-dispensing device 1500 includes at least one replaceable cartridge configured to be received by a docking site associated with the housing of the agent-dispensing device. FIG. 17 illustrates further aspects of an agent-dispensing device such as that depicted in FIG. 15 including at least one replaceable cartridge. Agent-dispensing device 1500 may optionally include housing 1700 which includes docking site 1710 configured to allow docking of one or more replaceable cartridge 1720 to agent-dispensing device 1500. In one embodiment, docking site 1710 can include one or more receptacles or openings defined by one or more walls or surfaces of housing 1700 into which one or more replaceable cartridge 1720 is able to be inserted. For example, docking site 1710 may include a cylindrical space configured to accommodate insertion of a cylindrical replaceable cartridge 1720. For example, docking site 1710 may include a rectangular space configured to accommodate insertion of a rectangular replaceable cartridge 1720. In one embodiment, docking site 1710 can include a male/female connector, e.g., a male portion of housing 1700 configured to insert or snap into a female portion of replaceable cartridge 1720. In one embodiment, the male/female connection is made at one or more outlets 1730 in the replaceable cartridge through which one or more agents contained in the cartridge will eventually be dispensed. The one or more outlets 1730 may include a seal that is broken upon forming the male/female connection. In one embodiment, docking site 1710 includes a groove into which an appropriately shaped portion of replaceable cartridge 1720 is able to slide and lock into. In one embodiment, docking site 1710 can include at least one magnetic surface configured to magnetically interact with at least one magnetized surface of replaceable cartridge 1720. In one embodiment, a portion of docking site 1710, e.g., a sharp beveled tube forming an enclosed fluid channel, may puncture an outlet into replaceable cartridge 1720 upon inserting replaceable cartridge 1720 into docking site 1710. For example, replaceable cartridge 1720 can be a vial including a septum, the septum of the vial punctured by needle-like structure associated with docking site 1710.

Agent-dispensing device 1500 can accommodate one or more cartridges 1720. Any given replaceable cartridge 1720 is configured for storing and dispensing one or more agents for preventing and/or treating a disease or condition, non-limiting examples of which have been described above herein. In one embodiment, the at least one agent contained in replaceable cartridge 1720 is released directly to the user from one or more controllable outlets 1730 associated with replaceable cartridge 1720. In one embodiment, the at least one agent contained in replaceable cartridge 1720 is released indirectly to the user through agent-dispensing device 1500. For example, the at least one agent may be released into agent-dispensing device 1500 from replaceable cartridge 1720 and subsequently controllable agent-dispensing mechanism 1530 is activated to release the at least one agent from agent-dispensing device 1500. In this way, the cartridge itself does not need a controllable dispensing mechanism. For example, insertion of replaceable cartridge 1720 into docking site 1710 may penetrate a septum associated with replaceable cartridge 1720. However, it is intended that no agent is released until agent-dispensing device 1500 is activated, e.g., after locking mechanism 1540 of controllable agent-dispensing mechanism 1530 is deactivated and unlocked following training and verification of competency of the user. Replaceable cartridge 1720 is primed to release material, e.g., a therapeutic or preventative agent, and may even release material into a holding reservoir or chamber associated with agent-dispensing device 1500 from which the material is ultimately released to the user in response to deactivation of the locking mechanism. In one embodiment, agent-dispensing device 1500 may include an actuator that is activated by the activation signal and triggers opening of an outlet on the cartridge.

Replaceable cartridge 1720 can include any of a number of packaging forms appropriate for storing and dispensing agents for treating and/or preventing a disease or condition. Non-limiting examples of packaging forms include one or more of a pressurized canister, glass vial with septum, blister package, other packaging with removable seals, aluminum can or bottle, antistatic bag, ampule, sachet, collapsible tube, flexible pouch, bottle, box, plastic bottle, pouch, or microchip. The one or more agents stored in replaceable cartridge 1720 can be in any of a number of physical forms, non-limiting examples of which include gaseous form, solid form, liquid or gel form. In one embodiment, the one or more agents include solid form agents, e.g., one or more of a pill, tablet, small particles, powder, or dissolvable film.

In one embodiment, replaceable cartridge 1720 can include a single storage space from which one or more agents are controllably released. For example, replaceable cartridge 1720 can include a replaceable canister configured to store and dispense multiple metered doses of an inhalant, e.g., the asthma medication salbuterol or the flu vaccine FluMist®. For example, replaceable cartridge 1720 can include a replaceable vial configured to store and dispense multiple doses of an injectable agent, e.g., insulin. In one embodiment, replaceable cartridge 1720 includes a separate storage space for each agent to be stored and dispensed. For example, replaceable cartridge 1720 may include two storage spaces, a first storage space containing agent X and a second storage space containing agent Y. In one embodiment, docking site 1710 is configured to accept a first and second replaceable cartridge, the first cartridge configured to store and dispense at least one first agent and the second cartridge configured to store and dispense at least one second agent. In one embodiment, replaceable cartridge 1720 can include a plurality of storage spaces from which each dose of one or more agents is dispensed. For example, replaceable cartridge 1720 may include a series of storage spaces, each storage space covered by a removable seal. Replacing cartridge 1720 with a new cartridge containing one or more agents that differ from the one or more agents in the replaced cartridge 1720 may trigger an updates to the training and verification circuitry to reflect the new one or more agents intended for use with the agent-dispensing device.

In one embodiment, agent-dispensing device 1500 includes cartridge identification circuitry 1740 configured to read a cartridge identification code, e.g., a radiofrequency tag or bar code, associated with the inserted replaceable cartridge 1720. The cartridge identification code can be used to identify the one or more agents contained in the cartridge and dosing information. In one embodiment, the output of the training circuitry, e.g., the type of information and/or instructions provided to the user, is dependent upon the at least one cartridge configured for storing and dispensing the one or more agents. For example, agent-dispensing device 1500 may be capable of accepting different types of cartridges containing different types of agents. As such, the training and verification provided to the user is customized to reflect the content of the cartridge, which may be determined based on the cartridge identification code. In one embodiment, agent-dispensing device includes circuitry to scan data carried on the replaceable cartridge. For example, agent-dispensing device may include a scanner capable of reading a bar code carried on the replaceable cartridge.

FIG. 18 illustrates a method of verifying user competency of an agent-dispensing device. The method includes providing a web-based interactive tool to a user through a computing device, the web-based interactive tool including stored text, images, audio, and/or video, and a training module to provide training to the user in proper use of the agent-dispensing device, a verification module to verify a competency of the user in the proper use of the agent-dispensing device, and an activation module responsive to the verification module and operable to provide an activation signal to deactivate a locking mechanism of the agent-dispensing device at block 1800; training the user in the proper use of the agent-dispensing device using the training module of the web-based interactive tool at block 1810; verifying a competency of the user in the proper use of the agent-dispensing device using the verification module of the web-based interactive tool at block 1820; and activating the agent-dispensing device with the activation module of the web-based interactive tool by providing the activation signal to deactivate the locking mechanism to allow dispensing of one or more agents from the agent-dispensing device after verifying the competency of the user in the proper use of the agent-dispensing device at block 1830.

Figure 19:
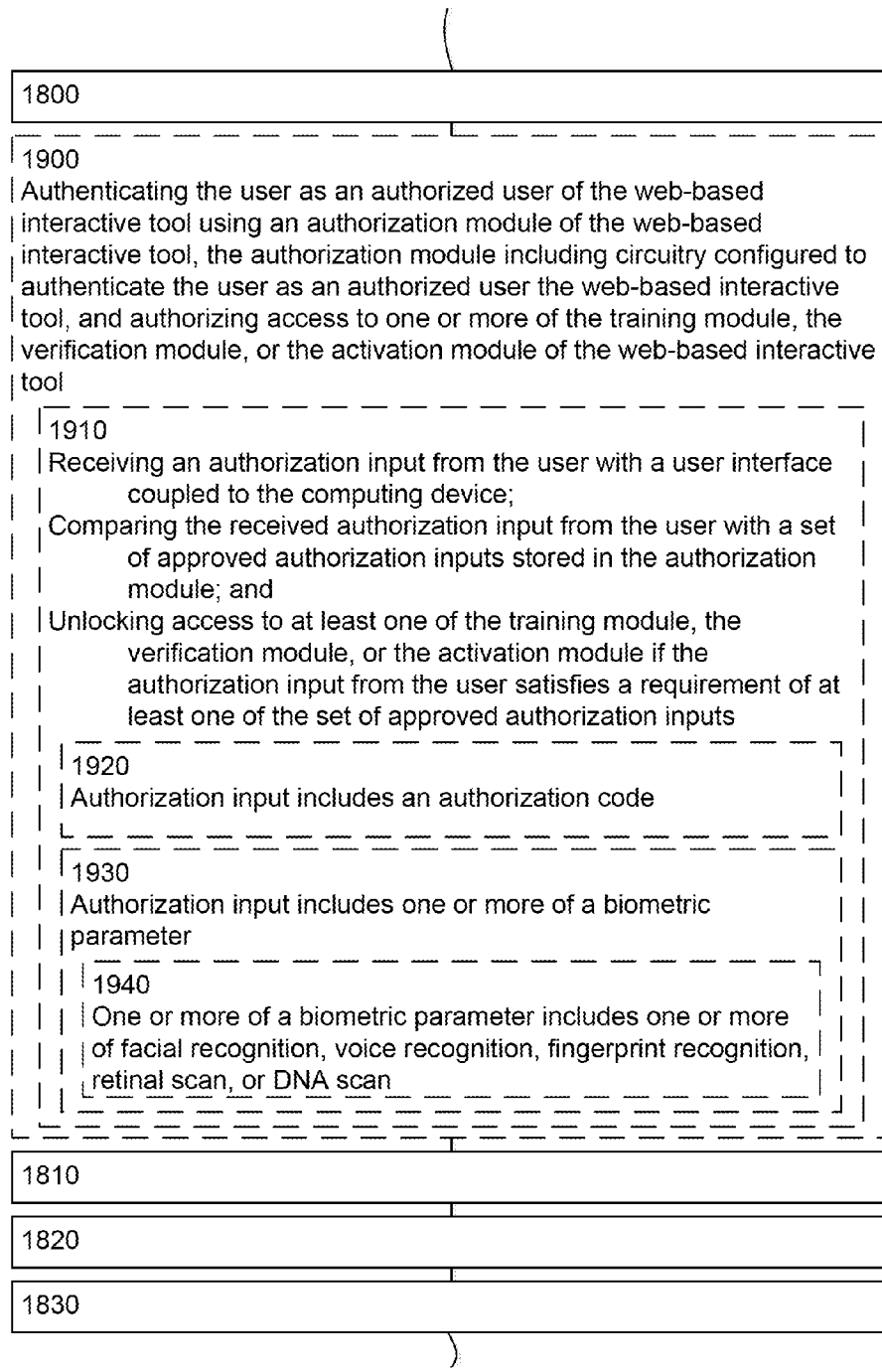
FIG. 19 is a flowchart illustrating further aspects of a method such as shown in FIG. 18.

FIG. 19 illustrates further aspects of a method such as that shown in FIG. 18. In one embodiment, the method includes authenticating the user as an authorized user of the web-based interactive tool using an authorization module of the web-based interactive tool, the authorization module including circuitry configured to authenticate the user as an authorized of the web-based interactive tool, and authorizing access to one or more of the training module, the verification module, or the activation module of the web-based interactive tool as illustrated in block 1900. In one embodiment, the authorization module limits the use of at least a portion of the web-based interactive tool to only an authorized user. For example, a user may only be able to access the web-based interactive tool by signing into a website with a user name/ID and password. For example, a user may be able to access the training module of the web-based interactive tool but must be verified as an authorized user prior to verifying performance and deactivating the locking mechanism to allow dispensing of one or more agents from the agent-dispensing device. In one embodiment, authorization to access portions of the web-based interactive tool is dependent upon the user's authorization to use a specific agent-dispensing device and/or agent.

In one embodiment, the method includes at block 1910 receiving an authorization input from the user with a user interface coupled to the computing device; comparing the received authorization input from the user with a set of approved authorization inputs stored in the authorization module; and unlocking access to at least one of the training module, the verification module, or the activation module if the authorization input from the user satisfies a requirement of at least one of the set of approved authorization inputs. In one embodiment, authorization module includes a list of authorized users of a given agent-dispensing device and/or agent-containing cartridge. The list of authorized users can be in the form of a list of names, a list of social security numbers, an authorization code, a user-specific biometric parameters, or any other property, number, or code that is specific for a given individual. If an unauthorized user is trying to use the agent-dispensing device by accessing activation through the web-based interactive tool, the authorization module may further include circuitry to prevent the activation module from providing the activation signal or to prevent the agent-dispensing device from dispensing one or more agents, e.g., transmitting a signal to lock or incapacitate one or more of the functional components of the agent-dispensing device.

In one embodiment, the authorization input can include an authorization code as shown in block 1920. In one embodiment, the authorization code can include an alphanumeric login and/or password specific for the user. For example, the user may receive a login and/or password for authorized entry into web-based interactive tool from a physician, pharmacist, manufacturer, or other relevant entity, the login and/or password entered into the computing device using a user interface component. In one embodiment, the authorization code is provided on a smartcard, radiofrequency identification (RFID) tag, or other data form that can be "read" by the computing device or operably connected device to allow access to web-based interactive tool.

In one embodiment, the authorization input optionally includes one or more of a biometric parameter as shown in block 1930. In one embodiment, the one or more of a biometric parameter include one or more of facial recognition, voice recognition, fingerprint recognition, retinal scan, or DNA scan, as shown in block 1940. Other non-limiting examples of biometric parameters include blood vessel scans, handwriting, or other means of identifying a specific user. The one or more biometric parameters provided by a user may be compared with a set of biometric parameters of authorized users using one or more comparison algorithms associated with the authorization module.

In one embodiment, it may be necessary to provide authorization input, e.g., an authorization code or biometric parameter, directly to the agent-dispensing device through a user-device interface prior to using the agent-dispensing device. For example, the agent-dispensing device may include user identification circuitry that accepts authorization input and compares user input with a set of authorized users of the agent-dispensing device prior to unlocking any functions of the device.

FIG. 20 illustrates further aspects of a method such as that shown in FIG. 18. The method includes providing a web-based interactive tool to a user through a computing device, as shown in block 1800. The method includes providing the web-based interactive tool to a computing device accessible to the user through a desktop computer, a laptop computer, a tablet computing device, a personal electronic device, or a dedicated computing device accessible to the user as illustrated in block 2000. Other non-limiting examples of computing devices for use in the method have been described above herein. In one embodiment, the method includes providing the web-based interactive tool to a computing device incorporated into the agent-dispensing device.

In one embodiment, the method includes providing the web-based interactive tool to the user through the computing device via the Internet, as shown in block 2010. In one embodiment, the method includes providing the web-based interactive tool to the user through the computing device in communication with a remote server, as shown in block 2020. For example, the web-based interactive tool can be provided to a laptop computer situated in a user's residence using an Internet connection. For example, the web-based interactive tool can be provided to a user's smartphone using a broadband/Internet provider. In one embodiment, the method includes providing the web-based interactive tool from one or more servers located in a location remote from the user. In one embodiment, the method includes providing the web-based interactive tool from a mainframe computer located in a location remote from the user. The remote server can be part of a computer network, web service, cloud-based infrastructure, or the like. In one embodiment, the method includes providing the web-based interactive tool from a government-affiliated location, e.g., the Food & Drug Administration (FDA), the Center for Disease Control (CDC), the World Health Organization, or a local/state/national public health department. In one embodiment, the method can include providing the web-based interactive tool from the source of the agent-dispensing device and/or associated cartridges, e.g., from a pharmaceutical company, a pharmacy or pharmacy chain, or a hospital or clinic. In one embodiment, the method includes providing the web-based interactive tool from an international site, e.g., in a country distinct from the country in which the agent-dispensing device is used. For example, a remote server could be located in an industrialized/developed country, e.g., the United States or Europe and accessible to a user in a developing country, e.g., a West African country, through a satellite communications link. For example, the method could include remotely training and verifying the competency of a user, e.g., an aide worker, located in a developing country and activating the agent dispensing device for dispensing a vaccine or other therapeutic agent in that developing country.

Figure 21:
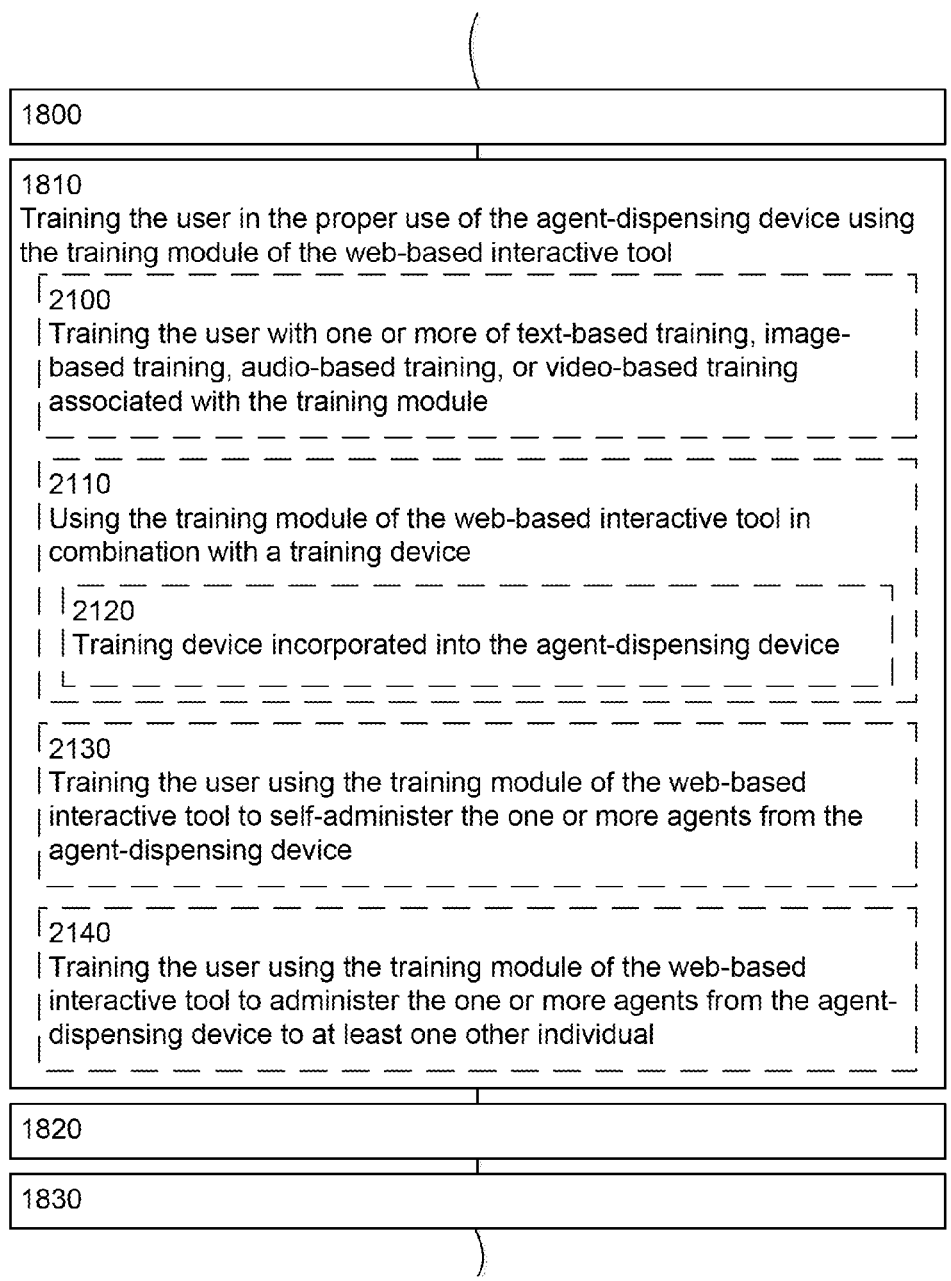
FIG. 21 is a flowchart depicting further aspects of a method such as illustrated in FIG. 18.

FIG. 21 illustrates further aspects of a method such as that shown in FIG. 18. The method includes training the user in the proper use of the agent dispensing device using the training module of the web-based interactive tool. In one embodiment, the method includes training the user with one or more of text-based training, image-based training, audio-based training, or video-based training associated with the training module, as shown in block 2100. For example, the method can include training the user using text, image, audio, and/or video content contained with the training module or accessible to the training module. The method includes training the user in the proper use and care of the agent-dispensing device and in the proper use of the one or more agents dispensed from the device and can include, but is not limited to, training in proper handling and care of the dispensing device, e.g., cleaning, changing batteries, and the like; handling and care of cartridges indicated for use with the agent-dispensing device, e.g., proper insertion and storing; training in proper dosing, e.g., timing and dosing restrictions; training in monitoring adverse events; and training in proper use of the agent-dispensing device, e.g., how to hold the device and positioning of device relative to skin or other body part. In one embodiment, the method may include training the user by providing prescribing information for the one or more agents.

In one embodiment, the method includes using the training module of the web-based interactive tool in combination with a training device as shown in block 2110. Examples and uses of a training device in combination with a web-based interactive tool have been described above herein. The training device can be a separate entity or can be incorporated into the drug dispensing device, as shown in block 2120 and in FIG. 4. Optionally, the training device dispenses a placebo dosage form, e.g., water, saline, a sugar pill, or a sugar solution. In general, using the training device in combination with the web-based interactive tool allows the user to train on a device nearly identical to the agent-dispensing device without actually administering (or wasting) the active agent.

In one embodiment, the method includes training the user using the training module of the web-based interactive tool to self-administer the one or more agents from the agent-dispensing device as shown in block 2130. For example, the web-based interactive tool can include one or more instructions for self-administering one or more agents configured to prevent and/or treat a disease or condition. The method can include training the user to use the dispensing device for self-inhalation, self-injection, transdermal, and oral administration. For example, an individual in a remote location can receive the agent-dispensing device and any associated agent-containing cartridges through a delivery service, access the web-based interactive tool, undergo training and verification, and activate the agent-dispensing device, all without having to travel to a clinic or other medical facility.

In one embodiment, the method includes training the user using the training module of the web-based interactive tool to administer the one or more agents from the agent-dispensing device to at least one other individual, as shown in block 2140. For example, the web-based interactive tool can include one or more instructions for administering one or more agents from the agent-dispensing device to another individual. The method can include training the user to administer one or more agents from the agent-dispensing device to another individual by inhalation, injection, transdermal, or oral administration. For example, the user may be a family member, a friend, or other caregiver of an individual for whom the agent-dispensing device and/or associated cartridges has been prescribed. In some embodiments, the caregiver may be a user who is tending to one specific individual, for example a hospice nurse. In some embodiments, the caregiver may be a user who is caring for a number of individuals in a household or community. For example, the caregiver may be a physician, nurse, EMT or other caregiver working in a remote and/or isolated village, e.g., in rural Alaska or in field station in Antarctica. For example, the caregiver may be an aide worker working in a remote and isolated village in a developing country. For example, the caregiver may be a local individual who otherwise has no medical experience, but under emergency circumstances is called upon to administer one or more agents, e.g., a vaccine or an antidote, to other members of a community. For example, a user, e.g., a parent, home aide, or other caregiver, in a remote location may receive the agent-dispensing device and any associated cartridges through a delivery service, access the web-based interactive tool, undergo training and verification, and activate the agent-dispensing device, all without having to travel to a medical clinic or other facility.

Figure 22:
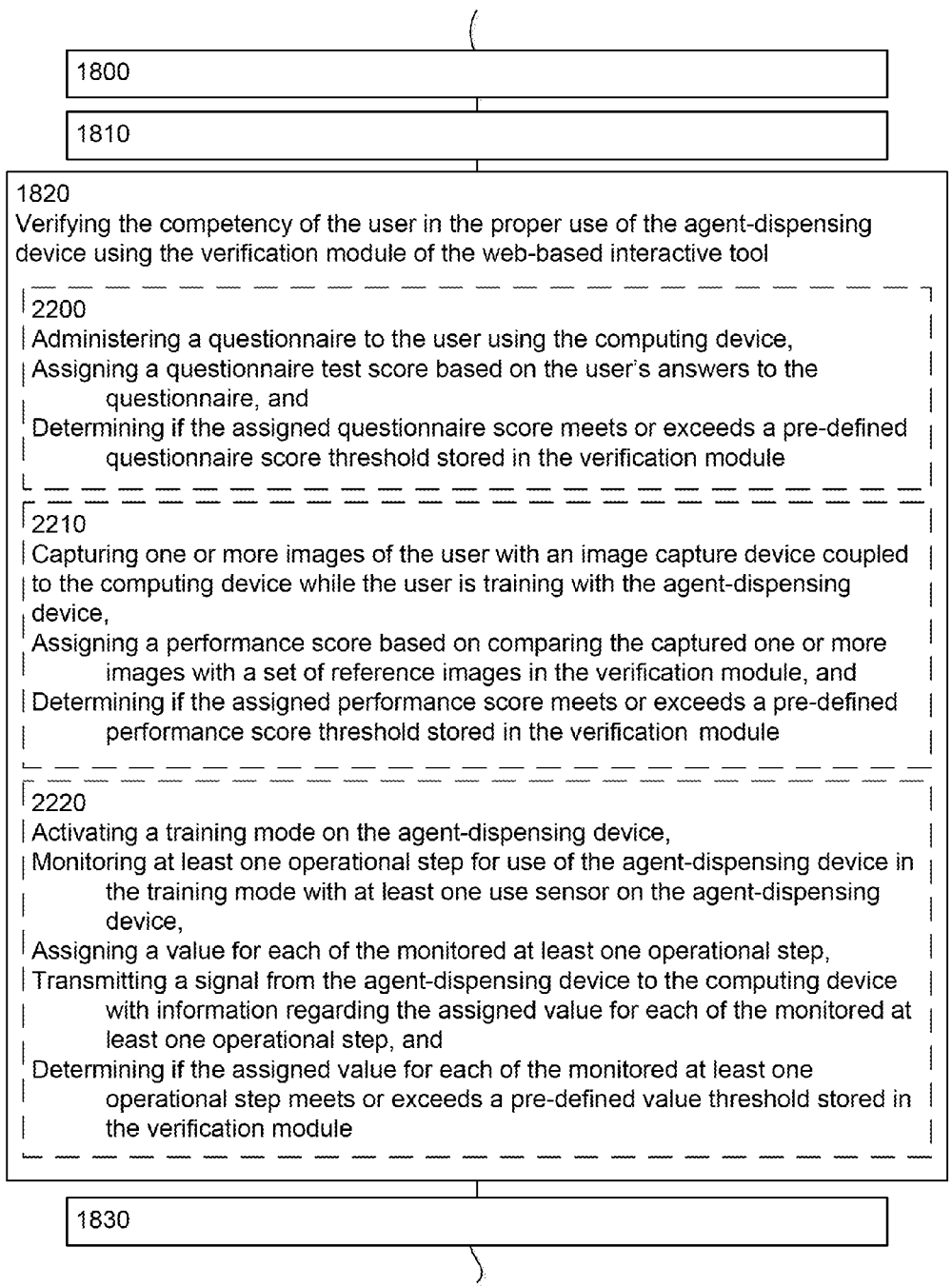
FIG. 22 is a flowchart illustrating further aspects of a method such as shown in FIG. 18.

FIG. 22 illustrates further aspects of a method such as that shown in FIG. 18. The method includes verifying the competency of the user in the proper use of the agent-dispensing device using the verification module of the web-based interactive tool as shown in block 1820. Verifying the competency of the user may include generating a test score, e.g., a percentage of questions answered correctly in either a written or oral exam or a performance score based on analysis of captured images. Verifying the competency of the user can include an automatic assessment based on signals sent from the agent-dispensing device or an associated training device while the user trains with the device. In one embodiment, verifying the competency of the user may be correlated with achieving a test score that meets or exceeds a pre-defined performance threshold, e.g., 85% or higher. In one embodiment, verifying the competency of the user may include interacting with a third party observer via a communications link.

In one embodiment, verifying a competency of the user is performed using the verification module only after training has been completed, e.g., after the user has viewed and/or listened to the entirety of the training instructions included in the training module. For example, the web-based interactive tool can be constructed such that the user cannot access the verification module until the training module has been fully viewed. In one embodiment, a user who has completed the training in the past may choose to by-pass the training module and proceed directly to the verification module. For example, the web-based interactive tool can be constructed to include "memory" that a particular user has already completed training and offer direct access to the verification module, thus by-passing the requirement to go through the components of the training module prior to accessing the verification module.

In one embodiment, verifying the competency of the user in the proper use of the agent-dispensing device includes administering a questionnaire to the user using the computing device, assigning a questionnaire score based on the user's answers to the questionnaire, and determining if the assigned questionnaire score meets or exceeds a pre-defined questionnaire score threshold stored in the verification module, as illustrated in block 2200. In one embodiment, the questionnaire is provided to the user in a text form as various screens on the display of the computing device, the user providing answers through a user interface of the computing device, e.g., a keyboard or touchpad. In one embodiment, the questionnaire is provided to the user in an audio form, the user providing answers either using a keyboard or touchpad or by providing verbal responses through a microphone coupled to the computing device. The user's responses to the text-based or audio-based questionnaire are used to assess the competency of the user in proper use of the agent-dispensing device. For example, the user's responses to the questionnaire may be compared with a stored set of responses and a questionnaire score assigned to the user's responses. If the user's assigned questionnaire score meets or exceeds a pre-defined questionnaire score, the user is deemed competent.

In one embodiment, verifying the competency of the user in the proper use of the agent-dispensing device includes capturing one or more images of the user with an image capture device coupled to the computing device while the user is training the with agent-dispensing device, assigning a performance score based on comparing the captured one or more images with a set of reference images in the verification module, and determining if the assigned performance score meets or exceeds a pre-defined performance score threshold stored in the verification module, as shown in block 2210. In one embodiment, the verification module of the web-based interactive tool includes software components or algorithms capable of evaluating the performance/competency of the user by comparing with a stored set of reference images and generates a test score. Non-limiting examples of algorithms for analyzing images have been described above herein.

In one embodiment, the method includes verifying the competency of the user in the proper use of the agent-dispensing device through video-conferencing. For example, the competency of the user is verified by having the user proceed through a series of steps associated with proper use of the agent-dispensing device and/or associated cartridges while being videotaped with an image capture device. In one embodiment, the live or taped video is viewed by a third party examiner who generates a test score based on the performance/competency of the user. In one embodiment, the user is in live video communication with a third party examiner using a video conferencing tool, e.g., SKYPE® (Microsoft, Redmond, Wash.). In one embodiment, the user is taped performing one or more steps, the taped session sent to a third party examiner, and a performance test score provided to the user.

In one embodiment, verifying the competency of the user in the proper use of the agent-dispensing device includes activating a training mode on the agent-dispensing device, monitoring at least one operational step for use of the agent-dispensing device in the training mode with at least one use sensor on the agent-dispensing device, assigning a value for each of the monitored at least one operational step, transmitting a signal from the agent-dispensing device to the computing device with information regarding the assigned value for each of the monitored at least one operational step, and determining if the assigned value for each of the monitored at least one operational step meets or exceed a pre-defined value threshold stored in the verification module, as illustrated in block 2220. In one embodiment, activating a training mode on the agent-dispensing device includes switching from a dispensing mode to a training mode using switching circuitry associated with the agent-dispensing device. Monitoring at least one operational step for use of the agent-dispensing device in the training mode with at least one use sensor on the agent-dispensing device includes monitoring the at least one operation step with at least one of an accelerometer, a timer, an actuator, a pressure sensor, a touch sensor, inclinometer, temperature sensor, or image capture device. Other non-limiting examples of use sensors include flex sensors, flow sensors, force sensors, gas sensors, gyroscopes, moisture sensors, motion sensors, optical sensors, and vibrations sensors.

Figure 23:
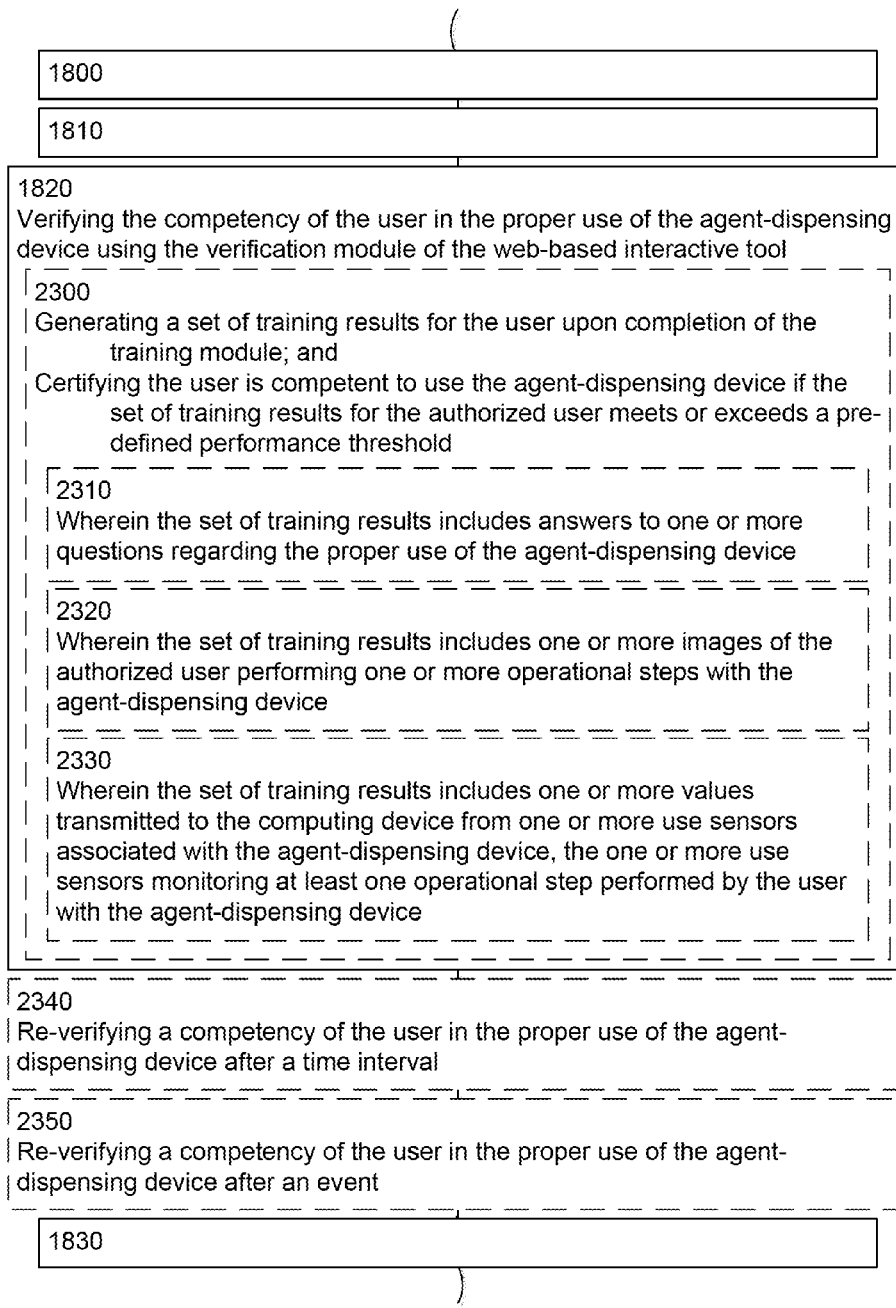
FIG. 23 is a flowchart showing further aspects of a method such as depicted in FIG. 18.

FIG. 23 illustrates further aspects of a method such as that shown in FIG. 18. The method of verifying the competency of the user in the proper use of the agent-dispensing device using the verification module of the web-based interactive tool further optionally includes generating a set of training results for the user upon completion of the training module, and certifying the user is competent to use the agent-dispensing device if the set of training results for the user meets or exceeds a pre-defined performance threshold, as illustrated in block 2300. In one embodiment, the set of training results includes answers to one or more questions regarding the proper use of the agent-dispensing device, as illustrated in block 2310. The answers can be text or oral responses to one or more text or audio-based questionnaires provided to the user from the verification module. In one embodiment, the set of training results includes one or more images of the user performing one or more operational steps with the agent-dispensing device, as illustrated in block 2320. In one embodiment, the set of training results includes one or more values transmitted to the computing device from one or more use sensors associated with the agent-dispensing device, the one or more use sensors monitoring at least one operational step performed by the user with the agent-dispensing device, as illustrated in block 2330. In general, the set of training results is compared with a set of stored test scores, images, or operational steps associated with or accessible by the verification module of the web-based interactive tool.

In one embodiment, the pre-defined performance threshold may include a training test score of up to 100%, e.g., up to 100% correct answers on a performance/competency exam. The pre-defined performance threshold may include a training test score of up to 10 on a 1 to 10 performance scale. In general, the pre-defined performance threshold can be set by the maker of the agent-dispensing device and/or cartridges, e.g., a pharmaceutical company, the distributer of the dispensing device and/or cartridges, e.g., a pharmacy, a caregiver, e.g., a doctor, nurse, aide worker, or other caregiver. The pre-defined performance threshold may be set based on the difficulty of using the agent-dispensing device, potential harm caused by inappropriate use of the dispensing device, and/or the critical nature of the prescribing information. For example, when using a particularly dangerous agent with a potential for harmful side-effects and/or abuse, the pre-defined performance threshold may be set higher to ensure that the user is very competent at using the agent-dispensing device and/or associated cartridges prior to activating the agent-dispensing device.

Returning to FIG. 23, in one embodiment, the method includes re-verifying a competency of the user in the proper use of the agent-dispensing device after a time interval, as shown in block 2340. In one embodiment, re-verification may be required prior to using the agent-dispensing device if the device or an associated agent-containing cartridge has not been used by the user for a long time or is used infrequently. For example, re-verification may be warranted if the user has not used the agent-dispensing device and/or the associated agent in more than a year. In one embodiment, the method further includes re-verifying a competency of the user in the proper use of the agent-dispensing device after an event, as illustrated in block 2350. For example, re-verification may be warranted in response to changes in FDA regulations, changes to the prescribing information for the agent, e.g., inclusion of a black-box warning, upgrades to the agent-dispensing device, and/or upgrades/changes to the web-based interactive tool, e.g., upgrades/changes to the training module and/or verification module, or changes in the pre-defined performance threshold.

Figure 24:
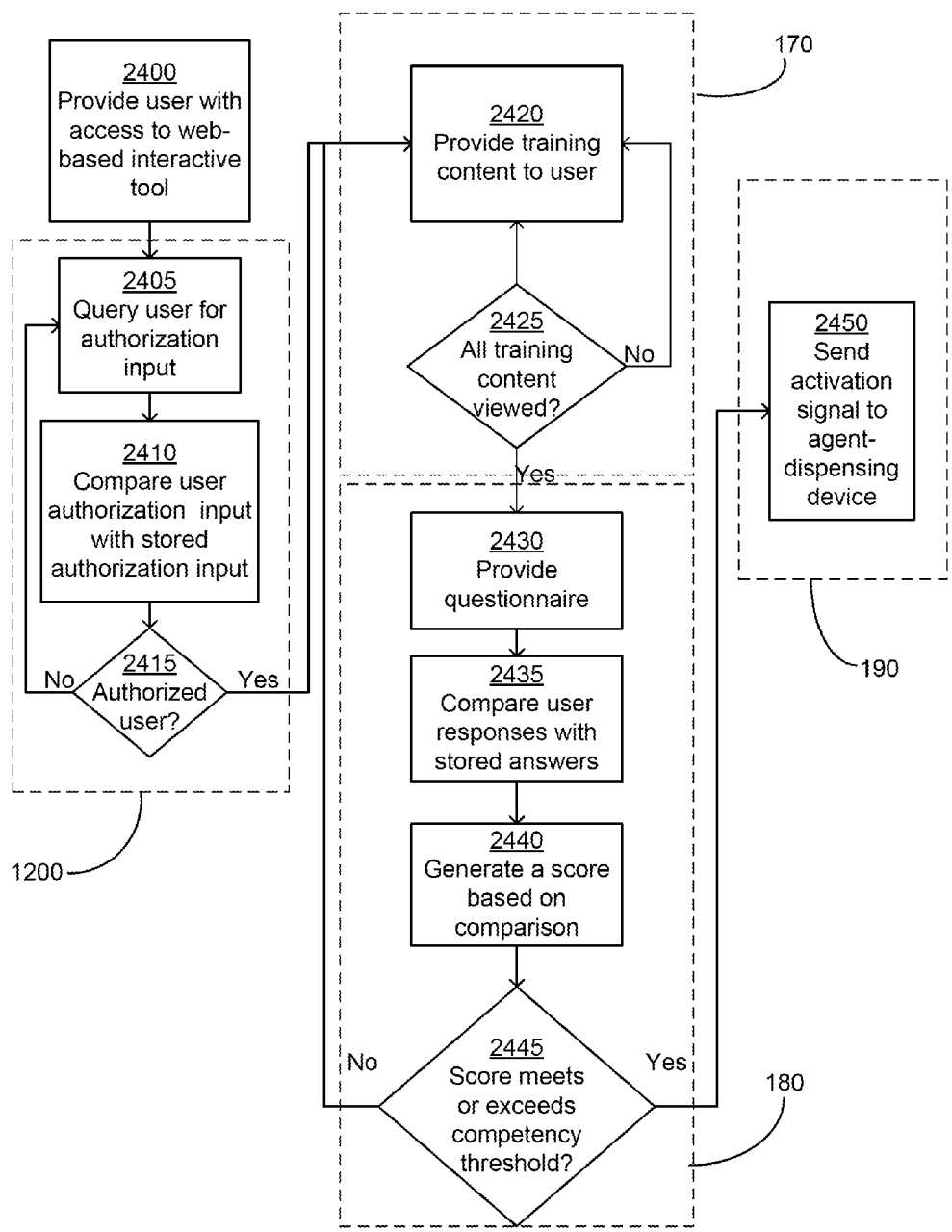
FIG. 24 is a flow diagram illustrating a method of verifying user competency of an agent-dispensing device.

FIG. 24 illustrates aspects of a method for training and verifying a competency of a user prior to activating an agent-dispensing device. The method includes one or more steps implemented with a web-based interactive tool running on a computing device. The method includes provide a user with access to the web-based interactive tool at block 2400. In one embodiment, provide a user with access can include providing the user with a URL for accessing the web-based interactive tool through the Internet. Once the user has entered the first page, e.g., a home page, of the web-based interactive tool, query the user for authorization input at block 2405. In one embodiment, the authorization input includes an authorization code, e.g., an alphanumeric code. In one embodiment, the authorization input includes a biometric input, e.g., a scan of one or more of the user's fingers with a fingerprint scanner linked to the computing device. In block 2410, compare user authorization input with stored authorization input. In block 2415, decide if the user is an authorized user. If yes, provide training content to user at block 2420. If no, return to block 2405 to re-query user for authorization input. At block 2425, determine if all training content has been viewed by the user. If yes provide a questionnaire at block 2430 posing questions regarding the training content. If no, return to block 2420 to continue to provide training content to the user. At block 2435, compare user responses to the questionnaire with stored answers in the verification module. At block 2440, generate a score based on the comparison of the user responses and the stored answers. In block 2445, decide if the score meets or exceeds a competency threshold, e.g., a pre-defined performance threshold. If yes, send activation signal to agent-dispensing device at block 2450. If no, return to block 2320 to provide training content to the user.

Figure 25:
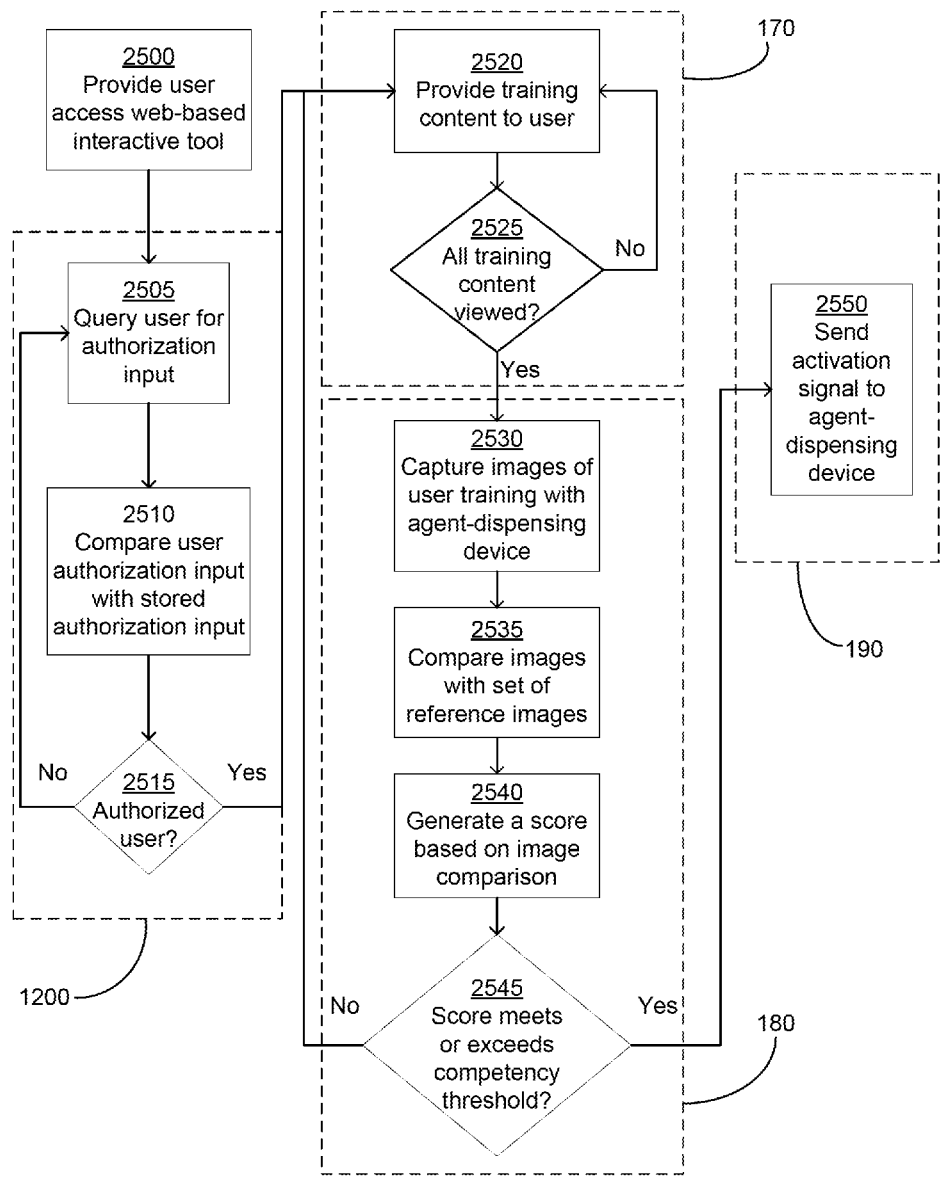
FIG. 25 is a flow diagram illustrating a method of verifying user competency of an agent-dispensing device.

FIG. 25 illustrates aspects of a method for training and verifying a competency of a user prior to activating an agent-dispensing device. The method includes one or more steps implemented with a web-based interactive tool running on a computing device. The method includes provide a user with access to the web-based interactive tool at block 2500. In one embodiment, provide a user with access can include providing the user with a URL for accessing the web-based interactive tool through the Internet. Once the user has entered the first page, e.g., a home page, of the web-based interactive tool, query the user for authorization input at block 2505. In one embodiment, the authorization input includes an authorization code, e.g., an alphanumeric code. In one embodiment, the authorization input includes a biometric input, e.g., a scan of one or more of the user's fingers with a fingerprint scanner linked to the computing device. In block 2510, compare user authorization input with stored authorization input. In block 2515, decide if the user is an authorized user. If yes, provide training content to the user at block 2520. If no, return to block 2505 to re-query the user for authorization input. At block 2525, determine if all training content has been viewed by the user. If yes, capture one or more images of the user training with the agent-dispensing device at block 2530. If no, return to block 2520 to continue to provide training content to user. At block 2535, compare the images of the user training with the agent-dispensing device with a set of reference images. In one embodiment, the reference images include still photos showing proper use of the agent-dispensing device. In one embodiment, the reference images include video showing proper use of the agent-dispensing device. The comparison is made using any of a number of image comparison algorithms, examples of which have been described above herein. At block 2540, generate a score based on the image comparison. At block 2545, decide if the score meets or exceeds a competency threshold, e.g., a pre-defined performance threshold. If yes, provide an activation signal to agent-dispensing device to deactivate a locking mechanism to allow controlled dispensing of one or more agents at block 2550. If no, return to block 2520 and provide additional training content to user.

Figure 26:
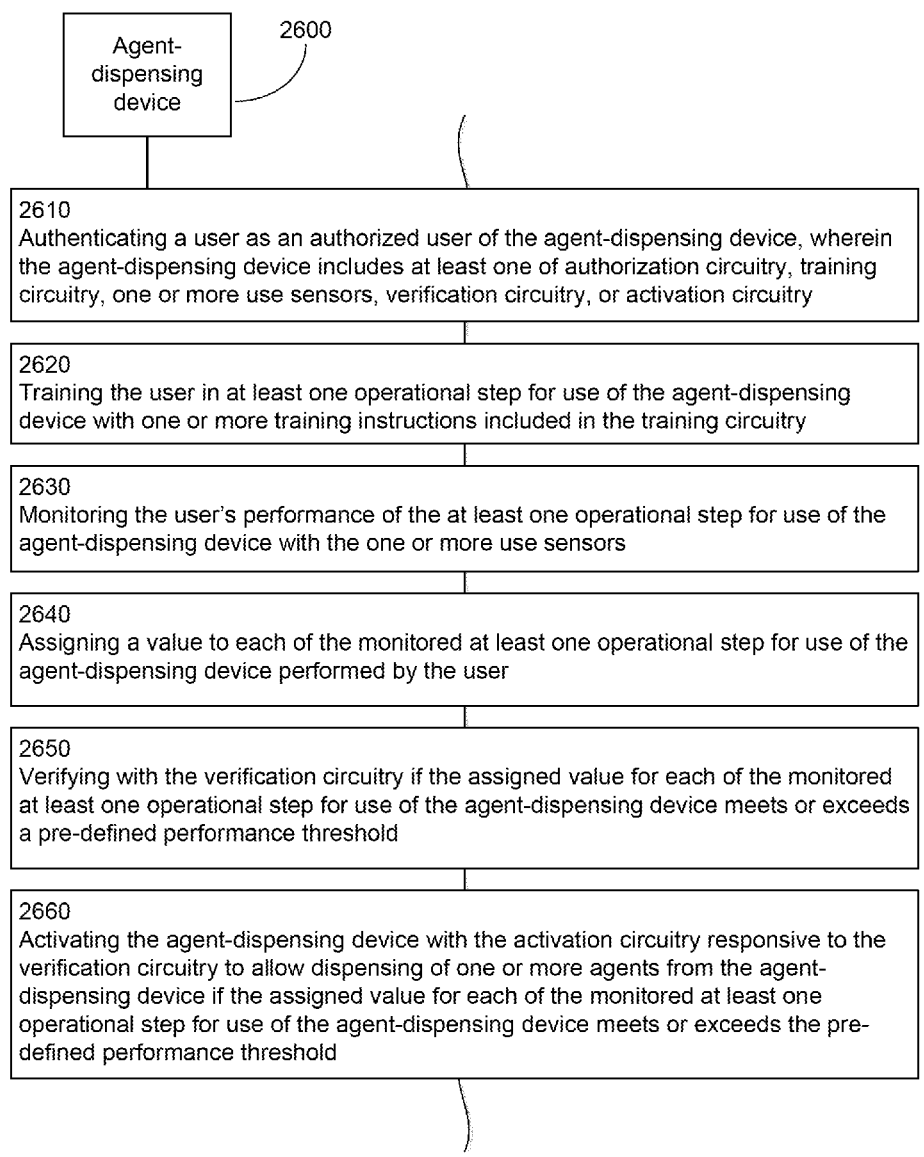
FIG. 26 is a flowchart of a method of verifying user competency implemented with circuitry in an agent-dispensing device.

FIG. 26 illustrates aspects of a method of verifying user competency implemented with circuitry in agent-dispensing device 2600. The method includes authenticating the user as an authorized user of the agent-dispensing device, wherein the agent-dispensing device includes at least one of authorization circuitry, training circuitry, one or more use sensors, verification circuitry, or activation circuitry in block 2610, training the user in at least one operational step for user of the agent-dispensing device with one or more training instructions included in the training circuitry in block 2620, monitoring the user's performance of the at least one operational step for use of the agent-dispensing device with the one or more use sensors incorporated in block 2630, assigning a value to each of the monitored at least one operational step for use of the agent-dispensing device performed by the user in block 2640; verifying with the verification circuitry if the assigned value for each of the monitored at least one operational step for use of the agent-dispensing device meets or exceeds a pre-defined performance threshold in block 2650, and activating the agent-dispensing device with the activation circuitry responsive to the verification circuitry to allow dispensing of one or more agents from the agent-dispensing device if the assigned value for each of the monitored at least one operational step for use of the agent-dispensing device meets or exceeds the pre-defined performance threshold in block 2660.

In one embodiment, the method of FIG. 26 further includes authenticating the user as an authorized user of the agent-dispensing device by receiving an authorization input from the user with a user-device interface associated with the agent-dispensing device; comparing the received authorization input from the user with a set of approved authorization inputs; and unlocking access to at least one of the training circuitry, the verification circuitry, or the activation circuitry if the authorization input from the user satisfies a requirement of at least one of the set of approved authorization inputs. The authorization input can include at least one of an authorization code or a biometric parameter, examples of which have been described above herein.

In one embodiment, the method of FIG. 26 further includes training the user in the at least one operational step for use of the agent-dispensing device with one or more instructions included in the training circuitry includes providing the user with one or more of text, image, audio, or video including one or more instructions for the at least one operational step for use of the agent-dispensing device. The one or more instructions can include one or more operational steps including specific buttons to push or switches to flip, a sequence of buttons to push or switches to flip, a timing between pushing two or more buttons or flipping two or more switches, priming the device, e.g., shaking or pumping the device, cooling the device, heating the device, or moving the device in proximity to a body part, e.g., the mouth or the skin.

In one embodiment, the method of FIG. 26 further includes activating the agent-dispensing device by sending an activation signal to deactivate a locking mechanism of a controllable agent-dispensing mechanism of the agent-dispensing device. In one embodiment, the activation signal originates from the activation circuitry of the agent-dispensing device, the activation circuitry being responsive to the verification circuitry.

Figure 27:
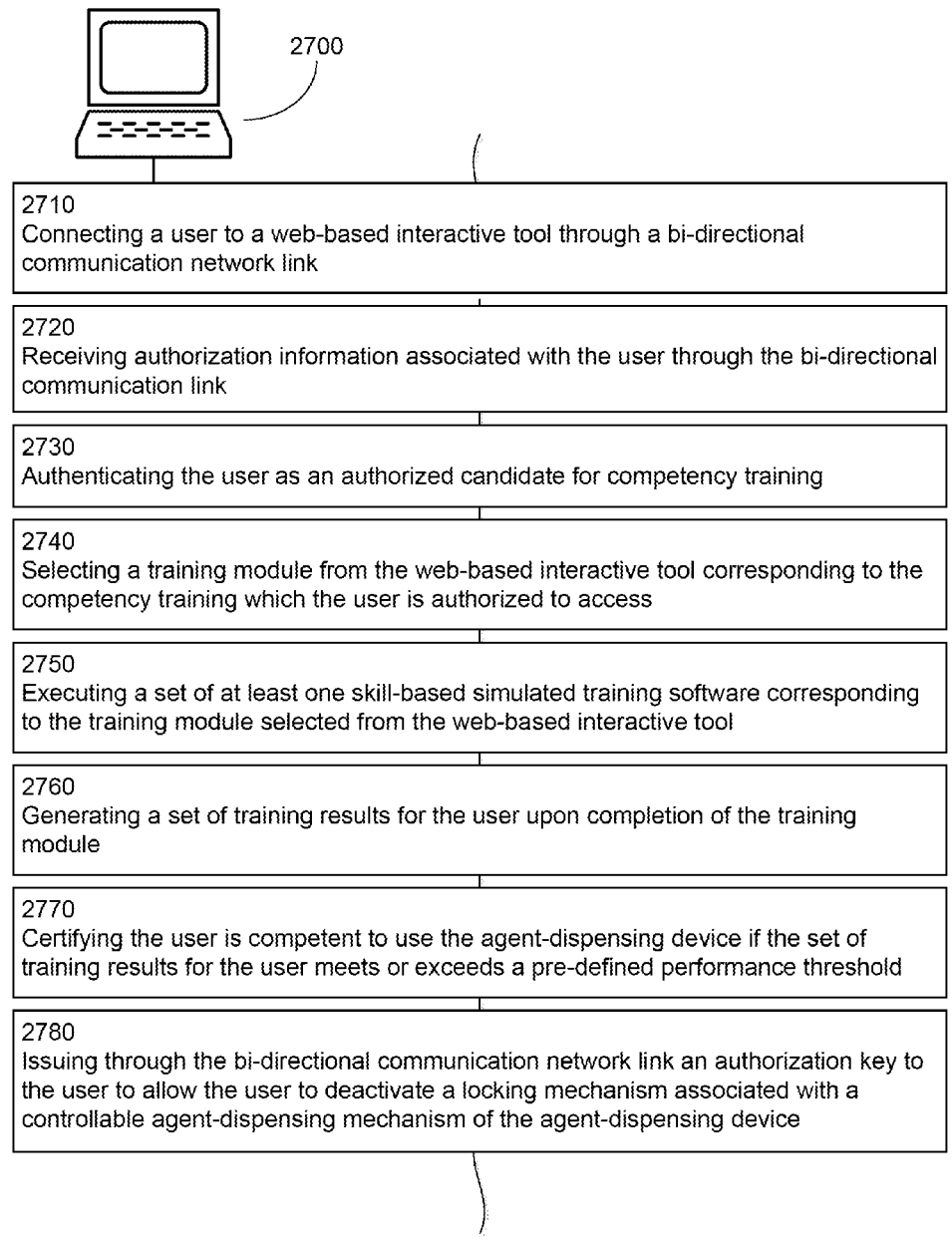
FIG. 27 is a flowchart of a computer-implemented method of authorizing use of an agent-dispensing device following competency training.

FIG. 27 illustrates aspects of a computer-implemented method running on computing device 2700 for authorizing use of an agent-dispensing device following competency training. The method includes connecting a user to a web-based interactive tool through a bi-directional communication network link at block 2710, receiving authorization information associated with the user through the bi-directional communication link at block 2720, authenticating the user as an authorized training candidate for competency training at block 2730, selecting a training module from the web-based interactive tool corresponding to the competency training which the user is authorized to access at block 2740, executing a set of at least one skill-based simulated training software corresponding to the training module selected from the web-based interactive tool at block 2750, generating a set of training results for the user upon completion of the training module at block 2760, certifying the user is competent to use the agent-dispensing device if the set of training results for the user meets or exceeds a pre-defined performance threshold at block 2770, and issuing through the bi-directional communication network link an authorization key to the user to allow the user to deactivate a locking mechanism associated with a controllable agent-dispensing mechanism of the agent-dispensing device at block 2780.

In one embodiment, connecting a user to a web-based interactive tool through a bi-directional communication network link includes connecting the user to the web-based interactive tool using one or more of a point-to-point communication link, a broadcast communication link, a multi-point communication link, a point-to-multipoint communication link, a private communication link, and/or a public communication link. In one embodiment, the bi-directional communication link includes a data link for connecting one location to another for the purposes of transmitting and receiving information. In one embodiment, the bi-directional communication link is an Internet communication link. In one embodiment, the bi-directional communication link is a telephone communication link, non-limiting examples of which include a standard phone line, asymmetric digital subscriber line (ADSL). In one embodiment, the bi-directional communication link is an intranet communication link. In one embodiment, the bi-directional communication link is a satellite communication link. In one embodiment, the bidirectional communication link includes a microwave radio relay. In one embodiment, the bi-directional communication link includes at least two communications links selected from the group of communications links consisting of a telephone line, an intranet, the Internet, a satellite, a laser waveform, or a global positioning system link.

In one embodiment, receiving authorization information associated with the user through the bi-directional communication link includes receiving an authorization code, e.g., a login ID and password, or one or more biometric parameter, e.g., a fingerprint scan. In one embodiment, authenticating the user as an authorized candidate for competency training includes comparing the received authorization information, e.g., authorization code and/or one or more biometric parameter, with a set of authorization information for authorized users.

In one embodiment, selecting a training module form the web-based interactive tool corresponding to the competency training with the user is authorized to access includes selecting a training module based on the one or more agents to be dispensed, e.g., a first training module for a cardiovascular agent and a second training module for an opioid analgesic. In one embodiment, selecting a training module form the web-based interactive tool corresponding to the competency training which the user is authorized to access includes selecting a training module based on the medical experience of the user, e.g., an abbreviated training module for a medical professional versus a more comprehensive training module for a non-medical professional or individual otherwise unfamiliar with the agent-dispensing device and/or the one or more agents. In one embodiment, the training module includes one or more instructions for proper use of the agent-dispensing device and/or any associated agent, non-limiting examples of which include instructions for operating and caring for the agent-dispensing device and one or more instructions regarding the use and properties of any associated agents.

In one embodiment, executing a set of at least one skill-based simulated training software includes executing a set of text or audio-based questions to the user, the set of text or audio-based questions intended to test the user's knowledge regarding the one or more instructions provided in the training module. In one embodiment, executing a set of at least one skill-based simulated training software include executing a set of instructions for performing one or more operational steps with the agent-dispensing device while being monitored with an image capture device associated with either the computing device or the agent-dispensing device. In one embodiment, executing a set of at least one skill-based simulated training software includes executing a set of instructions for performing one or more operational steps with the agent-dispensing device while one or more use sensors monitor the user's performance of the one or more operational steps.

In one embodiment, issuing an authorization key to the user includes issuing an alphanumeric authorization key to the user. The alphanumeric authorization key may be entered into the agent-dispensing device using a user-device interface. In one embodiment, issuing an authorization key to the user includes issuing a bar code or QR code onto a display screen of the computing device that is readable by the agent-dispensing device. In one embodiment, the authorization key is a wireless signal sent directly to the agent-dispensing device to deactivate the locking mechanism associated with the controllable agent-dispensing mechanism of the agent-dispensing device to allow dispensing of one or more agents.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems and medical devices. Those skilled in the art will recognize that electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

Those skilled in the art will recognize that at least a portion of the systems and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

Those skilled in the art will recognize that at least a portion of the systems and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

Those skilled in the art will recognize that at least a portion of the systems and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory.

Further, implementation of at least part of a system for performing a method in one territory does not preclude use of the system in another territory.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Various non-limiting embodiments are described herein as Prophetic Examples.

PROPHETIC EXAMPLE 1

A system and method are described for competency training and use authorization for dispensing oxycodone. A user suffering from moderate to severe chronic pain receives an agent-dispensing device, e.g., a pill-dispensing container, filled with oxycodone by certified mail in response to a prescription that has been phoned into a dispensing pharmacy by the user's physician. The pill-dispensing container includes a locking mechanism and a controllable agent-dispensing mechanism and user identification circuitry.

The user receives a URL internet address for a web-based interactive tool via an e-mail communication from the dispensing pharmacy. The user accesses the web-based interactive tool using his laptop computer equipped with a wireless Internet connection through a router connected to an Internet provider. The URL Internet address provided by the pharmacy connects the user with the web-based interactive tool.

The user is required to log into the web-based interactive tool using login identification (ID) and a password. A login ID, e.g., the user's name or email address, and a password are provided to the user from the pharmacy or prescribing physician and are used the first time the user logs into the web-based interactive tool, but may be changed latter, e.g., to a password that the user is more likely to remember. Once the user is logged into the web-based interactive tool, he has immediate access to one or more of a training module, a verification module, and/or an activation module associated with the tool. If this is the first time that the user has used the web-based interactive tool, his access may be restricted to the training module. In this instance the training module must be completed before the user is able to access the other modules. If the user is a returning user and feels confident to complete the verification process without a training refresher, he may be able to access the verification module without first going through the training module.

The training module includes a series of web-pages with text and images providing information and instructions to the user regarding the proper use of the pill-dispensing container and the oxycodone. The information includes material provided in the prescribing information for oxycodone (see, e.g., prescribing information for oxycodone at http://www.drugs.com/pro/oxycodone.htlm, accessed Apr. 4, 2013 and a copy of which is incorporated herein by reference).

Once the user has been presented all of the material in the training module regarding the proper use of the pill-dispensing container and oxycodone, e.g., having clicked through all of the appropriate pages associated with the training module, the user is directed to the verification module. The verification module includes a multiple choice questionnaire including a series of 20 or more questions regarding the proper use and care of the pill-dispensing container and the prescribing information for oxycodone, including dosage, side-effects, and abuse potential. The verification module tabulates the number of correct responses to the 20 or more questions and assigns a questionnaire score, e.g., 18, to the user's answers and determines if the score meets or exceeds a pre-defined performance threshold, which in this example is 20. Because the user has not met the pre-defined performance threshold, he is required to review all of the training material in the training module and answer additional questions in the verification module. Once the user's questionnaire score reaches 20, the activation module provides a wireless signal to the pill-dispensing container to deactivate a locking mechanism. In this case, however, pills are only accessible when the controllable agent-dispensing mechanism is activated and this can only occur at specific times of the day and only after the user's identity has been verified with user identification circuitry associated with the pill-dispensing container, e.g., a fingerprint scanner associated with or incorporated into the pill-dispensing container. A report is sent via an e-mail to the user's physician indicating the user's questionnaire scores and whether or not the locking mechanism of the pill-dispensing container has been deactivated.

PROPHETIC EXAMPLE 2

A system and method are described for competency training and use authorization for dispensing fentanyl for continuous management of moderate to severe pain, e.g., for pain associated with end-stage cancer.

A hospice caregiver providing palliative care for a terminally ill individual in the individual's home receives transdermal fentanyl patches via courier from the sponsoring hospice organization, e.g., affiliated with a local hospital. The transdermal fentanyl patches are contained within a box-like structure with a locking mechanism operably linked to a controllable patch dispensing mechanism, e.g., a roller mechanism which rolls out an individually packaged patch in response to pushing a release button on the box-like structure. The locking mechanism prevents an electrical connection between the actuated release button and the roller mechanism. The box-like structure includes a receiver that is configured to receive a wireless communication, e.g., an activation signal, from the caregiver's smartphone.

The hospice caregiver accesses a web-based interactive tool using a URL supplied with the transdermal fentanyl patches. The hospice caregiver enters a personal authorization code as an authorized user of the fentanyl patches and a patient authorization code for the individual who will be receiving the fentanyl. An authorization module of the web-based interactive tool verifies that the authorization codes for the caregiver and the patient are authorized codes and directs the caregiver to a training module of the web-based interactive tool.

An experienced hospice caregiver is given the option of skipping the training material in the training module and going directly to the verification module. Once in the verification module, an audio-based questionnaire is administered to the hospice caregiver. The audio-based questionnaire includes 20 questions audibly provided to the hospice caregiver through the speakers of the smartphone. The hospice caregiver provides short answer responses to the 20 questions and the short answer responses are compared using voice recognition software associated with the verification module to determine whether or not each response is correct. The verification module assigns a performance score to the responses to the questionnaire, e.g., the percentage of correct responses, and determines whether or not the performance score meets or exceeds a pre-defined performance threshold, e.g., 95% correct responses. If the performance score does not meet 95% correct responses, the hospice caregiver is locked out of the verification module until training material in the training module is reviewed including instructions for the use of the transdermal fentanyl patches. If the performance score does meet or exceed 95% correct responses, then the activation module of the web-based interactive tool sends a wireless activation signal to a receiver of the box-like structure containing the fentanyl patches which in turn sends a signal to deactivate the locking mechanism to allow engagement of the rolling mechanism in response to pushing the release button. In some instances, an additional alphanumeric code may be required every time the hospice caregiver wants to access the fentanyl patches from the box-like structure to ensure that unauthorized individuals are unable to access the patches once the locking mechanism is deactivated.

PROPHETIC EXAMPLE 3

A device and method are described for competency training and use authorization for dispensing an inhaled medication from an agent-dispensing device, e.g., an inhaler. The inhaler includes use sensors and circuitry to monitor a series of operational steps for proper use of the inhaler. The inhaler includes a housing with a docking site for insertion of a replaceable cartridge containing an asthma medication, e.g., a bronchodilator. The inhaler further includes a microprocessor, a power source, switching circuitry, authorization circuitry, training circuitry, verification circuitry, activation circuitry, buttons, and an LED screen display.

Upon receipt of the inhaler, the user powers up the device and enters an authorization code, e.g., a password, into the inhaler using the buttons and the LED screen display. The authorization circuitry incorporated into the inhaler compares the password entered by the user with stored authorization codes and allows further access to functions of the inhaler if the user is an authorized user.

If the user has not previously gone through training with the inhaler, the switching circuitry of the inhaler switches the inhaler into training mode. In the training mode, operational steps for proper use of the inhaler are monitored by use sensors incorporated into the inhaler including a motion sensor, one or more pressure sensors, and a timing sensor. The use sensors are configured to monitor motion, e.g., shaking, and pressure, e.g., air flow and pressing of a button, as monitored over time by the timing sensor. Miniaturized sensors for measuring motion and pressure are known and available from, for example, Freescale Semiconductor, Inc., Austin, Tex., and Measurement Specialties, Hampton, Va. Non-limiting examples of inhalers with sensors, e.g., airflow sensors, are described in U.S. Pat. No. 5,363,842 and U.S. Pat. No. 7,322,355, which are incorporated herein by reference.

The training circuitry provides a step by step list of the operational steps for proper use of the inhaler through the LED screen display. The operational steps for proper use of the inhaler can include 1) removing cap from the mouth piece, 2) holding inhaler upright, 3) shaking inhaler 10-15 times, 4) placing the mouth piece in the mouth, 5) actuating by pressing down on the cartridge in the inhaler, 6) breathing in as pressing down on the cartridge, 7 holding breath, 8) breathing out, and 9) repeating if necessary. Once the user has read through the list of steps, the user is prompted to go through the operational steps with the inhaler in training mode, the use sensors monitoring one or more of the steps. A motion sensor, e.g., an accelerometer, is used to monitor the movement associated with shaking the inhaler. A mass air flow sensor (e.g., LMM-H03, Measurements Specialties, Hampton, Va.), measures the flow of air into the inhaler as the user breathes in. A pressure sensor monitors pressure associated with pressing down on the cartridge to release the bronchodilator from the cartridge. The timing associated with inhaling, as measured by the mass air flow and pressing down on the cartridge, as measured by the pressure sensor is noted as part of the performance. The training circuitry receives input from the use sensors and assigns a value to each operational step being monitored, e.g., from 0-5, where a score of 5 is a perfect performance of the operational step.

The verification circuitry determines if each individual assigned value meets or exceeds a pre-defined performance threshold for that operational step and if the sum of the assigned values meets or exceeds a pre-defined performance threshold for overall performance with the inhaler. If the verification circuitry determines that the appropriate thresholds are met or exceeded, a signal is sent to the activation circuitry which in turn sends an activation signal to deactivate a locking mechanism of the inhaler to allow dispensing of the bronchodilator. The activation circuitry is further linked to the authorization circuitry such that the activation signal will only be sent if the user is an authorized user.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:
1. An agent-dispensing device comprising:
a housing including
at least one reservoir configured to store one or more agents;

a controllable agent-dispensing mechanism in communication with the at least one reservoir;

a locking mechanism coupled to the controllable agent-dispensing mechanism;

a microprocessor including circuitry to operate the agent-dispensing device in a dispensing mode or a training mode and switching circuitry operable to switch operation of the agent-dispensing device between the dispensing mode and the training mode;

one or more use sensors located on the agent-dispensing device and responsive to at least one operational step for use of the agent-dispensing device in the training mode;

training circuitry operably linked to the one or more use sensors and configured to train the user in the at least one operational step for use of the agent-dispensing device in the training mode and to assign a value for each of the monitored at least one operational step for use of the agent-dispensing device performed by the user in the training mode based on feedback from the one or more use sensors;

verification circuitry configured to receive the assigned value for each of the monitored at least one operational step for use of the agent-dispensing device in the training mode, and to certify the user is competent to use the agent-dispensing device if the assigned value for each of the monitored at least one operational step for use of the agent-dispensing device meets or exceeds a pre-defined performance threshold; and activation circuitry responsive to the verification circuitry and configured to deactivate the locking mechanism if the user is certified competent to use the agent-dispensing device to allow dispensing of the one or more agents in the dispensing mode.

2. The device of claim 1, wherein the microprocessor is operably linked to at least one of the controllable agent-dispensing mechanism, the locking mechanism, the one or more use sensors, the training circuitry, the verification circuitry, or the activation circuitry.

3. The device of claim 1, further comprising:
authorization circuitry operably linked to the microprocessor and configured to authenticate the user as an authorized user of the agent-dispensing device by comparing a user input with a set of authorized user inputs.

4. The device of claim 3, wherein the user input includes at least one of an authorization code or a biometric parameter.

5. The device of claim 3, wherein the activation circuitry is responsive to the authorization circuitry and configured to deactivate the locking mechanism only for an authorized user of the agent-dispensing device.

6. The device of claim 1, wherein the housing includes a hand-held housing.

7. The device of claim 1, wherein the at least one reservoir includes at least one replaceable cartridge configured to be received by a docking site associated with the housing of the agent-dispensing device.

8. The device of claim 7, wherein the agent-dispensing device includes circuitry configured to read a cartridge identification code carried on the at least one replaceable cartridge.

9. The device of claim 1, wherein the one or more agents include at least one of one or more therapeutic agents or one or more preventative agents.

10. The device of claim 1, wherein the one or more use sensors include one or more of an accelerometer, a timer, an actuator, a pressure sensor, a touch sensor, a temperature sensor, an image capture device, or an inclinometer.

11. The device of claim 1, further comprising:
a user-device interface operably connected to one or more of the training circuitry, the verification circuitry, or the activation circuitry.

12. The device of claim 11, wherein the user-device interface is operably connected to authorization circuitry.

13. The device of claim 1, wherein the training circuitry includes one or more instructions for the at least one operational step for use of the agent-dispensing device, wherein the one or more instructions are accessible to the user through a user-device interface.

14. The device of claim 13, wherein the one or more instructions include at least one of one or more text-based instructions, image-based instructions, audio-based instructions, or video-based instructions.

15. The device of claim 13, wherein the one or more instructions for the at least one operational step for use of the agent-dispensing device are updateable.

16. The device of claim 1, wherein the output from the training circuitry is dependent upon one or more properties of the one or more agents.

17. The device of claim 1, wherein the training circuitry is configured to receive at least one signal from the one or more use sensors, the at least one signal including information regarding at least one of the monitored at least one operational step for use of the agent-dispensing device.

18. The device of claim 1, wherein the verification circuitry includes circuitry configured to receive a set of assigned values for each of the monitored at least one operational step for use of the agent-dispensing device from the training circuitry, and certify the user is competent to use the agent-dispensing device if each of the set of assigned values for each of the monitored at least one operational step for use of the agent-dispensing device meets or exceeds the pre-defined performance threshold.

19. The device of claim 1, wherein the verification circuitry includes circuitry configured to receive a set of assigned values for each of the monitored at least one operational step for use of the agent-dispensing device from the training circuitry, and certify the user is competent to use the agent-dispensing device if the sum of the set of assigned values for each of the monitored at least one operational step for use of the agent-dispensing device meets or exceeds the pre-defined performance threshold.

20. The device of claim 1, wherein the pre-defined performance threshold is updateable.

21. The device of claim 1, wherein the activation circuitry includes circuitry configured to receive a user identification and to provide a user-specific activation signal.

22. The device of claim 1, further comprising:
a transmission unit including an antenna configured to transmit and receive wireless signals.

23. A method of verifying user competency implemented with circuitry in an agent-dispensing device, comprising:
authenticating a user as an authorized user of the agent-dispensing device, wherein the agent-dispensing device includes a reservoir configured to store one or more agents, a controllable agent-dispensing mechanism in communication with the reservoir, a locking mechanism coupled to the controllable agent-dispensing mechanism, authorization circuitry, training circuitry, one or more use sensors, verification circuitry, and activation circuitry;

training the user in at least one operational step for use of the agent-dispensing device with one or more training instructions included in the training circuitry of the agent-dispensing device;

monitoring the user's performance of the at least one operational step for use of the agent-dispensing device with the one or more use sensors located on the agent-dispensing device;

assigning a value to each of the monitored at least one operational step for use of the agent-dispensing device performed by the user based on feedback from the one or more use sensors located on the agent-dispensing device;

verifying with the verification circuitry of the agent dispensing device that the user is competent to use the agent-dispensing device if the assigned value for each of the monitored at least one operational step for use of the agent-dispensing device meets or exceeds a pre-defined performance threshold; and activating the agent-dispensing device with the activation circuitry of the agent-dispensing device by sending an activation signal to deactivate the locking mechanism coupled to the controllable-agent dispensing mechanism of the agent-dispensing device to allow dispensing of the one or more agents from the agent-dispensing device if the user is verified competent to use the agent-dispensing device.

24. The method of claim 23, wherein authenticating the user as an authorized user of the agent-dispensing device includes receiving an authorization input from the user with a user-device interface associated with the agent-dispensing device;

comparing the received authorization input from the user with a set of approved authorization inputs; and unlocking access to at least one of the training circuitry, verification circuitry, or activation circuitry if the authorization input from the user satisfies a requirement of at least one of the set of approved authorization inputs.

25. The method of claim 23, wherein training the user in the at least one operational step for use of the agent-dispensing device with one or more training instructions included in the training circuitry includes providing the user with one or more of text, image, audio, or video content including one or more instructions for the at least one operational step for use of the agent-dispensing device.

* * * * *